US011473133B2

(12) United States Patent
Chow et al.

(10) Patent No.: US 11,473,133 B2
(45) Date of Patent: Oct. 18, 2022

(54) METHODS FOR VALIDATION OF MICROBIOME SEQUENCE PROCESSING AND DIFFERENTIAL ABUNDANCE ANALYSES VIA MULTIPLE BESPOKE SPIKE-IN MIXTURES

(71) Applicant: Second Genome, Inc., San Francisco, CA (US)

(72) Inventors: Cheryl-Emiliane T. Chow, San Francisco, CA (US); Todd Z. DeSantis, Livermore, CA (US); Roberta L. Hannibal, San Francisco, CA (US); Jayamary Divya Ravichandar, Forst City, CA (US); Nicole R. Narayan, San Francisco, CA (US)

(73) Assignee: Second Genome, Inc., Brisbane, CA (US)

( * ) Notice: Subject to any disclaimer, the term of this patent is extended or adjusted under 35 U.S.C. 154(b) by 108 days.

(21) Appl. No.: 16/581,712

(22) Filed: Sep. 24, 2019

(65) Prior Publication Data
US 2020/0140925 A1    May 7, 2020

Related U.S. Application Data

(60) Provisional application No. 62/735,374, filed on Sep. 24, 2018.

(51) Int. Cl.
*C12Q 1/686* (2018.01)
*G16B 35/20* (2019.01)
(Continued)

(52) U.S. Cl.
CPC .......... *C12Q 1/686* (2013.01); *C12Q 1/6806* (2013.01); *G16B 20/00* (2019.02); *G16B 25/00* (2019.02);
(Continued)

(58) Field of Classification Search
CPC .......... C12N 15/1072; G01N 33/5091; G01N 33/56911; G16B 20/00; G16B 40/20;
(Continued)

(56) References Cited

U.S. PATENT DOCUMENTS 10,392,670 B2 *  8/2019  Wang .................... C12Q 1/689
2014/0200149 A1 * 7/2014  Andersen ............... C12Q 1/689
                                                             506/14

(Continued)

FOREIGN PATENT DOCUMENTS

WO    WO 2013/130674    9/2013
WO    WO 2014/190394    12/2014
(Continued)

OTHER PUBLICATIONS

Fischer, M. et al. (2017) Abundance estimation and differential testing on strain level in metagenomics data. Bioinformatics 33: i24-i 32. (Year: 2017).*

(Continued)

*Primary Examiner* — Mary K Zeman
(74) *Attorney, Agent, or Firm* — Fish & Richardson P.C.

(57) ABSTRACT

Compositions, systems and methods for generating and using internal standard spike-in mixes including a combination of template spikes. Compositions, systems and methods described herein are directed to using the internal standard spike-in mixes to evaluate a set of workflow pipelines to perform differential abundance analyses on a sample containing variations of a target nucleic acid sequence of interest. Compositions, systems and methods described herein are directed to using the internal spike-in mixes to validate results obtained from differential abundance analyses performed on a sample containing variations (Continued)

of a target nucleic acid sequence of interest, where the variations may be of highly variable levels of relative abundance.

13 Claims, 62 Drawing Sheets

Specification includes a Sequence Listing.

(51) Int. Cl.
```
G16B 30/00      (2019.01)
C12Q 1/6806     (2018.01)
G16B 25/00      (2019.01)
G16B 40/00      (2019.01)
G16B 20/00      (2019.01)
```
(52) U.S. Cl.
CPC .............. *G16B 30/00* (2019.02); *G16B 35/20* (2019.02); *G16B 40/00* (2019.02)

(58) Field of Classification Search
CPC ........ G16B 25/00; G16B 30/00; G16B 30/10; G16B 35/20; G16B 40/00; G16B 5/00; G16B 40/30; G16B 5/20; G16B 20/50; G16B 25/10; G16B 45/00; G16H 10/40; G16H 10/60; G16H 50/20; G16H 50/30; G16H 50/70; G16H 70/60; C40B 40/02; C40B 40/06; C12Q 1/689; C12Q 2600/158; C12Q 2600/156; C12Q 1/6895; C12Q 1/6893; C12Q 1/6851; C12Q 2537/165; C12Q 2600/166; C12Q 2537/16; C12Q 2545/101; C12Q 1/06; C12Q 2600/112; C12Q 2600/16; C12Q 2560/00; C12Q 2600/00

See application file for complete search history.

(56) References Cited

U.S. PATENT DOCUMENTS

| | | | | |
|---|---|---|---|---|
| 2015/0322492 | A1* | 11/2015 | Huang | C12Q 1/689 506/4 |
| 2015/0344938 | A1* | 12/2015 | Bramlett | C12Q 1/6874 506/9 |
| 2018/0080065 | A1* | 3/2018 | Jain | A61K 35/741 |
| 2018/0365375 | A1* | 12/2018 | Flygare | G16B 40/20 |
| 2019/0177781 | A1* | 6/2019 | Beckman | C12Q 1/6851 |

FOREIGN PATENT DOCUMENTS

| | | |
|---|---|---|
| WO | WO 2016/025796 | 2/2016 |
| WO | WO-2020041449 A1 * | 2/2020 |

OTHER PUBLICATIONS

Amir et al., "Deblur Rapidly Resolves Single-Nucleotide Community Sequence Patterns", mSystems, vol. 2, Issue 2, e00191-16, 2017.
Balint et al., "Millions of reads, thousands of taxa: microbial community structure and associations analyzed via marker genes", FEMS Microbiology Reviews, 15 pages, 2016.
Callahan et al., "DADA2: High-resolution sample inference from Illumina amplicon data", Nature Methods, 13(7), 581-583, 2016.
Caporaso et al., "Global patterns of 16S rRNA diversity at a depth of millions of sequences per sample", PNAS, vol. 108, No. Supplement 1, pp. 4516-4522, 2010.
Caporaso et al., "Global patterns of 16S rRNA diversity at a depth of millions of sequences per sample", PNAS, 108: 4516-4522, 2011.
Caporaso et al., "QIIME allows analysis of high-throughput community sequencing data", Nature Methods, 7(5), 335-336, 2010.
Chakrabarti et al., "Resolving microbial membership using Abundance and Variability in Taxonomy (AVIT)", Scientific Reports, 6: 31655, 11 pages, 2016.
Cuesta-Zuluaga et al., "Considerations for Optimizing Microbiome Analysis Using a Marker Gene", Frontiers in Nutrition vol. 3, 26, 12 pages, 2016.
Deveson et al., "Representing genetic variation with synthetic DNDNA standards", Nature Methods vol. 13, pp. 784-791, 2016.
Edgar, "Search and clustering orders of magnitude faster than BLAST", Bioinformatics, 26: 2460-2461, 2010.
Endrullat et al., "Standardization and quality management in next-generation sequencing", Applied & Translational Genomics 10, 2-9, 2016.
Gifford et al., "Quantitative analysis of a deeply sequenced marine microbial metatranscriptome", The ISME Journal, 5, 461-472, 2011.
Gohl et al., "Systematic improvement of amplicon marker gene methods for increased accuracy in microbiome studies", Nature Biotechnology vol. 34, pp. 942-949, 2016.
Hardwick et al., "Spliced synthetic genes as internal controls in RNA sequencing experiments", Nature Methods vol. 13, pp. 792-798, 2016.
Hathaway et al., SeekDeep: single-base resolution de novo clustering for amplicon deep sequencing, Nucleic Acids Research, 46(4), e21-e21, 2018.
Inivitation to Pay Additional Fees in International Application No. PCT/US2019/052802, dated Jan. 15, 2020, 18 pages.
Jiang et al., "Synthetic spike-in standards for RNA-seq experiments", 21: 1543-1551, 2011.
Law et al., "voom: precision weights unlock linear model analysis tools for RNA-seq read counts", Genome Biology, 15(2), R29, 2014.
Ledergerber et al., "Base-calling for next-generation sequencing platforms", Briefings in Bioinformatics. Vol 12. No. 5. 489-497, 2011.
Lemire et al., "Development of ERCC RNA Spike-In Control Mixes", Journal of Biomolecular Techniques, vol. 22, Supplement, Oct. 2011, 1 pages.
Love et al., "Moderated estimation of fold change and dispersion for RNA-seq data with DESeq2", Genome Biol, 15: 1-21,2014.
McCarthy et al., "Differential expression analysis of multifactor RNA-Seq experiments with respect to biological variation", Nucleic Acids Res, 40: 4288-4297, 2012.
McMurdie and Holmes, "Waste Not, Want Not: Why Rarefying Microbiome Data is Inadmissible", PLoS ComputBio 10, 12 pages, 2015.
McMurdie et al., "Waste Not, Want Not: Why Rarefying Microbiome Data is Inadmissible", PLoS Computational Biology, 10(4), e!003531, 12 pages, 2014.
Moran et al., "Assessing technical performance in differential gene expression experiments with external spike-in RNA control ratio mixtures", Nature Communications, 5: 5125, 10 pages, 2014.
Moran et al., "Sizing up metatranscriptomics", The ISME Journal, 1-7, 2012.
Paulson et al., "Differential abundance analysis for microbial marker-gene surveys.", Nat. Methods, 10: 1200-1202, 2013.
Pei et al., "Diversity of 16S rRNA Genes within Individual Prokaryotic Genomes", vol. 76, No. 12, pp. 3886-3897, 2010.
Robinson et al., "edgeR: a Bioconductor package for differential expression analysis of digital gene expression data", Bioinformatics, 26(1), 139-140, 2009.
Satinsky et al., "Use of Internal Standards for Quantitative Metatranscriptome and Metagenome Analysis", Methods in Enzymology, vol. 531, 237-250, 2013.
Schloss et al., "Introducing mothur: Open-Source, Platform Independent, Community-Supported Software for Describing and Comparing Microbial Communities", Applied and Environmental Microbiology, 75(23), 7537-7541, 2009.
Smets et al., "A method for simultaneous measurement of soil bacterial abundances and community composition via 16S rRNA gene sequencing", Soil Biology & Biochemistiy 96, 145-151, 2016.

(56) References Cited

OTHER PUBLICATIONS

Stämmler et al., "Adjusting microbiome profiles for differences in microbial load by spike-in bacteria", Stämmler et al. Microbiome, 4: 28, 13 pages, 2016.

Thorsen et al., "Large-scale benchmarking reveals false discoveries and count transformation sensitivity in 16S rRNA gene amplicon data analysis methods used in microbiome studies", Microbiome, 4: 62, 14 pages, 2016.

Tourlousse et al., "Synthetic spike-in standards for high-throughput 16S rRNA gene amplicon sequencing", Nucleic Acids Research, vol. 45, No. 4, 14 pages, 2017.

Warnes GR, Bolker B, Lumley T., "gtools: Various R Programming Tools.", 3.8.1, 2 pages, 2018.

PCT International Preliminary Report on Patentability in International Appln. No. PCT/US2019/052802, dated Apr. 1, 2021, 15 pages.

Tourlousse et al., "Supplementary data for synthetic spike-in standards for high-throughput 16S rRNA gene amplicon sequencing," Nucleic Acids Res, 2017, 46 pages.

International Search Report and Written Opinion in Appln. No. PCTUS2019052802, dated Mar. 20, 2020, 21 pages.

\* cited by examiner

| 16S V4 For | Non-16S NIST Sequence | 16S V4 Rev |

FIG. 3A

| V4-F | Non-16S sequence | V4-R |
| V4-F | Non-16S sequence | V4-R |

FIG. 3B

| FWD primer | Non-16S sequence A | REV primer |
| FWD primer | Non-16S sequence B | REV primer |
| FWD primer | Non-16S sequence C | REV primer |

FIG. 3C

| Spike category | Expected [input] abundance | Max Relative Abundance | Max Relative Abundance | Num spikes | Num expected NULL shifts | Num expected sig DA |
|---|---|---|---|---|---|---|
| High | > 1000 | > 0.001 | >0.1% | 37 | 8 | 103 |
| Low | 50 - 1000 | 0.0003 - 0.001 | 0.03 - 0.1% | 18 | 9 | 45 |
| Ultra-low | < 50 | < 0.0003 | <0.03% | 14 | 15 | 27 |

FIG. 8C

| n = 165 | Predicted: NO | Predicted: YES |
|---|---|---|
| Actual: NO | 50 | 10 |
| Actual: YES | 5 | 100 |

FIG. 10A

|  |  | Predicted (Observed) | | |
|---|---|---|---|---|
|  |  | Positive | Negative | |
| Actual (Expected) | Positive | TP = 105 | FN = 20 | 125 |
|  | Negative | FP = 15 | TN = 55 | 70 |
|  |  | 120 | 75 | N = 195 |

FIG. 10B

| Spike category | Expected [input] abundance | Max Relative Abundance (0-1) | Max Relative Abundance (%) | Spk16 PPV DDSS | Spk16 PPV DDSSr:Q5 | Spk16 PPV DDSSmr:Q2 |
|---|---|---|---|---|---|---|
| High | >1000 | >0.001 | >0.1% | 0.9690 | 0.9896 | 0.9796 |
| Low | 50-1000 | 0.0003-0.001 | 0.03-0.1% | 0.9696 | 0.9210 | 0.9793 |
| Ultra-low | <50 | <0.0003 | <0.03% | 0.5714 | 0.7272 | 0.6667 |

FIG. 18B

| dtype | Overall_score_v4 | Rank_score_v4 |
|---|---|---|
| DESeq2_poscounts_DDSSmr | 6.7552 | 1 |
| DESeq2_poscounts_DDSS_RelaxedQ | 6.7371 | 2 |
| DESeq2_betapriors_DDSS_RelaxedQ | 6.6952 | 3 |
| edgeR_DDSS_RelaxedQ | 6.6845 | 4 |
| t.test_DDSS_RelaxedQ | 6.6502 | 5 |
| DESeq2_betapriors_SSDD | 6.6378 | 6 |
| DESeq2_poscounts_SSDD | 6.6270 | 7 |
| t.test_SSDD | 6.5875 | 8 |
| DESeq2_poscounts_SSDD_RelaxedQ | 6.5487 | 9 |
| DESeq2_betapriors_SSDD_RelaxedQ | 6.5162 | 10 |
| DESeq2_poscounts_DDSS | 6.4755 | 11 |
| DESeq2_betapriors_DDSS | 6.4755 | 12 |
| t.test_DDSS | 6.4754 | 13 |
| edgeR_SSDD | 6.4506 | 14 |
| edgeR_DDSS | 6.4015 | 15 |
| DESeq2_poscounts_SS16UP | 6.2858 | 16 |
| DESeq2_betapriors_SS16UP | 6.2701 | 17 |
| edgeR_SS16UP | 6.2336 | 18 |
| t.test_SS16UP | 6.2289 | 19 |
| metagenomeSeq2_DDSS_RelaxedQ | 5.5766 | 20 |
| metagenomeSeq2_SS16UP | 5.3393 | 21 |
| metagenomeSeq2_DDSS | 5.2635 | 22 |
| edgeR_SSUP | 5.0183 | 23 |
| metagenomeSeq2_SSDD | 5.0169 | 24 |
| t.test_SSUP | 4.8761 | 25 |
| DESeq2_poscounts_SSUP | 4.8529 | 26 |
| DESeq2_betapriors_SSUP | 4.8303 | 27 |
| metagenomeSeq2_SSUP | 4.4604 | 28 |

FIG. 22A

| dtype | Overall_score_v4 | Rank_score_v4 |
|---|---|---|
| DESeq2.poscounts_DDSS.mr | 6.755175905 | 1 |
| DESeq2.poscounts_DDSS.RelaxedQ | 6.73712494 | 2 |
| DESeq2.betapriors_DDSS.mr | 6.723690203 | 3 |
| edgeR_DDSS.mr | 6.7025209 | 4 |
| DESeq2.betapriors_DDSS.RelaxedQ | 6.69526022 | 5 |
| edgeR_DDSS.RelaxedQ | 6.680874624 | 6 |
| ttest_DDSS.mr | 6.662457802 | 7 |
| ttest_DDSS.RelaxedQ | 6.650216877 | 8 |
| DESeq2.betapriors_SSDD | 6.637992378 | 9 |
| DESeq2.poscounts_SSDD | 6.627138812 | 10 |
| ttest_SSDD | 6.587715321 | 11 |
| DESeq2.poscounts_SSDD.RelaxedQ | 6.5465366 | 12 |
| ttest_SSDD.RelaxedQ | 6.519367998 | 13 |
| DESeq2.betapriors_SSDD.RelaxedQ | 6.51406808 | 14 |
| DESeq2.poscounts_DDSS | 6.476294495 | 15 |
| DESeq2.betapriors_DDSS | 6.476259849 | 16 |
| ttest_DDSS | 6.476185003 | 17 |
| edgeR_SSDD | 6.450961966 | 18 |
| edgeR_DDSS | 6.402663889 | 19 |
| edgeR_SSDD.RelaxedQ | 6.291087043 | 20 |
| DESeq2.poscounts_SS16UP | 6.285903575 | 21 |
| DESeq2.betapriors_SS16UP | 6.270211949 | 22 |
| edgeR_SS16UP | 6.233911972 | 23 |
| ttest_SS16UP | 6.229096927 | 24 |
| mtgseq_DDSS.RelaxedQ | 5.578379128 | 25 |
| mtgseq_SS16UP | 5.340914401 | 26 |
| mtgseq_DDSS.mr | 5.270739124 | 27 |
| mtgseq_DDSS | 5.266108474 | 28 |
| mtgseq_SSDD | 5.01853719 | 29 |
| edgeR_SSUP | 5.017535799 | 30 |
| mtgseq_SSDD.RelaxedQ | 4.989782622 | 31 |
| ttest_SSUP | 4.875188106 | 32 |
| DESeq2.poscounts_SSUP | 4.852919466 | 33 |
| DESeq2.betapriors_SSUP | 4.830290033 | 34 |
| mtgseq_SSUP | 4.459921769 | 35 |

FIG. 22B

SEQUENCE LISTING

<160> NUMBER OF SEQ ID NOS: 172

<210> SEQ ID NO 1
<211> LENGTH: 19
<212> TYPE: DNA
<213> ORGANISM: Artificial
<220> FEATURE:
<223> OTHER INFORMATION: synthetic primer

<400> SEQUENCE: 1
gtgccagcmg ccgcggtaa                                                    19

<210> SEQ ID NO 2
<211> LENGTH: 53
<212> TYPE: DNA
<213> ORGANISM: Artificial
<220> FEATURE:
<223> OTHER INFORMATION: synthetic primer

<400> SEQUENCE: 2
aatgatacgg cgaccaccga gacgtacgta cggtgtgcca gcmgccgcgg taa              53

<210> SEQ ID NO 3
<211> LENGTH: 68
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (25)..(36)
<223> OTHER INFORMATION: n is a, c, g, or t

<400> SEQUENCE: 3
caagcagaag acggcatacg agatnnnnnn nnnnnnagtc agtcagccgg actachvggg       60 twtctaat                                                                68

<210> SEQ ID NO 4
<211> LENGTH: 20
<212> TYPE: DNA
<213> ORGANISM: Artificial
<220> FEATURE:
<223> OTHER INFORMATION: synthetic primer

<400> SEQUENCE: 4
ggactachvg ggtwtctaat                                                   20

```
<210> SEQ ID NO 5
<211> LENGTH: 39
<212> TYPE: DNA
<213> ORGANISM: Artificial
<220> FEATURE:
<223> OTHER INFORMATION: synthetic primer

<400> SEQUENCE: 5
gtgccagcmg ccgcggtaac ttctcataac cgtctccga                              39

<210> SEQ ID NO 6
<211> LENGTH: 39
<212> TYPE: DNA
<213> ORGANISM: Artificial
<220> FEATURE:
<223> OTHER INFORMATION: synthetic primer

<400> SEQUENCE: 6
gtgccagcmg ccgcggtaac ttatagtgct tgctagcac                              39

<210> SEQ ID NO 7
<211> LENGTH: 39
<212> TYPE: DNA
<213> ORGANISM: Artificial
<220> FEATURE:
<223> OTHER INFORMATION: synthetic primer

<400> SEQUENCE: 7
gtgccagcmg ccgcggtaaa gattattgaa aaagctggt                              39

<210> SEQ ID NO 8
<211> LENGTH: 39
<212> TYPE: DNA
<213> ORGANISM: Artificial
<220> FEATURE:
<223> OTHER INFORMATION: synthetic primer

<400> SEQUENCE: 8
gtgccagcmg ccgcggtaac cagtaattct accacgcct                              39

<210> SEQ ID NO 9
<211> LENGTH: 39
<212> TYPE: DNA
<213> ORGANISM: Artificial
<220> FEATURE:
<223> OTHER INFORMATION: synthetic primer

<400> SEQUENCE: 9
gtgccagcmg ccgcggtaaa ttgaactcaa gggacggtg                              39

<210> SEQ ID NO 10
<211> LENGTH: 39
<212> TYPE: DNA
<213> ORGANISM: Artificial
<220> FEATURE:
<223> OTHER INFORMATION: synthetic primer

<400> SEQUENCE: 10
gtgccagcmg ccgcggtaaa ctctttagc tgcaggaca                               39

<210> SEQ ID NO 11
<211> LENGTH: 39
<212> TYPE: DNA
<213> ORGANISM: Artificial
<220> FEATURE:
<223> OTHER INFORMATION: synthetic primer
```

<400> SEQUENCE: 11
gtgccagcmg ccgcggtaaa actcaacaga cagctctgg                          39

<210> SEQ ID NO 12
<211> LENGTH: 39
<212> TYPE: DNA
<213> ORGANISM: Artificial
<220> FEATURE:
<223> OTHER INFORMATION: synthetic primer

<400> SEQUENCE: 12
gtgccagcmg ccgcggtaat gggatacttc gatagcgtt                          39

<210> SEQ ID NO 13
<211> LENGTH: 39
<212> TYPE: DNA
<213> ORGANISM: Artificial
<220> FEATURE:
<223> OTHER INFORMATION: synthetic primer

<400> SEQUENCE: 13
gtgccagcmg ccgcggtaaa cgagatcaca gaaaatcgc                          39

<210> SEQ ID NO 14
<211> LENGTH: 39
<212> TYPE: DNA
<213> ORGANISM: Artificial
<220> FEATURE:
<223> OTHER INFORMATION: synthetic primer

<400> SEQUENCE: 14
gtgccagcmg ccgcggtaag catataggaa acgatgggc                          39

<210> SEQ ID NO 15
<211> LENGTH: 39
<212> TYPE: DNA
<213> ORGANISM: Artificial
<220> FEATURE:
<223> OTHER INFORMATION: synthetic primer

<400> SEQUENCE: 15
gtgccagcmg ccgcggtaaa taatatcttc gcctcctca                          39

<210> SEQ ID NO 16
<211> LENGTH: 39
<212> TYPE: DNA
<213> ORGANISM: Artificial
<220> FEATURE:
<223> OTHER INFORMATION: synthetic primer

<400> SEQUENCE: 16
gtgccagcmg ccgcggtaaa acagaaacta ctggggcga                          39

<210> SEQ ID NO 17
<211> LENGTH: 39
<212> TYPE: DNA
<213> ORGANISM: Artificial
<220> FEATURE:
<223> OTHER INFORMATION: synthetic primer

<400> SEQUENCE: 17
gtgccagcmg ccgcggtaac acttacgatt gcgatgacg                          39

<210> SEQ ID NO 18

<211> LENGTH: 39
<212> TYPE: DNA
<213> ORGANISM: Artificial
<220> FEATURE:
<223> OTHER INFORMATION: synthetic primer

<400> SEQUENCE: 18
gtgccagcmg ccgcggtaaa tcaacgacat tggcccaga         39

<210> SEQ ID NO 19
<211> LENGTH: 39
<212> TYPE: DNA
<213> ORGANISM: Artificial
<220> FEATURE:
<223> OTHER INFORMATION: synthetic primer

<400> SEQUENCE: 19
gtgccagcmg ccgcggtaac agcgactaga ttttaggca         39

<210> SEQ ID NO 20
<211> LENGTH: 39
<212> TYPE: DNA
<213> ORGANISM: Artificial
<220> FEATURE:
<223> OTHER INFORMATION: synthetic primer

<400> SEQUENCE: 20
gtgccagcmg ccgcggtaac tagattctag gtatttcgg         39

<210> SEQ ID NO 21
<211> LENGTH: 39
<212> TYPE: DNA
<213> ORGANISM: Artificial
<220> FEATURE:
<223> OTHER INFORMATION: synthetic primer

<400> SEQUENCE: 21
gtgccagcmg ccgcggtaag tgagcattaa atttacgtg         39

<210> SEQ ID NO 22
<211> LENGTH: 39
<212> TYPE: DNA
<213> ORGANISM: Artificial
<220> FEATURE:
<223> OTHER INFORMATION: synthetic primer

<400> SEQUENCE: 22
gtgccagcmg ccgcggtaag cttgatcgaa aaaaagcag         39

<210> SEQ ID NO 23
<211> LENGTH: 39
<212> TYPE: DNA
<213> ORGANISM: Artificial
<220> FEATURE:
<223> OTHER INFORMATION: synthetic primer

<400> SEQUENCE: 23
gtgccagcmg ccgcggtaaa ggcttgtcac acatcacgt         39

<210> SEQ ID NO 24
<211> LENGTH: 39
<212> TYPE: DNA
<213> ORGANISM: Artificial
<220> FEATURE:
<223> OTHER INFORMATION: synthetic primer

<400> SEQUENCE: 24
gtgccagcmg ccgcggtaaa aagaaggag ataaggttg                    39

<210> SEQ ID NO 25
<211> LENGTH: 39
<212> TYPE: DNA
<213> ORGANISM: Artificial
<220> FEATURE:
<223> OTHER INFORMATION: synthetic primer

<400> SEQUENCE: 25
gtgccagcmg ccgcggtaaa ttctcttatc gagagcccg                   39

<210> SEQ ID NO 26
<211> LENGTH: 39
<212> TYPE: DNA
<213> ORGANISM: Artificial
<220> FEATURE:
<223> OTHER INFORMATION: synthetic primer

<400> SEQUENCE: 26
gtgccagcmg ccgcggtaaa ttagcgtaga tactcttcc                   39

<210> SEQ ID NO 27
<211> LENGTH: 39
<212> TYPE: DNA
<213> ORGANISM: Artificial
<220> FEATURE:
<223> OTHER INFORMATION: synthetic primer

<400> SEQUENCE: 27
gtgccagcmg ccgcggtaac tatccctaca tcaacacca                   39

<210> SEQ ID NO 28
<211> LENGTH: 39
<212> TYPE: DNA
<213> ORGANISM: Artificial
<220> FEATURE:
<223> OTHER INFORMATION: synthetic primer

<400> SEQUENCE: 28
gtgccagcmg ccgcggtaat gctggctcat gtttccttc                   39

<210> SEQ ID NO 29
<211> LENGTH: 39
<212> TYPE: DNA
<213> ORGANISM: Artificial
<220> FEATURE:
<223> OTHER INFORMATION: synthetic primer

<400> SEQUENCE: 29
gtgccagcmg ccgcggtaag acgattcaca gataaggac                   39

<210> SEQ ID NO 30
<211> LENGTH: 39
<212> TYPE: DNA
<213> ORGANISM: Artificial
<220> FEATURE:
<223> OTHER INFORMATION: synthetic primer

<400> SEQUENCE: 30
gtgccagcmg ccgcggtaac agagcttaag caatatggc                   39

<210> SEQ ID NO 31
<211> LENGTH: 39
<212> TYPE: DNA

```
<213> ORGANISM: Artificial
<220> FEATURE:
<223> OTHER INFORMATION: synthetic primer

<400> SEQUENCE: 31
gtgccagcmg ccgcggtaaa agtaatctgg tccgcgact                    39

<210> SEQ ID NO 32
<211> LENGTH: 39
<212> TYPE: DNA
<213> ORGANISM: Artificial
<220> FEATURE:
<223> OTHER INFORMATION: synthetic primer

<400> SEQUENCE: 32
gtgccagcmg ccgcggtaat agacgagata gggtaagcc                    39

<210> SEQ ID NO 33
<211> LENGTH: 39
<212> TYPE: DNA
<213> ORGANISM: Artificial
<220> FEATURE:
<223> OTHER INFORMATION: synthetic primer

<400> SEQUENCE: 33
gtgccagcmg ccgcggtaac tgttaagttt tcaatggct                    39

<210> SEQ ID NO 34
<211> LENGTH: 39
<212> TYPE: DNA
<213> ORGANISM: Artificial
<220> FEATURE:
<223> OTHER INFORMATION: synthetic primer

<400> SEQUENCE: 34
gtgccagcmg ccgcggtaat tcttctcaag ttgtgcttc                    39

<210> SEQ ID NO 35
<211> LENGTH: 39
<212> TYPE: DNA
<213> ORGANISM: Artificial
<220> FEATURE:
<223> OTHER INFORMATION: synthetic primer

<400> SEQUENCE: 35
gtgccagcmg ccgcggtaag atcctgtagt aatccggga                    39

<210> SEQ ID NO 36
<211> LENGTH: 39
<212> TYPE: DNA
<213> ORGANISM: Artificial
<220> FEATURE:
<223> OTHER INFORMATION: synthetic primer

<400> SEQUENCE: 36
gtgccagcmg ccgcggtaag cgcagatatg ctatacgag                    39

<210> SEQ ID NO 37
<211> LENGTH: 39
<212> TYPE: DNA
<213> ORGANISM: Artificial
<220> FEATURE:
<223> OTHER INFORMATION: synthetic primer

<400> SEQUENCE: 37
gtgccagcmg ccgcggtaag ggttattatc gtcgcggtt                    39
```

<210> SEQ ID NO 38
<211> LENGTH: 39
<212> TYPE: DNA
<213> ORGANISM: Artificial
<220> FEATURE:
<223> OTHER INFORMATION: synthetic primer

<400> SEQUENCE: 38
gtgccagcmg ccgcggtaac atgttatagg gctgcgaac                              39

<210> SEQ ID NO 39
<211> LENGTH: 39
<212> TYPE: DNA
<213> ORGANISM: Artificial
<220> FEATURE:
<223> OTHER INFORMATION: synthetic primer

<400> SEQUENCE: 39
gtgccagcmg ccgcggtaac agaatatata aagcgtgac                              39

<210> SEQ ID NO 40
<211> LENGTH: 39
<212> TYPE: DNA
<213> ORGANISM: Artificial
<220> FEATURE:
<223> OTHER INFORMATION: synthetic primer

<400> SEQUENCE: 40
gtgccagcmg ccgcggtaat tcgccaccca tataaaccc                              39

<210> SEQ ID NO 41
<211> LENGTH: 39
<212> TYPE: DNA
<213> ORGANISM: Artificial
<220> FEATURE:
<223> OTHER INFORMATION: synthetic primer

<400> SEQUENCE: 41
gtgccagcmg ccgcggtaaa ctcgcattca ctaacatgg                              39

<210> SEQ ID NO 42
<211> LENGTH: 39
<212> TYPE: DNA
<213> ORGANISM: Artificial
<220> FEATURE:
<223> OTHER INFORMATION: synthetic primer

<400> SEQUENCE: 42
gtgccagcmg ccgcggtaaa ttaacacatc tattggctc                              39

<210> SEQ ID NO 43
<211> LENGTH: 39
<212> TYPE: DNA
<213> ORGANISM: Artificial
<220> FEATURE:
<223> OTHER INFORMATION: synthetic primer

<400> SEQUENCE: 43
gtgccagcmg ccgcggtaaa agttttttgaa gcaatgggg                             39

<210> SEQ ID NO 44
<211> LENGTH: 39
<212> TYPE: DNA
<213> ORGANISM: Artificial
<220> FEATURE:

<223> OTHER INFORMATION: synthetic primer

<400> SEQUENCE: 44
gtgccagcmg ccgcggtaaa gatatgccat gcgtgctgt                                39

<210> SEQ ID NO 45
<211> LENGTH: 39
<212> TYPE: DNA
<213> ORGANISM: Artificial
<220> FEATURE:
<223> OTHER INFORMATION: synthetic primer

<400> SEQUENCE: 45
gtgccagcmg ccgcggtaaa gttcgataaa tgagacgtc                                39

<210> SEQ ID NO 46
<211> LENGTH: 39
<212> TYPE: DNA
<213> ORGANISM: Artificial
<220> FEATURE:
<223> OTHER INFORMATION: synthetic primer

<400> SEQUENCE: 46
gtgccagcmg ccgcggtaaa tcgtaatatt ggcggttgc                                39

<210> SEQ ID NO 47
<211> LENGTH: 39
<212> TYPE: DNA
<213> ORGANISM: Artificial
<220> FEATURE:
<223> OTHER INFORMATION: synthetic primer

<400> SEQUENCE: 47
gtgccagcmg ccgcggtaaa gttatttgat taaggtgac                                39

<210> SEQ ID NO 48
<211> LENGTH: 39
<212> TYPE: DNA
<213> ORGANISM: Artificial
<220> FEATURE:
<223> OTHER INFORMATION: synthetic primer

<400> SEQUENCE: 48
gtgccagcmg ccgcggtaag tcagaagaat cgatagagc                                39

<210> SEQ ID NO 49
<211> LENGTH: 39
<212> TYPE: DNA
<213> ORGANISM: Artificial
<220> FEATURE:
<223> OTHER INFORMATION: synthetic primer

<400> SEQUENCE: 49
gtgccagcmg ccgcggtaac aatacctaac caaatccgc                                39

<210> SEQ ID NO 50
<211> LENGTH: 39
<212> TYPE: DNA
<213> ORGANISM: Artificial
<220> FEATURE:
<223> OTHER INFORMATION: synthetic primer

<400> SEQUENCE: 50
gtgccagcmg ccgcggtaac aagctgtgat gagactgct                                39

<210> SEQ ID NO 51
<211> LENGTH: 39
<212> TYPE: DNA
<213> ORGANISM: Artificial
<220> FEATURE:
<223> OTHER INFORMATION: synthetic primer

<400> SEQUENCE: 51
gtgccagcmg ccgcggtaaa acagaaacgt tatccgctt                          39

<210> SEQ ID NO 52
<211> LENGTH: 39
<212> TYPE: DNA
<213> ORGANISM: Artificial
<220> FEATURE:
<223> OTHER INFORMATION: synthetic primer

<400> SEQUENCE: 52
gtgccagcmg ccgcggtaaa aagctgattg attacggga                          39

<210> SEQ ID NO 53
<211> LENGTH: 39
<212> TYPE: DNA
<213> ORGANISM: Artificial
<220> FEATURE:
<223> OTHER INFORMATION: synthetic primer

<400> SEQUENCE: 53
gtgccagcmg ccgcggtaaa ctctttcaaa acttcggtg                          39

<210> SEQ ID NO 54
<211> LENGTH: 39
<212> TYPE: DNA
<213> ORGANISM: Artificial
<220> FEATURE:
<223> OTHER INFORMATION: synthetic primer

<400> SEQUENCE: 54
gtgccagcmg ccgcggtaat acaatcgcac cagttagcg                          39

<210> SEQ ID NO 55
<211> LENGTH: 39
<212> TYPE: DNA
<213> ORGANISM: Artificial
<220> FEATURE:
<223> OTHER INFORMATION: synthetic primer

<400> SEQUENCE: 55
gtgccagcmg ccgcggtaat agcagactct acattggcc                          39

<210> SEQ ID NO 56
<211> LENGTH: 39
<212> TYPE: DNA
<213> ORGANISM: Artificial
<220> FEATURE:
<223> OTHER INFORMATION: synthetic primer

<400> SEQUENCE: 56
gtgccagcmg ccgcggtaat agatgtcgta tccggagga                          39

<210> SEQ ID NO 57
<211> LENGTH: 39
<212> TYPE: DNA
<213> ORGANISM: Artificial
<220> FEATURE:
<223> OTHER INFORMATION: synthetic primer

<400> SEQUENCE: 57
gtgccagcmg ccgcggtaac gaatgtatga tggtcggtc                                39

<210> SEQ ID NO 58
<211> LENGTH: 39
<212> TYPE: DNA
<213> ORGANISM: Artificial
<220> FEATURE:
<223> OTHER INFORMATION: synthetic primer

<400> SEQUENCE: 58
gtgccagcmg ccgcggtaag ttatcatggt gactctgca                                39

<210> SEQ ID NO 59
<211> LENGTH: 39
<212> TYPE: DNA
<213> ORGANISM: Artificial
<220> FEATURE:
<223> OTHER INFORMATION: synthetic primer

<400> SEQUENCE: 59
gtgccagcmg ccgcggtaac ctaacgagtt tgatacgcc                                39

<210> SEQ ID NO 60
<211> LENGTH: 39
<212> TYPE: DNA
<213> ORGANISM: Artificial
<220> FEATURE:
<223> OTHER INFORMATION: synthetic primer

<400> SEQUENCE: 60
gtgccagcmg ccgcggtaaa tctataacaa ctgcgtcag                                39

<210> SEQ ID NO 61
<211> LENGTH: 39
<212> TYPE: DNA
<213> ORGANISM: Artificial
<220> FEATURE:
<223> OTHER INFORMATION: synthetic primer

<400> SEQUENCE: 61
gtgccagcmg ccgcggtaac tcaatcctag atacgttgc                                39

<210> SEQ ID NO 62
<211> LENGTH: 39
<212> TYPE: DNA
<213> ORGANISM: Artificial
<220> FEATURE:
<223> OTHER INFORMATION: synthetic primer

<400> SEQUENCE: 62
gtgccagcmg ccgcggtaac aagttaacgc cgatcactc                                39

<210> SEQ ID NO 63
<211> LENGTH: 39
<212> TYPE: DNA
<213> ORGANISM: Artificial
<220> FEATURE:
<223> OTHER INFORMATION: synthetic primer

<400> SEQUENCE: 63
gtgccagcmg ccgcggtaat gatacttaac caaacctac                                39

<210> SEQ ID NO 64
<211> LENGTH: 39

<212> TYPE: DNA
<213> ORGANISM: Artificial
<220> FEATURE:
<223> OTHER INFORMATION: synthetic primer

<400> SEQUENCE: 64
gtgccagcmg ccgcggtaaa gaattgtata gcttgcagg             39

<210> SEQ ID NO 65
<211> LENGTH: 39
<212> TYPE: DNA
<213> ORGANISM: Artificial
<220> FEATURE:
<223> OTHER INFORMATION: synthetic primer

<400> SEQUENCE: 65
gtgccagcmg ccgcggtaaa cattgattgc tgcattccg             39

<210> SEQ ID NO 66
<211> LENGTH: 39
<212> TYPE: DNA
<213> ORGANISM: Artificial
<220> FEATURE:
<223> OTHER INFORMATION: synthetic primer

<400> SEQUENCE: 66
gtgccagcmg ccgcggtaag atggaaaaat tagagagag             39

<210> SEQ ID NO 67
<211> LENGTH: 39
<212> TYPE: DNA
<213> ORGANISM: Artificial
<220> FEATURE:
<223> OTHER INFORMATION: synthetic primer

<400> SEQUENCE: 67
gtgccagcmg ccgcggtaat actacattcg tgcgatggg             39

<210> SEQ ID NO 68
<211> LENGTH: 39
<212> TYPE: DNA
<213> ORGANISM: Artificial
<220> FEATURE:
<223> OTHER INFORMATION: synthetic primer

<400> SEQUENCE: 68
gtgccagcmg ccgcggtaaa taaaaggat cgccatccg             39

<210> SEQ ID NO 69
<211> LENGTH: 39
<212> TYPE: DNA
<213> ORGANISM: Artificial
<220> FEATURE:
<223> OTHER INFORMATION: synthetic primer

<400> SEQUENCE: 69
gtgccagcmg ccgcggtaat ttcgacctct ctgtgtgga             39

<210> SEQ ID NO 70
<211> LENGTH: 39
<212> TYPE: DNA
<213> ORGANISM: Artificial
<220> FEATURE:
<223> OTHER INFORMATION: synthetic primer

<400> SEQUENCE: 70
gtgccagcmg ccgcggtaat tccaatactt ctatgcctc            39

<210> SEQ ID NO 71
<211> LENGTH: 39
<212> TYPE: DNA
<213> ORGANISM: Artificial
<220> FEATURE:
<223> OTHER INFORMATION: synthetic primer

<400> SEQUENCE: 71
gtgccagcmg ccgcggtaaa attgatcgtt gcgtacgga            39

<210> SEQ ID NO 72
<211> LENGTH: 39
<212> TYPE: DNA
<213> ORGANISM: Artificial
<220> FEATURE:
<223> OTHER INFORMATION: synthetic primer

<400> SEQUENCE: 72
gtgccagcmg ccgcggtaac gcagataaat gtggagcag            39

<210> SEQ ID NO 73
<211> LENGTH: 39
<212> TYPE: DNA
<213> ORGANISM: Artificial
<220> FEATURE:
<223> OTHER INFORMATION: synthetic primer

<400> SEQUENCE: 73
gtgccagcmg ccgcggtaat agtagatcac agaacaacc            39

<210> SEQ ID NO 74
<211> LENGTH: 39
<212> TYPE: DNA
<213> ORGANISM: Artificial
<220> FEATURE:
<223> OTHER INFORMATION: synthetic primer

<400> SEQUENCE: 74
gtgccagcmg ccgcggtaac cgtattctaa ggtacggat            39

<210> SEQ ID NO 75
<211> LENGTH: 39
<212> TYPE: DNA
<213> ORGANISM: Artificial
<220> FEATURE:
<223> OTHER INFORMATION: synthetic primer

<400> SEQUENCE: 75
gtgccagcmg ccgcggtaag cgatctaatc ttaacagac            39

<210> SEQ ID NO 76
<211> LENGTH: 39
<212> TYPE: DNA
<213> ORGANISM: Artificial
<220> FEATURE:
<223> OTHER INFORMATION: synthetic primer

<400> SEQUENCE: 76
gtgccagcmg ccgcggtaaa actgcatttc aagtccgaa            39

<210> SEQ ID NO 77
<211> LENGTH: 39
<212> TYPE: DNA
<213> ORGANISM: Artificial

```
<220> FEATURE:
<223> OTHER INFORMATION: synthetic primer

<400> SEQUENCE: 77
gtgccagcmg ccgcggtaat ctgaacttcc ctatctcca                    39

<210> SEQ ID NO 78
<211> LENGTH: 39
<212> TYPE: DNA
<213> ORGANISM: Artificial
<220> FEATURE:
<223> OTHER INFORMATION: synthetic primer

<400> SEQUENCE: 78
gtgccagcmg ccgcggtaaa agagtagagg atttcgtgt                    39

<210> SEQ ID NO 79
<211> LENGTH: 39
<212> TYPE: DNA
<213> ORGANISM: Artificial
<220> FEATURE:
<223> OTHER INFORMATION: synthetic primer

<400> SEQUENCE: 79
gtgccagcmg ccgcggtaaa ctctctaaaa tgcagtcgg                    39

<210> SEQ ID NO 80
<211> LENGTH: 39
<212> TYPE: DNA
<213> ORGANISM: Artificial
<220> FEATURE:
<223> OTHER INFORMATION: synthetic primer

<400> SEQUENCE: 80
gtgccagcmg ccgcggtaat agtgactagg gtaaatgcc                    39

<210> SEQ ID NO 81
<211> LENGTH: 39
<212> TYPE: DNA
<213> ORGANISM: Artificial
<220> FEATURE:
<223> OTHER INFORMATION: synthetic primer

<400> SEQUENCE: 81
gtgccagcmg ccgcggtaac ttacacccta cgttgctga                    39

<210> SEQ ID NO 82
<211> LENGTH: 39
<212> TYPE: DNA
<213> ORGANISM: Artificial
<220> FEATURE:
<223> OTHER INFORMATION: synthetic primer

<400> SEQUENCE: 82
gtgccagcmg ccgcggtaat tgaggttaag ttgtttgcc                    39

<210> SEQ ID NO 83
<211> LENGTH: 39
<212> TYPE: DNA
<213> ORGANISM: Artificial
<220> FEATURE:
<223> OTHER INFORMATION: synthetic primer

<400> SEQUENCE: 83
gtgccagcmg ccgcggtaag tgttaggttt tgatgaacc                    39
```

<210> SEQ ID NO 84
<211> LENGTH: 39
<212> TYPE: DNA
<213> ORGANISM: Artificial
<220> FEATURE:
<223> OTHER INFORMATION: synthetic primer

<400> SEQUENCE: 84
gtgccagcmg ccgcggtaaa aattatctgt ggattgccg                      39

<210> SEQ ID NO 85
<211> LENGTH: 39
<212> TYPE: DNA
<213> ORGANISM: Artificial
<220> FEATURE:
<223> OTHER INFORMATION: synthetic primer

<400> SEQUENCE: 85
gtgccagcmg ccgcggtaaa gatagatggt gtactgcac                      39

<210> SEQ ID NO 86
<211> LENGTH: 39
<212> TYPE: DNA
<213> ORGANISM: Artificial
<220> FEATURE:
<223> OTHER INFORMATION: synthetic primer

<400> SEQUENCE: 86
gtgccagcmg ccgcggtaaa gatgcaaata cccgggtac                      39

<210> SEQ ID NO 87
<211> LENGTH: 39
<212> TYPE: DNA
<213> ORGANISM: Artificial
<220> FEATURE:
<223> OTHER INFORMATION: synthetic primer

<400> SEQUENCE: 87
gtgccagcmg ccgcggtaat caacgtcagg caatgtgtc                      39

<210> SEQ ID NO 88
<211> LENGTH: 19
<212> TYPE: DNA
<213> ORGANISM: Artificial
<220> FEATURE:
<223> OTHER INFORMATION: synthetic primer

<400> SEQUENCE: 88
gtgccagcmg ccgcggtaa                                            19

<210> SEQ ID NO 89
<211> LENGTH: 40
<212> TYPE: DNA
<213> ORGANISM: Artificial
<220> FEATURE:
<223> OTHER INFORMATION: synthetic primer

<400> SEQUENCE: 89
ggactachvg ggtwtctaat aatgtgtcca gcagaagcag                     40

<210> SEQ ID NO 90
<211> LENGTH: 40
<212> TYPE: DNA
<213> ORGANISM: Artificial
<220> FEATURE:
<223> OTHER INFORMATION: synthetic primer

```
<400> SEQUENCE: 90
ggactachvg ggtwtctaat tgtttaagct ggactgccac                    40

<210> SEQ ID NO 91
<211> LENGTH: 40
<212> TYPE: DNA
<213> ORGANISM: Artificial
<220> FEATURE:
<223> OTHER INFORMATION: synthetic primer

<400> SEQUENCE: 91
ggactachvg ggtwtctaat actctctggc aactccccaa                    40

<210> SEQ ID NO 92
<211> LENGTH: 40
<212> TYPE: DNA
<213> ORGANISM: Artificial
<220> FEATURE:
<223> OTHER INFORMATION: synthetic primer

<400> SEQUENCE: 92
ggactachvg ggtwtctaat tggcactctc tcacagccaa                    40

<210> SEQ ID NO 93
<211> LENGTH: 40
<212> TYPE: DNA
<213> ORGANISM: Artificial
<220> FEATURE:
<223> OTHER INFORMATION: synthetic primer

<400> SEQUENCE: 93
ggactachvg ggtwtctaat acaccctccc aagtatggtg                    40

<210> SEQ ID NO 94
<211> LENGTH: 40
<212> TYPE: DNA
<213> ORGANISM: Artificial
<220> FEATURE:
<223> OTHER INFORMATION: synthetic primer

<400> SEQUENCE: 94
ggactachvg ggtwtctaat ttgtagcttt cccaccagag                    40

<210> SEQ ID NO 95
<211> LENGTH: 40
<212> TYPE: DNA
<213> ORGANISM: Artificial
<220> FEATURE:
<223> OTHER INFORMATION: synthetic primer

<400> SEQUENCE: 95
ggactachvg ggtwtctaat tttcgggaga ctggtcgctt                    40

<210> SEQ ID NO 96
<211> LENGTH: 40
<212> TYPE: DNA
<213> ORGANISM: Artificial
<220> FEATURE:
<223> OTHER INFORMATION: synthetic primer

<400> SEQUENCE: 96
ggactachvg ggtwtctaat cctggcattc tagcgtaccc                    40

<210> SEQ ID NO 97
```

```
<210> SEQ ID NO 97
<211> LENGTH: 40
<212> TYPE: DNA
<213> ORGANISM: Artificial
<220> FEATURE:
<223> OTHER INFORMATION: synthetic primer

<400> SEQUENCE: 97
ggactachvg ggtwtctaat taagaccatc acgctacggg                    40

<210> SEQ ID NO 98
<211> LENGTH: 40
<212> TYPE: DNA
<213> ORGANISM: Artificial
<220> FEATURE:
<223> OTHER INFORMATION: synthetic primer

<400> SEQUENCE: 98
ggactachvg ggtwtctaat tcgtgcaata atagtcgccc                    40

<210> SEQ ID NO 99
<211> LENGTH: 40
<212> TYPE: DNA
<213> ORGANISM: Artificial
<220> FEATURE:
<223> OTHER INFORMATION: synthetic primer

<400> SEQUENCE: 99
ggactachvg ggtwtctaat gctactggaa aaaccaccct                    40

<210> SEQ ID NO 100
<211> LENGTH: 40
<212> TYPE: DNA
<213> ORGANISM: Artificial
<220> FEATURE:
<223> OTHER INFORMATION: synthetic primer

<400> SEQUENCE: 100
ggactachvg ggtwtctaat agtggcaaaa acaggcaagc                    40

<210> SEQ ID NO 101
<211> LENGTH: 40
<212> TYPE: DNA
<213> ORGANISM: Artificial
<220> FEATURE:
<223> OTHER INFORMATION: synthetic primer

<400> SEQUENCE: 101
ggactachvg ggtwtctaat tgcttggcgt tgtcagcttc                    40

<210> SEQ ID NO 102
<211> LENGTH: 40
<212> TYPE: DNA
<213> ORGANISM: Artificial
<220> FEATURE:
<223> OTHER INFORMATION: synthetic primer

<400> SEQUENCE: 102
ggactachvg ggtwtctaat catctgattc acacagtggc                    40

<210> SEQ ID NO 103
<211> LENGTH: 40
<212> TYPE: DNA
<213> ORGANISM: Artificial
<220> FEATURE:
<223> OTHER INFORMATION: synthetic primer

<400> SEQUENCE: 103
```
ggactachvg ggtwtctaat taagcatttc ctgcccaccg          40

<210> SEQ ID NO 104
<211> LENGTH: 40
<212> TYPE: DNA
<213> ORGANISM: Artificial
<220> FEATURE:
<223> OTHER INFORMATION: synthetic primer

<400> SEQUENCE: 104
ggactachvg ggtwtctaat aagcacttaa ggacggcggt          40

<210> SEQ ID NO 105
<211> LENGTH: 40
<212> TYPE: DNA
<213> ORGANISM: Artificial
<220> FEATURE:
<223> OTHER INFORMATION: synthetic primer

<400> SEQUENCE: 105
ggactachvg ggtwtctaat aaacgatcta cgtgggaccc          40

<210> SEQ ID NO 106
<211> LENGTH: 40
<212> TYPE: DNA
<213> ORGANISM: Artificial
<220> FEATURE:
<223> OTHER INFORMATION: synthetic primer

<400> SEQUENCE: 106
ggactachvg ggtwtctaat atttgctctg ccttgaagcg          40

<210> SEQ ID NO 107
<211> LENGTH: 40
<212> TYPE: DNA
<213> ORGANISM: Artificial
<220> FEATURE:
<223> OTHER INFORMATION: synthetic primer

<400> SEQUENCE: 107
ggactachvg ggtwtctaat cgcactaaca tagtgcaggg          40

<210> SEQ ID NO 108
<211> LENGTH: 40
<212> TYPE: DNA
<213> ORGANISM: Artificial
<220> FEATURE:
<223> OTHER INFORMATION: synthetic primer

<400> SEQUENCE: 108
ggactachvg ggtwtctaat tagggtttc ccctatggac          40

<210> SEQ ID NO 109
<211> LENGTH: 40
<212> TYPE: DNA
<213> ORGANISM: Artificial
<220> FEATURE:
<223> OTHER INFORMATION: synthetic primer

<400> SEQUENCE: 109
ggactachvg ggtwtctaat tcgactagtc gggtttgggt          40

<210> SEQ ID NO 110
<211> LENGTH: 40
<212> TYPE: DNA

<213> ORGANISM: Artificial
<220> FEATURE:
<223> OTHER INFORMATION: synthetic primer

<400> SEQUENCE: 110
ggactachvg ggtwtctaat cagctaaaac ccctgcctgc     40

<210> SEQ ID NO 111
<211> LENGTH: 40
<212> TYPE: DNA
<213> ORGANISM: Artificial
<220> FEATURE:
<223> OTHER INFORMATION: synthetic primer

<400> SEQUENCE: 111
ggactachvg ggtwtctaat ggagatatga tcgttccgca     40

<210> SEQ ID NO 112
<211> LENGTH: 40
<212> TYPE: DNA
<213> ORGANISM: Artificial
<220> FEATURE:
<223> OTHER INFORMATION: synthetic primer

<400> SEQUENCE: 112
ggactachvg ggtwtctaat tctacagccg cttcacgctc     40

<210> SEQ ID NO 113
<211> LENGTH: 40
<212> TYPE: DNA
<213> ORGANISM: Artificial
<220> FEATURE:
<223> OTHER INFORMATION: synthetic primer

<400> SEQUENCE: 113
ggactachvg ggtwtctaat ccgttaaata gggaggctcg     40

<210> SEQ ID NO 114
<211> LENGTH: 40
<212> TYPE: DNA
<213> ORGANISM: Artificial
<220> FEATURE:
<223> OTHER INFORMATION: synthetic primer

<400> SEQUENCE: 114
ggactachvg ggtwtctaat ttaacaatcc tccccaaggg     40

<210> SEQ ID NO 115
<211> LENGTH: 40
<212> TYPE: DNA
<213> ORGANISM: Artificial
<220> FEATURE:
<223> OTHER INFORMATION: synthetic primer

<400> SEQUENCE: 115
ggactachvg ggtwtctaat gtaacgtgag agaatgcgac     40

<210> SEQ ID NO 116
<211> LENGTH: 40
<212> TYPE: DNA
<213> ORGANISM: Artificial
<220> FEATURE:
<223> OTHER INFORMATION: synthetic primer

<400> SEQUENCE: 116
ggactachvg ggtwtctaat ttaggccctc tgaagaaggc     40

<210> SEQ ID NO 117
<211> LENGTH: 40
<212> TYPE: DNA
<213> ORGANISM: Artificial
<220> FEATURE:
<223> OTHER INFORMATION: synthetic primer

<400> SEQUENCE: 117
ggactachvg ggtwtctaat ttggctggtt taggagtagg                           40

<210> SEQ ID NO 118
<211> LENGTH: 40
<212> TYPE: DNA
<213> ORGANISM: Artificial
<220> FEATURE:
<223> OTHER INFORMATION: synthetic primer

<400> SEQUENCE: 118
ggactachvg ggtwtctaat gaactgacat cattggggct                           40

<210> SEQ ID NO 119
<211> LENGTH: 40
<212> TYPE: DNA
<213> ORGANISM: Artificial
<220> FEATURE:
<223> OTHER INFORMATION: synthetic primer

<400> SEQUENCE: 119
ggactachvg ggtwtctaat agtttgacct cagcgccatg                           40

<210> SEQ ID NO 120
<211> LENGTH: 40
<212> TYPE: DNA
<213> ORGANISM: Artificial
<220> FEATURE:
<223> OTHER INFORMATION: synthetic primer

<400> SEQUENCE: 120
ggactachvg ggtwtctaat tagtcgttcg ctccggcatc                           40

<210> SEQ ID NO 121
<211> LENGTH: 40
<212> TYPE: DNA
<213> ORGANISM: Artificial
<220> FEATURE:
<223> OTHER INFORMATION: synthetic primer

<400> SEQUENCE: 121
ggactachvg ggtwtctaat ttcagtgact gtgagatgcc                           40

<210> SEQ ID NO 122
<211> LENGTH: 40
<212> TYPE: DNA
<213> ORGANISM: Artificial
<220> FEATURE:
<223> OTHER INFORMATION: synthetic primer

<400> SEQUENCE: 122
ggactachvg ggtwtctaat acgacctata tcagccgacg                           40

<210> SEQ ID NO 123
<211> LENGTH: 40
<212> TYPE: DNA
<213> ORGANISM: Artificial
<220> FEATURE:

<223> OTHER INFORMATION: synthetic primer

<400> SEQUENCE: 123
ggactachvg ggtwtctaat accagttggg agggaggtct          40

<210> SEQ ID NO 124
<211> LENGTH: 40
<212> TYPE: DNA
<213> ORGANISM: Artificial
<220> FEATURE:
<223> OTHER INFORMATION: synthetic primer

<400> SEQUENCE: 124
ggactachvg ggtwtctaat ggcgaggtca tcatacgctg          40

<210> SEQ ID NO 125
<211> LENGTH: 40
<212> TYPE: DNA
<213> ORGANISM: Artificial
<220> FEATURE:
<223> OTHER INFORMATION: synthetic primer

<400> SEQUENCE: 125
ggactachvg ggtwtctaat cgatacggtc taactcgcgt          40

<210> SEQ ID NO 126
<211> LENGTH: 40
<212> TYPE: DNA
<213> ORGANISM: Artificial
<220> FEATURE:
<223> OTHER INFORMATION: synthetic primer

<400> SEQUENCE: 126
ggactachvg ggtwtctaat ctgctccaac tactggggct          40

<210> SEQ ID NO 127
<211> LENGTH: 40
<212> TYPE: DNA
<213> ORGANISM: Artificial
<220> FEATURE:
<223> OTHER INFORMATION: synthetic primer

<400> SEQUENCE: 127
ggactachvg ggtwtctaat ctctgctcca tccctccaac          40

<210> SEQ ID NO 128
<211> LENGTH: 40
<212> TYPE: DNA
<213> ORGANISM: Artificial
<220> FEATURE:
<223> OTHER INFORMATION: synthetic primer

<400> SEQUENCE: 128
ggactachvg ggtwtctaat tggctcatat cagtgcagca          40

<210> SEQ ID NO 129
<211> LENGTH: 40
<212> TYPE: DNA
<213> ORGANISM: Artificial
<220> FEATURE:
<223> OTHER INFORMATION: synthetic primer

<400> SEQUENCE: 129
ggactachvg ggtwtctaat aatggccggt taacgcactc          40

```
<210> SEQ ID NO 130
<211> LENGTH: 40
<212> TYPE: DNA
<213> ORGANISM: Artificial
<220> FEATURE:
<223> OTHER INFORMATION: synthetic primer

<400> SEQUENCE: 130
ggactachvg ggtwtctaat caagctattt cgatcgcgtg                         40

<210> SEQ ID NO 131
<211> LENGTH: 40
<212> TYPE: DNA
<213> ORGANISM: Artificial
<220> FEATURE:
<223> OTHER INFORMATION: synthetic primer

<400> SEQUENCE: 131
ggactachvg ggtwtctaat ttgcatgtaa cgcccaccac                         40

<210> SEQ ID NO 132
<211> LENGTH: 40
<212> TYPE: DNA
<213> ORGANISM: Artificial
<220> FEATURE:
<223> OTHER INFORMATION: synthetic primer

<400> SEQUENCE: 132
ggactachvg ggtwtctaat caagaatgaa gtagtgcggg                         40

<210> SEQ ID NO 133
<211> LENGTH: 40
<212> TYPE: DNA
<213> ORGANISM: Artificial
<220> FEATURE:
<223> OTHER INFORMATION: synthetic primer

<400> SEQUENCE: 133
ggactachvg ggtwtctaat ttggtggaag ccgtatgctc                         40

<210> SEQ ID NO 134
<211> LENGTH: 40
<212> TYPE: DNA
<213> ORGANISM: Artificial
<220> FEATURE:
<223> OTHER INFORMATION: synthetic primer

<400> SEQUENCE: 134
ggactachvg ggtwtctaat ccgataagaa gcgctcccac                         40

<210> SEQ ID NO 135
<211> LENGTH: 40
<212> TYPE: DNA
<213> ORGANISM: Artificial
<220> FEATURE:
<223> OTHER INFORMATION: synthetic primer

<400> SEQUENCE: 135
ggactachvg ggtwtctaat gccgagcctc tttatccagc                         40

<210> SEQ ID NO 136
<211> LENGTH: 40
<212> TYPE: DNA
<213> ORGANISM: Artificial
<220> FEATURE:
<223> OTHER INFORMATION: synthetic primer
```

<400> SEQUENCE: 136
ggactachvg ggtwtctaat tttaccgatg agaaacgccc                    40

<210> SEQ ID NO 137
<211> LENGTH: 40
<212> TYPE: DNA
<213> ORGANISM: Artificial
<220> FEATURE:
<223> OTHER INFORMATION: synthetic primer

<400> SEQUENCE: 137
ggactachvg ggtwtctaat tccgagtaca tagaggcgac                    40

<210> SEQ ID NO 138
<211> LENGTH: 40
<212> TYPE: DNA
<213> ORGANISM: Artificial
<220> FEATURE:
<223> OTHER INFORMATION: synthetic primer

<400> SEQUENCE: 138
ggactachvg ggtwtctaat gatcagactt cgcgtcgacg                    40

<210> SEQ ID NO 139
<211> LENGTH: 40
<212> TYPE: DNA
<213> ORGANISM: Artificial
<220> FEATURE:
<223> OTHER INFORMATION: synthetic primer

<400> SEQUENCE: 139
ggactachvg ggtwtctaat ctatagccct ccacccgctc                    40

<210> SEQ ID NO 140
<211> LENGTH: 40
<212> TYPE: DNA
<213> ORGANISM: Artificial
<220> FEATURE:
<223> OTHER INFORMATION: synthetic primer

<400> SEQUENCE: 140
ggactachvg ggtwtctaat tagtcatgcg tatgcgcttc                    40

<210> SEQ ID NO 141
<211> LENGTH: 40
<212> TYPE: DNA
<213> ORGANISM: Artificial
<220> FEATURE:
<223> OTHER INFORMATION: synthetic primer

<400> SEQUENCE: 141
ggactachvg ggtwtctaat gcataactcc tacacggtgg                    40

<210> SEQ ID NO 142
<211> LENGTH: 40
<212> TYPE: DNA
<213> ORGANISM: Artificial
<220> FEATURE:
<223> OTHER INFORMATION: synthetic primer

<400> SEQUENCE: 142
ggactachvg ggtwtctaat ccgtaatgag gaatttgcgg                    40

<210> SEQ ID NO 143
<211> LENGTH: 40

```
<212> TYPE: DNA
<213> ORGANISM: Artificial
<220> FEATURE:
<223> OTHER INFORMATION: synthetic primer

<400> SEQUENCE: 143
ggactachvg ggtwtctaat cgaaggggc agagtagacg                    40

<210> SEQ ID NO 144
<211> LENGTH: 40
<212> TYPE: DNA
<213> ORGANISM: Artificial
<220> FEATURE:
<223> OTHER INFORMATION: synthetic primer

<400> SEQUENCE: 144
ggactachvg ggtwtctaat gcacttacct ggagagaagg                   40

<210> SEQ ID NO 145
<211> LENGTH: 40
<212> TYPE: DNA
<213> ORGANISM: Artificial
<220> FEATURE:
<223> OTHER INFORMATION: synthetic primer

<400> SEQUENCE: 145
ggactachvg ggtwtctaat gcgaagcgat accctacgct                   40

<210> SEQ ID NO 146
<211> LENGTH: 40
<212> TYPE: DNA
<213> ORGANISM: Artificial
<220> FEATURE:
<223> OTHER INFORMATION: synthetic primer

<400> SEQUENCE: 146
ggactachvg ggtwtctaat ccttgtaagc tacgcccaga                   40

<210> SEQ ID NO 147
<211> LENGTH: 40
<212> TYPE: DNA
<213> ORGANISM: Artificial
<220> FEATURE:
<223> OTHER INFORMATION: synthetic primer

<400> SEQUENCE: 147
ggactachvg ggtwtctaat ggatgaacca acatctgcct                   40

<210> SEQ ID NO 148
<211> LENGTH: 40
<212> TYPE: DNA
<213> ORGANISM: Artificial
<220> FEATURE:
<223> OTHER INFORMATION: synthetic primer

<400> SEQUENCE: 148
ggactachvg ggtwtctaat tcttgcgtta acggtttccg                   40

<210> SEQ ID NO 149
<211> LENGTH: 40
<212> TYPE: DNA
<213> ORGANISM: Artificial
<220> FEATURE:
<223> OTHER INFORMATION: synthetic primer

<400> SEQUENCE: 149
```

```
ggactachvg ggtwtctaat cgtcgtcctc aaatttcgca                    40
```

<210> SEQ ID NO 150
<211> LENGTH: 40
<212> TYPE: DNA
<213> ORGANISM: Artificial
<220> FEATURE:
<223> OTHER INFORMATION: synthetic primer

<400> SEQUENCE: 150

```
ggactachvg ggtwtctaat aacctctggg tttaagccga                    40
```

<210> SEQ ID NO 151
<211> LENGTH: 40
<212> TYPE: DNA
<213> ORGANISM: Artificial
<220> FEATURE:
<223> OTHER INFORMATION: synthetic primer

<400> SEQUENCE: 151

```
ggactachvg ggtwtctaat attcacgaaa tgctcctcgc                    40
```

<210> SEQ ID NO 152
<211> LENGTH: 40
<212> TYPE: DNA
<213> ORGANISM: Artificial
<220> FEATURE:
<223> OTHER INFORMATION: synthetic primer

<400> SEQUENCE: 152

```
ggactachvg ggtwtctaat acggaatcct ttgacgggat                    40
```

<210> SEQ ID NO 153
<211> LENGTH: 40
<212> TYPE: DNA
<213> ORGANISM: Artificial
<220> FEATURE:
<223> OTHER INFORMATION: synthetic primer

<400> SEQUENCE: 153

```
ggactachvg ggtwtctaat acgacgtgaa ttcgagggct                    40
```

<210> SEQ ID NO 154
<211> LENGTH: 40
<212> TYPE: DNA
<213> ORGANISM: Artificial
<220> FEATURE:
<223> OTHER INFORMATION: synthetic primer

<400> SEQUENCE: 154

```
ggactachvg ggtwtctaat ttagtggtgt tccagcctct                    40
```

<210> SEQ ID NO 155
<211> LENGTH: 40
<212> TYPE: DNA
<213> ORGANISM: Artificial
<220> FEATURE:
<223> OTHER INFORMATION: synthetic primer

<400> SEQUENCE: 155

```
ggactachvg ggtwtctaat gtctatcacg agatcaggca                    40
```

<210> SEQ ID NO 156
<211> LENGTH: 40
<212> TYPE: DNA
<213> ORGANISM: Artificial

<220> FEATURE:
<223> OTHER INFORMATION: synthetic primer

<400> SEQUENCE: 156
ggactachvg ggtwtctaat gtctatcacg agatcaggca          40

<210> SEQ ID NO 157
<211> LENGTH: 40
<212> TYPE: DNA
<213> ORGANISM: Artificial
<220> FEATURE:
<223> OTHER INFORMATION: synthetic primer

<400> SEQUENCE: 157
ggactachvg ggtwtctaat tggatcgagg tcatgactgg          40

<210> SEQ ID NO 158
<211> LENGTH: 40
<212> TYPE: DNA
<213> ORGANISM: Artificial
<220> FEATURE:
<223> OTHER INFORMATION: synthetic primer

<400> SEQUENCE: 158
ggactachvg ggtwtctaat ggactcgagc ctatttccca          40

<210> SEQ ID NO 159
<211> LENGTH: 40
<212> TYPE: DNA
<213> ORGANISM: Artificial
<220> FEATURE:
<223> OTHER INFORMATION: synthetic primer

<400> SEQUENCE: 159
ggactachvg ggtwtctaat gagcaggtga agtacgctca          40

<210> SEQ ID NO 160
<211> LENGTH: 40
<212> TYPE: DNA
<213> ORGANISM: Artificial
<220> FEATURE:
<223> OTHER INFORMATION: synthetic primer

<400> SEQUENCE: 160
ggactachvg ggtwtctaat gaggggtaga cgccaggtct          40

<210> SEQ ID NO 161
<211> LENGTH: 40
<212> TYPE: DNA
<213> ORGANISM: Artificial
<220> FEATURE:
<223> OTHER INFORMATION: synthetic primer

<400> SEQUENCE: 161
ggactachvg ggtwtctaat ctttacgggc caccaggaac          40

<210> SEQ ID NO 162
<211> LENGTH: 40
<212> TYPE: DNA
<213> ORGANISM: Artificial
<220> FEATURE:
<223> OTHER INFORMATION: synthetic primer

<400> SEQUENCE: 162
ggactachvg ggtwtctaat gtgtcaatga aaggagagcg          40

<210> SEQ ID NO 163
<211> LENGTH: 40
<212> TYPE: DNA
<213> ORGANISM: Artificial
<220> FEATURE:
<223> OTHER INFORMATION: synthetic primer

<400> SEQUENCE: 163
ggactachvg ggtwtctaat gacatccgca acaatgtacc                    40

<210> SEQ ID NO 164
<211> LENGTH: 40
<212> TYPE: DNA
<213> ORGANISM: Artificial
<220> FEATURE:
<223> OTHER INFORMATION: synthetic primer

<400> SEQUENCE: 164
ggactachvg ggtwtctaat ggcgtagtac gggaagaggg                    40

<210> SEQ ID NO 165
<211> LENGTH: 40
<212> TYPE: DNA
<213> ORGANISM: Artificial
<220> FEATURE:
<223> OTHER INFORMATION: synthetic primer

<400> SEQUENCE: 165
ggactachvg ggtwtctaat attgtctgca acaagggcca                    40

<210> SEQ ID NO 166
<211> LENGTH: 40
<212> TYPE: DNA
<213> ORGANISM: Artificial
<220> FEATURE:
<223> OTHER INFORMATION: synthetic primer

<400> SEQUENCE: 166
ggactachvg ggtwtctaat agcgtgcaac tagagggtcg                    40

<210> SEQ ID NO 167
<211> LENGTH: 40
<212> TYPE: DNA
<213> ORGANISM: Artificial
<220> FEATURE:
<223> OTHER INFORMATION: synthetic primer

<400> SEQUENCE: 167
ggactachvg ggtwtctaat tagaccagac ccaagagggg                    40

<210> SEQ ID NO 168
<211> LENGTH: 40
<212> TYPE: DNA
<213> ORGANISM: Artificial
<220> FEATURE:
<223> OTHER INFORMATION: synthetic primer

<400> SEQUENCE: 168
ggactachvg ggtwtctaat cctaaaccca aaagtcgggt                    40

<210> SEQ ID NO 169
<211> LENGTH: 40
<212> TYPE: DNA
<213> ORGANISM: Artificial
<220> FEATURE:
<223> OTHER INFORMATION: synthetic primer

```
<400> SEQUENCE: 169
ggactachvg ggtwtctaat aggcgaactc ggaaactcgc                              40

<210> SEQ ID NO 170
<211> LENGTH: 40
<212> TYPE: DNA
<213> ORGANISM: Artificial
<220> FEATURE:
<223> OTHER INFORMATION: synthetic primer

<400> SEQUENCE: 170
ggactachvg ggtwtctaat atggggtcaa gacacctagc                              40

<210> SEQ ID NO 171
<211> LENGTH: 40
<212> TYPE: DNA
<213> ORGANISM: Artificial
<220> FEATURE:
<223> OTHER INFORMATION: synthetic primer

<400> SEQUENCE: 171
ggactachvg ggtwtctaat ctaactcaac agacggaccc                              40

<210> SEQ ID NO 172
<211> LENGTH: 20
<212> TYPE: DNA
<213> ORGANISM: Artificial
<220> FEATURE:
<223> OTHER INFORMATION: synthetic primer

<400> SEQUENCE: 172
ggactachvg ggtwtctaat                                                    20
```

METHODS FOR VALIDATION OF MICROBIOME SEQUENCE PROCESSING AND DIFFERENTIAL ABUNDANCE ANALYSES VIA MULTIPLE BESPOKE SPIKE-IN MIXTURES

CROSS-REFERENCE TO RELATED APPLICATIONS

This application claims priority to U.S. Provisional Application Ser. No. 62/735,374, filed on Sep. 24, 2018.

BACKGROUND

Several organisms (e.g. humans, animals, plants) exist in a symbiotic relationship with microbes. For example, a human body can include more than 100 trillion microbes. Environmental ecosystems such as soil samples also include a rich repertoire of microbial communities that form a significant portion of their ecosystem. A microbiome describes the collective genomes of the microorganisms that reside in an environmental niche.

As an example, while the human genome may include about 25,000 human genes, the human body also includes more than 10 million bacterial genes, with an estimated 30% of molecules in the blood stream coming from gut bacteria. The symbiotic relationship of the human body with bacteria relates to the unique ability of microbial populations to impact human health and wellness through profound biological effects on human bodies, including immune regulation, energy biogenesis, neurologic signaling, infectious control, vitamin, amino acid and dietary component synthesis to name a few. Similarly, the composition or relative abundance of various microbial communities in environmental sources such as soil samples impact the immediate environment and the larger ecosystem dependent on the sources. Thus analysis of the relative abundance of microbial communities in both environmental and human samples is highly informative and an area of interest.

SUMMARY

This disclosure relates to compositions and methods to provide validation of methods targeted to process microbiome nucleic acid sequences and to analyze differential abundance of various microbial strains in a tested sample. This disclosure also relates to the generation of multiple bespoke spike-in mixes configured for validation of microbiome sequence processing and differential abundance analyses.

In some embodiments, provided herein is a composition, comprising: a set of n tubes (wherein "n" is the number of tubes), each tube containing a spike mix wherein the spike mix includes m polynucleotide sequences (wherein "m" is the number of polynucleotide sequences), wherein all n tubes contain the same set of m polynucleotide sequences, each of the m polynucleotide sequences being present in each of the n tubes at a copy number from a set of copy numbers, the set of copy numbers including levels selected from high, low, or ultralow, wherein the level high is greater than 1000 copies per reaction unit, the level low is 50-1000 copies per reaction unit and ultralow is less than 50 copies per reaction unit.

In some embodiments, provided herein is a composition, comprising: a set of 3 tubes, each containing a spike mix wherein the spike mix comprises 69 template polynucleotide sequences, wherein all 3 tubes contain the same set of 69 template polynucleotide sequences, each of the 69 template polynucleotide sequences is present in each of the 3 spike mix tubes at a copy number of high, low, or ultralow, wherein high is greater than 1000 copies per reaction unit, low is 50-1000 copies per reaction unit and ultralow is less than 50 copies per reaction unit, each of the 69 template polynucleotide sequences comprises, in a 5' to 3' direction, a nucleotide sequence that will anneal to a first end of a marker gene (e.g., a forward primer sequence) during a PCR amplification reaction, a negative control nucleotide sequence which will not anneal to the marker gene during the PCR amplification reaction, and a nucleotide sequence that will anneal to a second end of the marker gene (e.g., a reverse primer sequence) during the PCR amplification reaction. In some embodiments, each of the negative control nucleotide sequences is different from the other 68 marker gene sequences. In some embodiments, (a) the copy number of each of the 69 polynucleotide sequences in the 3 tubes is the same in all 3 tubes (high/high/high; low/low/low; ultralow/ultralow/ultralow), (b) the copy number is different in all 3 tubes (high/low/ultralow; high/ultralow/low; low/high/ultralow; low/ultralow/high; ultralow/low/high; or ultralow/high/low), or (c) the copy number is the same in 2 of the 3 tubes (high/high/low; high/high/ultralow, etc. . . . ). In some embodiments, the marker gene is any gene that is conserved among the organisms being surveyed such that a universal primer set can be designed to anneal to 5' and 3' ends for PCR amplification from a sample. In some embodiments, the marker gene is a prokaryotic, eukaryotic, or viral gene. In some embodiments, the marker gene is selected from the group consisting of 16S rRNA, the V1, V2, V3, V4, V5, V6, V7, V8 and/or V9 regions of 16S rRNA, 18S rRNA.

In some embodiments, provided herein is a method for determining the number of microbes in a sample, the method comprising: isolating genomic DNA from the sample, performing a PCR reaction to amplify a marker gene sequence, wherein the marker gene sequence is present in the microbes and wherein the PCR reaction is performed in the presence of the composition of any one of compositions above such that the sample is divided among a plurality of reaction vessels and each of the plurality of reaction vessels contains one of the 3 spike mixes.

In some embodiments, provided herein is a processor-implemented method of determining and providing confidence estimates for differential abundance analyses of a microbiome, comprising: receiving sequence data, the sequence data including data related to the microbiome and the sequence data further including data related to a set of polynucleotide spike-mixes with known template spike sequences; computing a measure of sequence similarity from the sequence data; organizing the sequence data into one or more units based on a measure of sequence similarity; performing a statistical analysis to obtain a set of calculated differential abundance estimates of the one or more units, the calculated differential abundance estimates including calculated estimates relating to the microbiome and calculated estimates relating to the polynucleotide spike-mixes with known template spike sequences; computing expected differential abundance estimates relating to the polynucleotide spike-mixes with known template spike sequences; comparing the expected differential abundance estimates relating to the polynucleotide spike-mixes with the calculated differential abundance estimates relating to the polynucleotide spike-mixes; computing, based on the comparing, a measure of confidence associated with the calculated estimates relating to the polynucleotide spike-mixes with known template spike sequences; and providing the measure of confidence as a confidence estimate for the differential abundance analyses of the microbiome. In some embodiments, the method further comprises categorizing the expected differential abundance estimates and the calculated differential abundance estimates relating to the polynucleotide spike-mixes with known template spike sequences based on a measure of relative abundance of each template spike included in the polynucleotide spike-mix; the comparing further including comparing the expected differential abundance estimates relating to the polynucleotide spike-mixes in each category with the calculated differential abundance estimates relating to the polynucleotide spike-mixes in the same category; wherein computing the measure of confidence includes computing a unique measure of confidence associated with each category of differential abundance estimates. In some embodiments, the set of polynucleotide spike-mixes with known template spike sequences are configured such that all polynucleotide spike mix include the same set of template spike sequences, the polynucleotide spike-mixes being further configured such that each polynucleotide spike mix includes a first subset of the set of template spike sequences with a copy number that is the same as the copy number of that first subset of template spike sequence in the remaining polynucleotide spike mixes; each polynucleotide spike mix includes a second subset of the set of template spike sequences with a copy number that is different from the copy number of that second subset of template spike sequence in at least one of the remaining polynucleotide spike mixes, the difference in copy number being approximately one order of magnitude; and each polynucleotide spike mix includes a third subset of the set of template spike sequences with a copy number that is different from the copy number of that third subset of template spike sequence in at least one of the remaining polynucleotide spike mixes, the difference in copy number being more than one order of magnitude. In some embodiments, the organizing the sequence data into one or more units includes clustering the sequence data into operational taxonomic units. In some embodiments, the organizing the sequence data into one or more units includes mapping the sequence data against a reference database of sequences. In some embodiments, the organizing the sequence data into one or more units includes implementing one or more methods of error-correction such that the units are defined based on a set of amplicon sequence variants. In some embodiments, the performing the statistical analysis includes hypothesis testing using the organized sequence data.

In some embodiments, provided herein is a processor-implemented method of evaluating workflow pipelines, comprising: using the polynucleotide spike-mixes to generate measures or metrics of performance; calculating a final pipeline ranking metric; and selecting a workflow pipeline to be used in a study of research protocol based on the calculation of the final pipeline ranking metric. In some embodiments, the final pipeline ranking metric is calculated as (theta_normalized/2)+(sigma_normalized/2)+detect_rate+Sensitivity+Specificity+Accuracy+Precision+Spk16_PPV*1.5−(FalsePos16S_Rate+FalseNeg_rate). In some embodiments, the final ranking metric can be used to select a workflow pipeline to be used in a study sensitive to accuracy and detection.

In some embodiments, provided herein is a method of determining validity of an analysis result of a biological sample, the method comprising: mixing the biological sample with a spike mix; amplifying one or more target sequences in the biological sample and the spike mix, thereby obtaining amplified products; sequencing and processing the amplified products; and determining a statistical measure for one or more target sequences in the spike mix, thereby inferring the validity of the analysis result for the biological sample. In some embodiments, the biological sample is a blood sample, a tissue sample, a skin sample, a urine sample, or a stool sample. In some embodiments, the biological sample is a stool sample.

In some embodiments, provided herein is a method of determining validity of an analysis result of an environmental sample, the method comprising: mixing the environmental sample with a spike mix; amplifying one or more target sequences in the environmental sample and the spike mix, thereby obtaining amplified products; sequencing and processing the amplified products; and determining a statistical measure for one or more target sequences in the spike mix, thereby inferring the validity of the analysis result for the environmental sample. In some embodiments, the environmental sample is a soil sample or a water sample.

BRIEF DESCRIPTION OF THE DRAWINGS

FIGS. 3A, 3B, and 3C are schematic representations of an example template polynucleotide sequence that can be used as a spike in validating sequence processing methods using a DAA system according to an embodiment.

FIG. 8C is a table listing classes of template spikes categorized by levels of expected abundance.

FIGS. 10A and 10B are an example truth tables generated to evaluate the accuracy of detection of a disease condition based on differential abundance analyses, using a DAA system according to an embodiment.

FIG. 18B is a table indicating classes of template spikes categorized by levels of relative abundance and the corresponding positive predictive value calculated using various pipelines for differential abundance analyses.

FIGS. 22A and 22B are tables representing results from evaluating pipelines for differential abundance analyses, quantified by a ranking score, using a DAA system according to an embodiment.

DETAILED DESCRIPTION

Systems, methods and apparatuses of the disclosure relate to providing validation for sequence processing methods and workflow pipelines used for differential abundance analyses of high-throughput sequencing data for example data obtained from PCR amplified samples. Methods and apparatus disclosed herein also relate to predicting and providing confidence or error estimates associated with differential abundance analyses conducted to test of aberrant or deviant conditions (e.g. disease conditions) associated with the sample sources.

Figure 1:
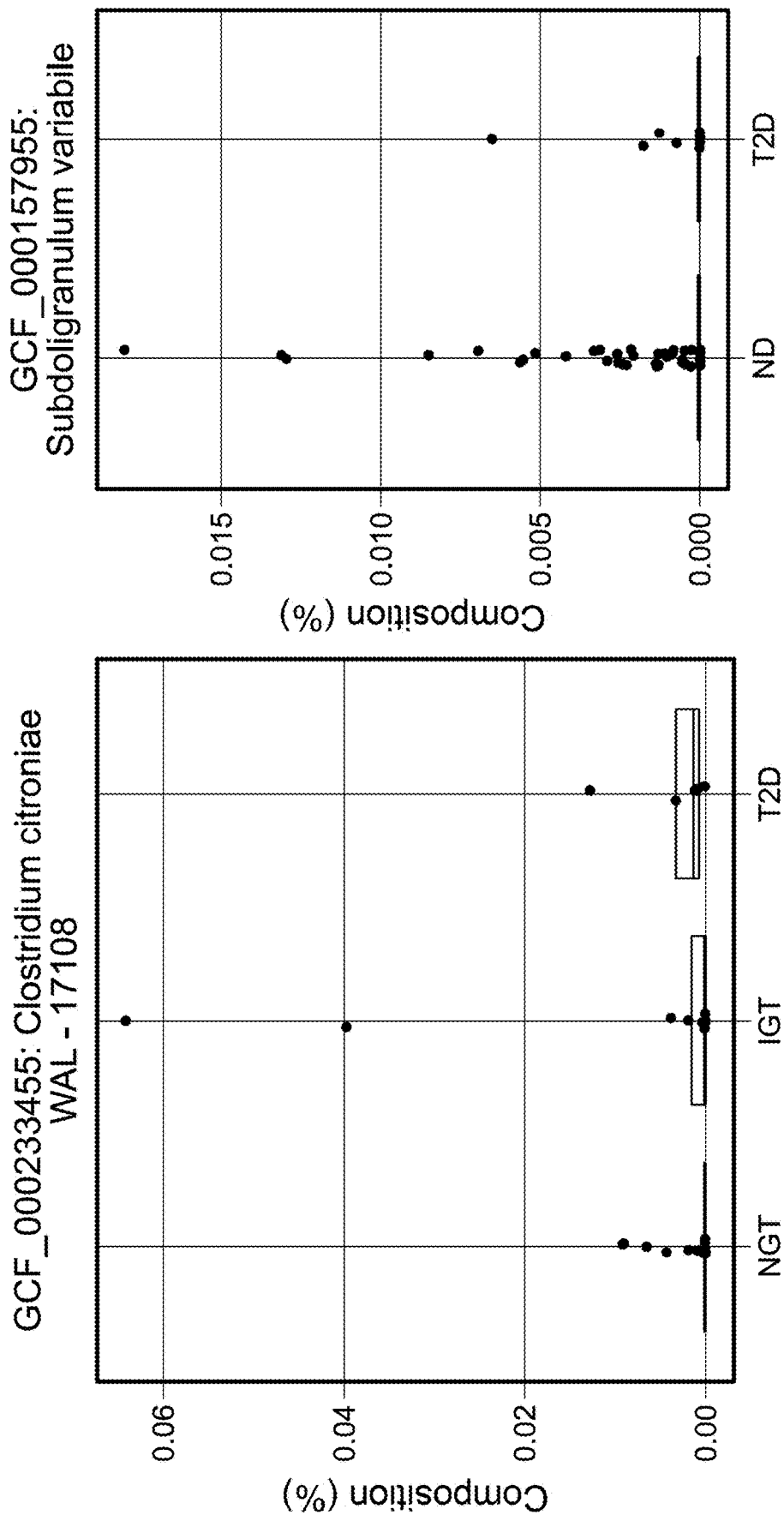
FIG. 1 shows example plots of results of currently available methods of sequence processing illustrating problems associated with sparse data.

Marker gene-based next generation sequencing surveys of microbiomes associated with humans, animals, plants and soil have led to a dramatic increase in our understanding of the role of these communities in host health. A key focal point in the context of human health has been the gut microbiome, where many studies have explored correlations between diet, antibiotics, genetic and environmental factors, immune function and the microbiome. For example, recent studies have identified gut microbes that delineate responder and non-responder populations in melanoma patients undergoing checkpoint-inhibitor therapy. Furthermore, gut microbiome dysbiosis has been implicated in disorders such as Inflammatory Bowel Disease, NASH and other metabolic disorders. Such dysbiosis is typically characterized by a decrease in gut microbiome diversity, increase in abundance of opportunistic pathogens or decrease in functionally important bacteria such as butyrate producers. For example, analyses of composition of gut microbiome can serve a vital role in diagnosis and/or treatment. However, sparsity of data can lead to problematic conclusions due to lack of statistical power and/or confidence as estimates without any other source of validation. FIG. 1 illustrates an example set of results from sparse data indicating composition estimates of two example microbial communities from sources with various health conditions such as normal glucose tolerance (NGT), impaired glucose tolerance (IGT), and Type II Diabetes (T2D), and normal population compared to patients of T2D. Furthermore, current methods of differential abundance analyses of microbiomes create challenges for the rigorous cross-study analyses. There is a need for validation methods that can be used to evaluate results from sparse or noisy data, and to compare and use cross-study data to arrive at more rigorous conclusions.

Analysis of Microbial Community Compositions

The 16S rRNA gene has emerged as a widely used marker gene for analysis of bacterial community composition because of its ubiquitous presence in the bacterial and archaeal domains. Conserved regions flanking the nine hypervariable regions of the 16S rRNA gene enable PCR-amplification of one or more hypervariable regions. Each region contains sufficient sequence diversity to allow for differentiation of bacterial taxa, although the level of taxonomic resolution depend on the targeted hypervariable region(s). Typical goals with 16S rRNA gene-based studies are to accurately determine the number and taxonomic annotation of members within a community and variation in community composition across samples. However, determining the exact composition and structure of microbiomes is challenging because of the vast number of bacterial taxa, the multitude of interactions between community members, the host and the environment and the volume of data generated in such marker gene surveys.

Inference of microbial community composition is influenced by choice of bioinformatics pipeline: Sequence processing pipelines, such as mother (Schloss, P. D., et al. (2009). Introducing mothur: Open-source, platform-independent, community-supported software for describing and comparing microbial communities. *Applied and Environmental Microbiology*, 75(23), 7537-7541. doi.org/10.1128/AEM.01541-09) and QIIME (Caporaso, J. G., et al. (2010). QIIME allows analysis of high-throughput community sequencing data. *Nature Methods*, 7(5), 335-336. doi.org/10.1038/nmeth.f.303), allow processing of sequenced reads based on quality, clustering similar sequences into Operational Taxonomic Units (OTUs) at a defined percentage similarity and assigning taxonomic annotations to OTU clusters or reads. While OTU clustering reduces the noise associated with propagation of sequencing errors, low-abundance spurious sequences resulting from sequencing errors could be interpreted as biologically meaningful OTUs thereby inflating the richness and diversity in the community.

While, the 97% similarity cut-off typically used for clustering OTUs is expected to approximate species-level clustering, it may place phylogenetically distinct species into the same cluster resulting in loss of fine-scale variation between communities. As 16S rRNA gene-survey studies grow, an important drawback with clustering OTUs based on a defined percentage similarity is the inability to compare OTUs across studies without significant re-analysis. While OTU-picking strategies that generate clusters by mapping sequences to a reference database partially circumvent this caveat and enable meta-analysis across studies, information on true biological sequences without a match in the database are lost.

Methods based on denoising algorithms such as DADA2 (Callahan, B. J., et al. (2016). DADA2: High-resolution sample inference from Illumina amplicon data. *Nature Methods*, 13(7), 581-583. doi.org/10.1038/nmeth.3869), Deblur (Amir A, et al. 2017. Deblur rapidly resolves single-nucleotide community sequence patterns. *mSystems* 2:e00191-16.doi.org/10.1128/mSystems.00191-16), UNOISE2 (Edgar, R. C. (2016). UNOISE2: improved error-correction for Illumina 16S and ITS amplicon sequencing. *bioRxiv*. doi.org/10.1101/081257), and SeekDeep (Hathaway, N. J., et al. (2018). SeekDeep: single-base resolution de novo clustering for amplicon deep sequencing. *Nucleic Acids Research*, 46(4), e21-e21. doi.org/10.1093/nar/gkx1201) have enabled inference of Amplicon Sequence Variants (ASVs) from Illumina sequence data by correcting for sequencing errors. DADA2, for example, infers ASVs by constructing a sequence quality error model and partitioning reads that are consistent with the error model into ASVs. These methods offer a reference-free strategy for inferring sequence variants and also enable cross-study meta-analysis since ASVs are representative of putatively true biological sequences. Furthermore, these methods have been shown to be able to accurately capture single-nucleotide variations which could be critical when identifying keystone microbiota differentiating health and disease.

Normalization, to account for the variation in sequence depth across samples which can be observed over several orders of magnitude, becomes important to make any cross-sample comparisons. While total sum normalization (TSS) enables comparison of compositional data across samples, standard statistics fails to be applicable to TSS-normalized data since relative abundance of taxa sum to one. On the other hand, rarefying datasets to an even depth results in a loss of data and precision. Statistical methods for testing differential abundance of taxa such as DESeq2 (Love, M. I., et al. (2014). Moderated estimation of fold change and dispersion for RNA-seq data with DESeq2. *Genome Biology*, 15(12), 550. doi.org/10.1186/s13059-014-0550-8), MetagenomeSeq (Paulson, J. N., et al. (2013). Differential abundance analysis for microbial marker-gene surveys. *Nature Methods*, 10(12), 1200-1202. doi.org/10.1038/nmeth.2658), EdgeR (Robinson, M. D., et al. (2009). edgeR: A Bioconductor package for differential expression analysis of digital gene expression data. *Bioinformatics*, 26(1), 139-140. doi.org/10.1093/bioinformatics/btp616), and Voom (Law, C. W., et al. (2014). voom: precision weights unlock linear model analysis tools for RNA-seq read counts. *Genome Biology*, 15(2), R29. doi.org/10.1186/gb-2014-15-2-r29) overcome challenges of non-normality and uneven sequencing depth of marker-gene datasets by making some distributional assumption of the data and employing parametric statistical tests. These methods eliminate the need for normalization or rarefaction and also offer robust statistics for detection of significant differences despite the sparsity (excess zeros) and undersampling prevalent in microbiome datasets.

Complexities with inference of community composition also arise from technical variations in the sequencing process from extraction, amplification and sequencing and in determining the accuracy of base calls from the sequencer. While bioinformatics tools enable reduction of some intrinsic errors associated with sequencing, technical variations and poor reproducibility of microbiome datasets pose challenges with identification of cross-study trends.

Validating Relative Abundance Estimations of Microbial Communities

Internal standards developed for RNAseq, RNA microarrays, and 16S rRNA gene experiments enable assessment of the sensitivity, reproducibility and accuracy in abundance estimation of transcript or marker genes. Low complexity mock communities, such as the equimolar or staggered mixture of genomic DNA from 21 bacterial strains developed by the Human Microbiome Consortium, have been routinely used in benchmarking wet lab and bioinformatics pipelines.

Embodiments disclosed herein include compositions, methods and systems used to develop and apply a series of microbiome control standard mixes consisting of 69 unique templates, sourced from NIST standard reference materials. In some embodiments, the series of microbiome control standard mixes consisting of 69 unique templates are sourced from NIST standard reference materials across six orders of magnitude. Three unique mixes, also referred to herein as "spike mixes" or "internal spike-in standards" or "quantitative microbiome sequencing tracers", each mix including varying abundances of all 69 template spikes over 21 different levels. Described herein is an example demonstration of addition of internal spike-in standards and their evaluation which can yield important insights into the accuracy and the limitations of bioinformatics pipelines in estimating significant differential abundance of 16S rRNA gene sequences. The example demonstration illustrates an example use of the spike mixes to identify and benchmark a bioinformatics pipeline that would provide high fidelity in identifying significantly differentially abundant taxa and also facilitate cross study meta-analysis. The example demonstration also illustrates an example use of the spike mixes to validate significance of results obtained from differential abundance analyses for example by providing predicted confidence or error estimates based on levels of abundance.

A Differential Abundance Analysis System

Figure 2:
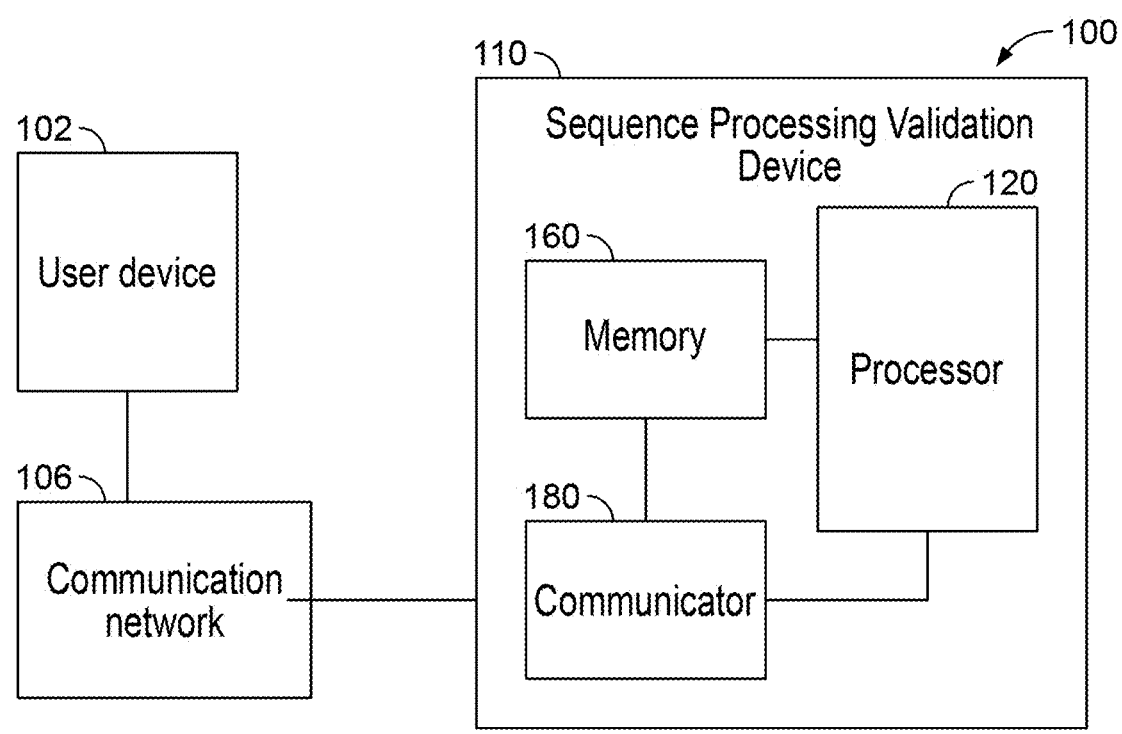
FIG. 2 is a schematic of a Differential Abundance Analysis System (DAA System), according to an embodiment.

FIG. 2 shows a schematic of an example Differential Abundance Analysis system also referred to herein as "the DAA system" or as "the system" 100. The DAA system can be configured to generate spike-in mixes. In some embodiments, the DAA system can be configured to use information related to the spike-in mixes and evaluate two or more workflow pipelines for differential abundance analyses of sequence data. In some embodiments, the DAA system can be configured to use information related to the spike-in mixes and validate results obtained from differential abundance analyses of sequence data.

The system 100 includes a Sequence Processing Validation device 110 coupled or suitably connected (through wired or wireless connection methods) to a user device 102 via a communication network 106. Although illustrated as one user device 102 the Sequence Processing Validation Device (or the SPV Device) 110 can be coupled to any number of user devices and/or remote or local data sources as required.

The user device 102 can be any suitable client device or a computing machine. For example the user device 102 can be a hardware-based computing device and/or a multimedia device, such as, for example, a server, a desktop compute device, a smartphone, a tablet, a wearable device, a laptop, a personal computer (PC), a personal digital assistant (PDA), a smart phone, a tablet PC, a server device, a workstation and/or the like. In some instances, the user device 102 can also be part of a machine configured to analyze a sample (e.g., a sequencing machine) configured to be able to transfer data resulting from the computation. The user device 102, while not shown in FIG. 1, can include at least a memory, a processor, a network interface, and an output device.

The communication network 106 can support wired or wireless connectivity. In some embodiments, the system 100 can be an enterprise system at least partially hosted in an enterprise server, such as, for example a web server, an application server, a proxy server, a telnet server, a file transfer protocol (FTP) server, a mail server, a list server, a collaboration server and/or the like.

The SPV device 110 can include and/or have access to a processor 120, an Input/Output (I/O) unit 140, a memory 160 and a communicator 180, each being interconnected to the other. In some embodiments, the SPV Device 110 can be a server device. In some embodiments, the SPV Device 110 can be an enterprise device, such as, for example, a desktop computer, a laptop computer, a tablet personal computer (PC), and/or the like. In yet other embodiments, portions of the SPV Device 110 can be physically distributed across, for example, many chassis and/or modules interconnected by wired or wireless connections. The network can be any type of network such as a local area network (LAN), a wide area network (WAN), a virtual network, a telecommunications network, implemented as a wired network and/or wireless network. The Input/Output Unit 140, for example, or the memory 160, can be housed in one device or in some embodiments, can be distributed across many devices. The Communicator 180, similarly, can be housed in one device in some embodiments, and distributed across many devices in some other embodiments.

The processor 120 can be, for example, a hardware based integrated circuit (IC) or any other suitable processing device configured to run and/or execute a set of instructions or code. For example, the processor 120 can be a general purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC) and/or the like. The processor 120 can be operatively coupled to the memory 160 through a system bus (for example, address bus, data bus and/or control bus).

The processor 120 can be configured to run one or more applications to support various methods involved in processing of sequencing data using one or more workflow pipelines and statistical evaluation of sequence processing carried out through the set of workflow pipelines as described herein. In some embodiments, the one or more applications run in the processor 120 can be part of an enterprise software or analysis package (e.g., bioinformatics package or statistical analysis package). The processor 120 can for example be equipped with one or more apparatuses that may include one or more associated software to carryout various portions of designing or building information required to generate one or more template polynucleotides that can serve as spikes and/or spike mixes as described herein. The processor 120 can include one or more associated software to carryout various portions of designing sequence processing, the various portions including, for example, to annotation of sequencing reads of a genomic data set (e.g., a microbiome) obtained from high-throughput sequencing of PCR amplified markers in genomic or microbiomic data, grouping and/or classifying clusters of amplicon sequence variants (ASVs) or operational taxonomic units (OTUs) taxa based on analyses of sequencing reads, predicting and or performing statistical tests to evaluate differences in relative abundance, etc. In some embodiments, the processor 120 can be equipped with apparatuses and associate software to receive an unknown sample and validate its purported source or origin or author. In some embodiments, each of the above mentioned portions of the processor 120 can be software stored in the memory 160 and executed by processor 120.

The memory 160 can be, for example, a random access memory (RAM), a memory buffer, a hard drive, a read-only memory (ROM), an erasable programmable read-only memory (EPROM), and/or the like. The memory 160 can store, for example, one or more software modules and/or code that can include instructions to cause the processor 120 to perform one or more processes, functions, and/or the like such as designing template spike polynucleotides, sequence processing, performing differential abundance analyses using predefined workflow pipelines, evaluating differential abundance analyses carried out using various different workflow pipelines, predicting errors or statistical estimates, etc. In some embodiments, the memory 160 can include extendable storage units that can be added and used incrementally. In some implementations, the memory 160 can be a portable memory (for example, a flash drive, a portable hard disk, and/or the like) that can be operatively coupled to the processor 120. In other instances, the memory can be remotely operatively coupled with the compute device. For example, a remote database server can serve as a memory and be operatively coupled to the compute device.

The memory 160 can include one or more databases or a look up tables (not shown in FIG. 2) storing information relating to raw data including sequence readings, sequence information relating to generation and use of template spikes, compositions of spike mixes, relative abundance of each template spike in each spike mix, results from sequence processing using unique workflow pipelines, etc. The memory 160 may include one or more storage systems for the information associated to these specific use cases (e.g. unique identifiers for template spikes, spike mixes, or sequence processing pipelines for differential abundance analyses, etc.,)

Communicator 180 can be configured to receive information sent from the user device 102 or any other external device or data source via the communication network 106. The communication network 106 can support a wired or wireless method of communication. The communicator 180 can be a hardware device operatively coupled to the processor 120 and memory 160 and/or software stored in the memory 160 executed by the processor 120. The communicator 180 can be, for example, a network interface card (NIC), a Wi-Fi™ module, a Bluetooth® module and/or any other suitable wired and/or wireless communication device. Furthermore the communicator 180 can include a switch, a router, a hub and/or any other network device. The communicator 180 can be configured to connect the SPV device 110 to a communication network 106. In some instances, the communicator 180 can be configured to connect to a communication network such as, for example, the Internet, an intranet, a local area network (LAN), a wide area network (WAN), a metropolitan area network (MAN), a worldwide interoperability for microwave access network (WiMAX®), an optical fiber (or fiber optic)-based network, a Bluetooth® network, a virtual network, and/or any combination thereof.

In some instances, the communicator 180 can facilitate receiving and/or transmitting a file and/or a set of files through the communication network 106. In some instances, a received file can be processed by the processor 120 and/or stored in the memory 160 as described in further detail herein. In some instances, as described previously, the communicator 180 can be configured to send data collected and/or analyzed by the processor 120 to another device that the SPV device 110 is connected to.

While not shown in the schematic in FIG. 1, the SPV device 110 can include an output device such as a data presentation or a display device (e.g., a LCD display).

Template Polynucleotide Sequences—Spikes

Figure 3D:
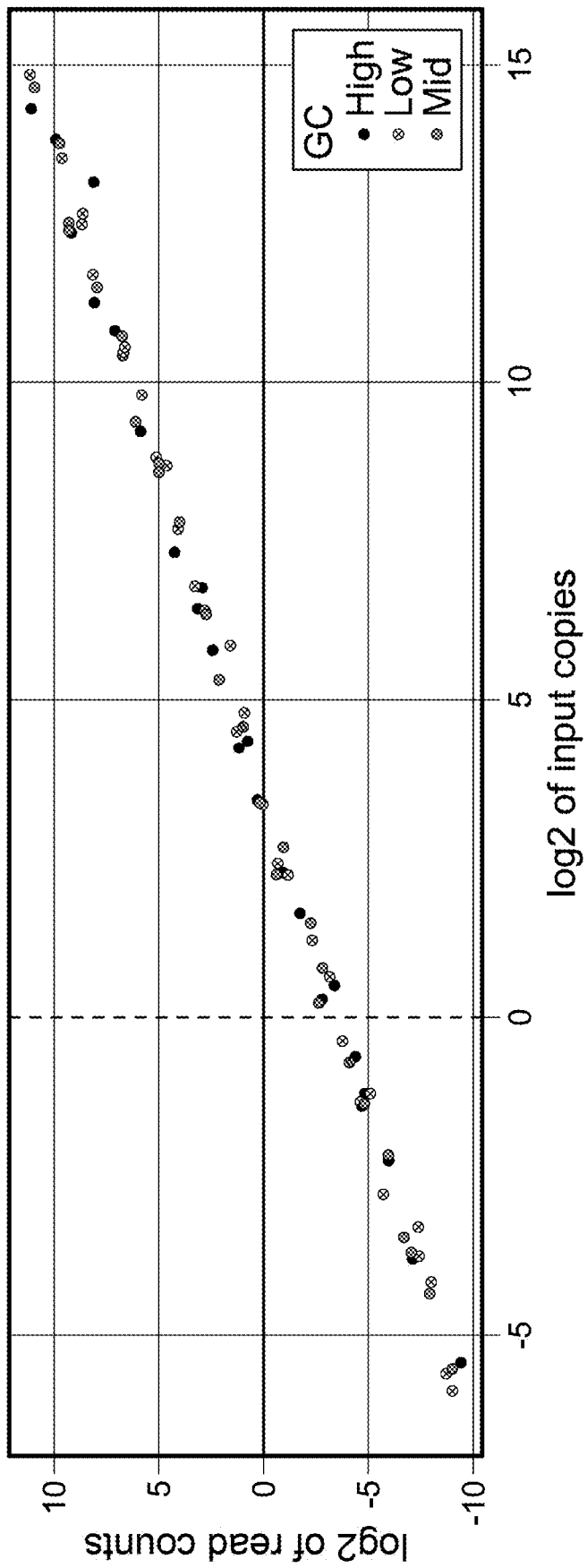
FIG. 3D is a plot showing a schematic representation of a set of template polynucleotide spikes with varying GC content and varying relative abundance, to be used for validation of differential abundance analyses by a DAA system according to an embodiment. Input Copies (x)=1; PCR detection limit at 50 fg. Reads (y)=1; sequencing detection limit at 100 k reads.

Embodiments described herein include systems and methods used for the design and generation of unique polynucleotides that can serve as template spikes for validation of differential abundance analyses methods. FIGS. 3A, 3B, and 3C are schematic illustrations of example sequence structures of example template spikes that can be used for validating differential abundance analyses using the region of the microbiome corresponding to the 16S rRNA gene. A set of template spikes (e.g. 69 template spikes) can be designed and generated to form a library. A DAA system such as the system 100 described above can be used to generate the library of template spikes. Spikes can include multiple different DNA sequences that are distinctly different from the target molecules of interest being studied (e.g. the 16S region) and have varying GC content comparable to the GC content of the target molecules of interest. For example, in the illustrated application of validation of differential abundance analyses in microbiome data, the template spikes can have variable GC content to mimic various microbial communities. An example distribution of 69 unique template spikes with variable GC content and variable inputs copies and/or read counts upon sequencing is illustrated in FIG. 3D. In the example set of template spikes there are 3-4 unique sequences per QS input level (abundance level) with a total of 21 levels, with varying GC content at each level. The library of template spikes is configured to span QS orders of magnitude, for example, up to a max starting quantity of 2,000 copies (based on input mass pre-PCR) e.g., per reaction unit.

The spikes can include control DNA fragments that have approximately the same length as the sample's targeted DNA fragments prior to library construction. In some embodiments, they have a length that is similar to the target amplicon length.

As illustrated in FIGS. 3A, 3B, and 3C, each example template spike in the example implementation described herein can include complements to the 16S V4 primers on either end of a non-16S sequence. In some implementations, the intermediate non-16S region can be configured to be of a predetermined length (e.g. 250 bases). In some implementations, the non-16S region can be derived from an existing databases such as the SRM 2374 data base containing DNA Sequence Library for External RNA Controls maintained by the National Institute of Standards and Technology (NIST). In some implementations the total length of the template can be configured to meet a predefined target (e.g. ~295 bp, comparable to the V4 amplicon size). The double stranded DNA fragments can be configured to be PCR-ready and can be added directly to PCR reaction (*1 mix per sample). For example, the generation of template spikes can include generation of primers designed (POSA) to amplify the 69 negative control template spikes derived from the NIST database with the non-16S sequences flanked by 16S rRNA V4 universal primer sequence. All primers can include at their 5' end a universal sequence for amplification of the microbial 16S rRNA V4 region and at their 3' end a sequence that specifically anneals to the NIST sequence for that template spike. Some example primer sequences are provided in Table 1 below. In some instances, amplified products can be verified by Sanger sequencing and quantified (POSA).

While the above illustration is related to the generation of template spikes for the 16S V4 region, this approach can be suitably used for any amplicon region including for example the V1-V3 regions, V3-V4 regions, or the 18S region, or regions of viral genome corresponding to capsid proteins, fungal genes, mitochondrial genes, DNA or RNA polymerases, tail proteins, etc.

Spike-In Standard Mixes

The generated library of template spikes can be used to generate a predetermined number (e.g. three) of spike-in mixes such that each mix includes the same set of template spikes but with known combinations of predetermined relative abundance of each template spike. In some implementations the 3 mixes can include N spikes with constant concentration and N spikes with varying concentration. The number of template spikes (N) can be any number greater than 1, e.g., 75 to 100, 50 to 100, 25 to 100, 10 to 100, 2 to 100, 50 to 75, 25 to 75, 10 to 75, 2 to 75, 25 to 50, 10 to 50, 2 to 50, 10 to 25, 2 to 25, less than 200 and greater than 10, 20, 30, 40, 50, 60, 70, 80, 90 or 100 in the mix sample.

Figure 4A:
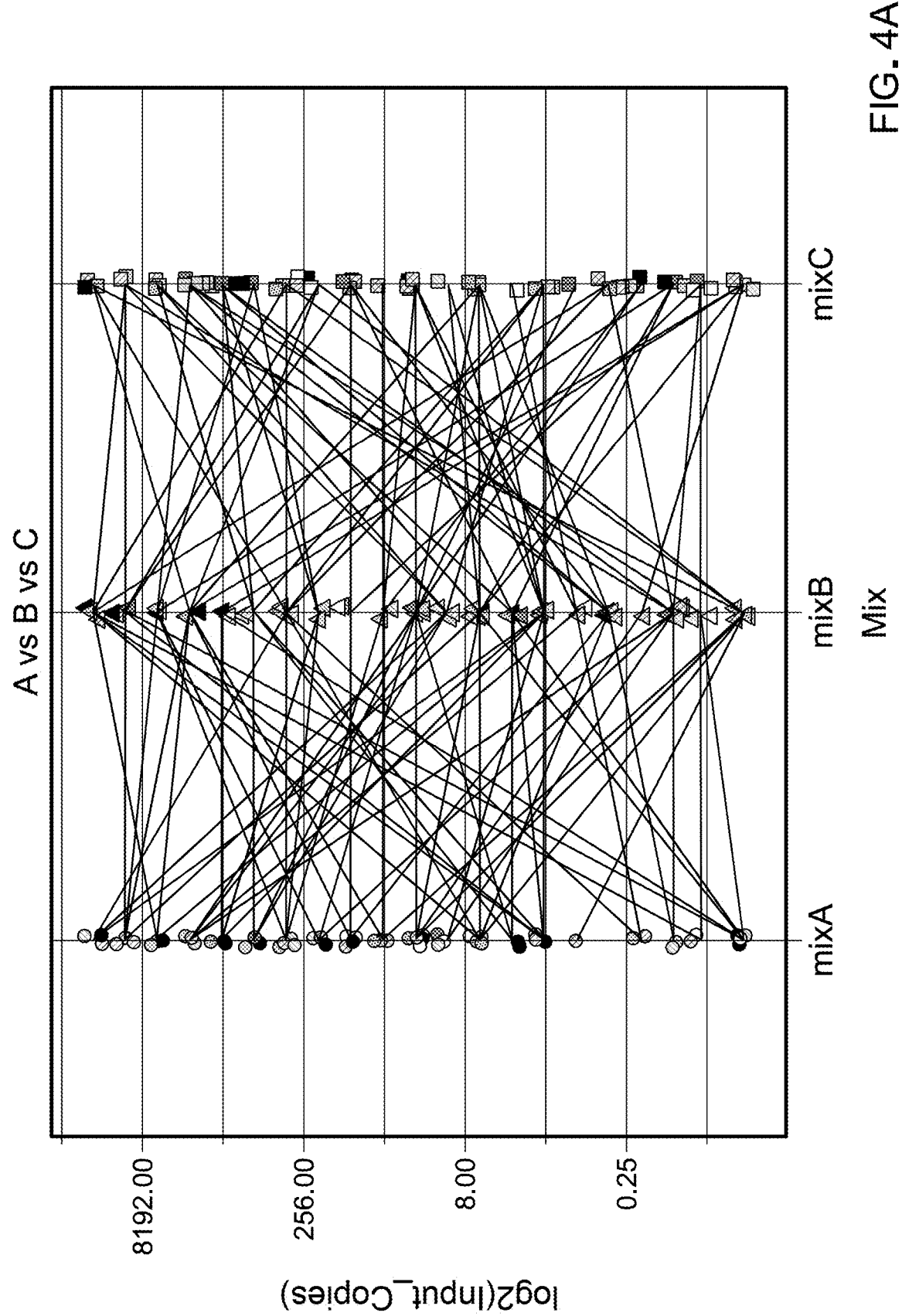
FIG. 4A is a schematic representation of three spike mixes (A, B, and C) indicating unique template spikes (markers) included in each spike mix and the relative abundance of each template spike in each spike mix.

FIG. 4A illustrates three mixes A, B, and C with template spikes indicated by markers, each mix having a same level (straight horizontal lines) or varying levels of each spike. In the illustrated example, each of the 3 mixes includes all 69 unique spike templates at varying levels. By including spikes with high, low, or no shift between mixes, the spike mixes can be used to validate the efficacy of workflow by comparing the expected vs observed shifts for each spike.

Figure 4B:
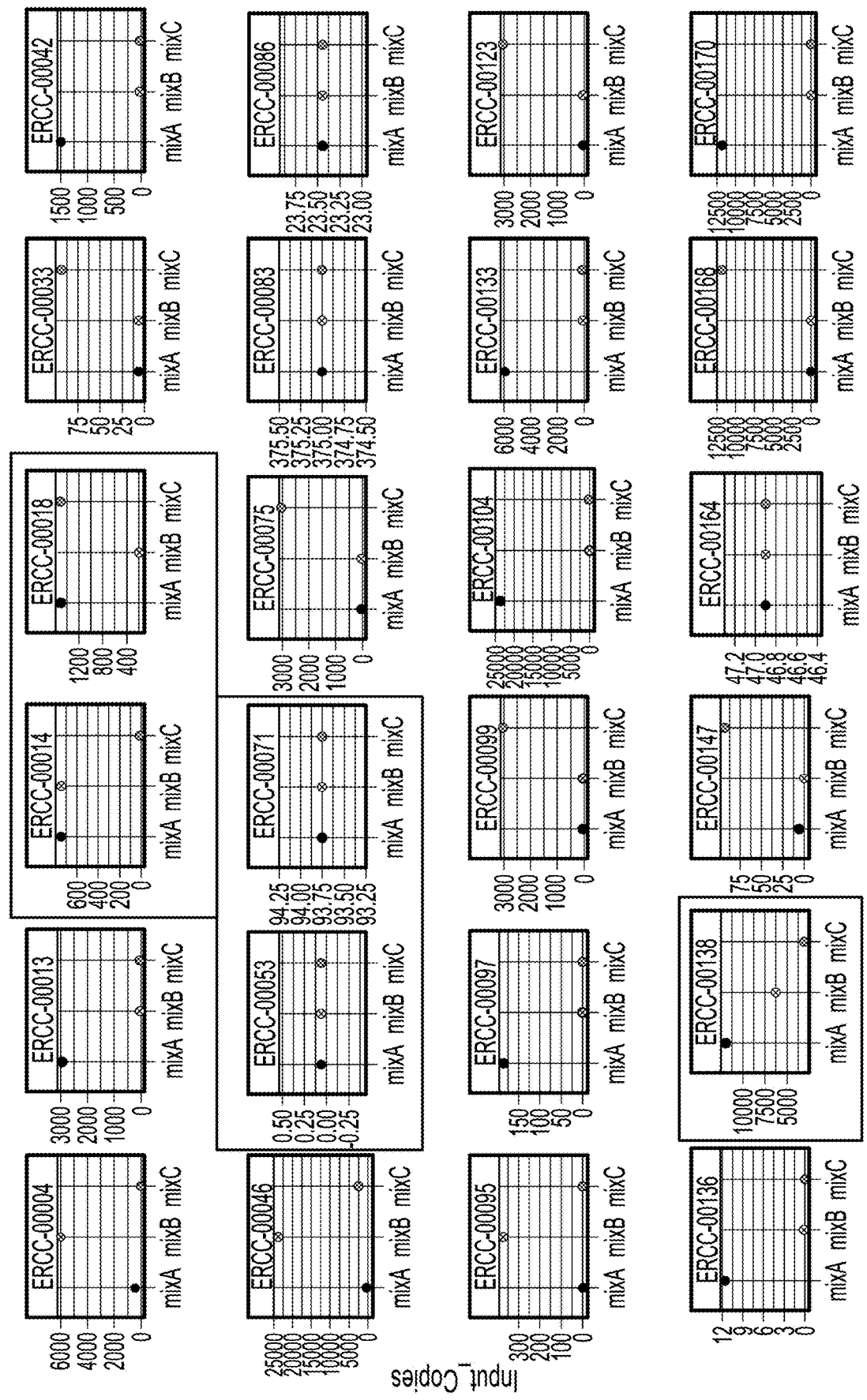
FIG. 4B is a set of plots illustrating the varying relative abundance of example unique template spikes in the three spike mixes illustrated in FIG. 4A.

FIG. 4B illustrates example plots of relative levels of template spikes across the three mixes, with some staying constant and others varying between mixes with a variable degree of shift (e.g. one order of magnitude, or several orders of magnitude, etc.)

Figure 5A:
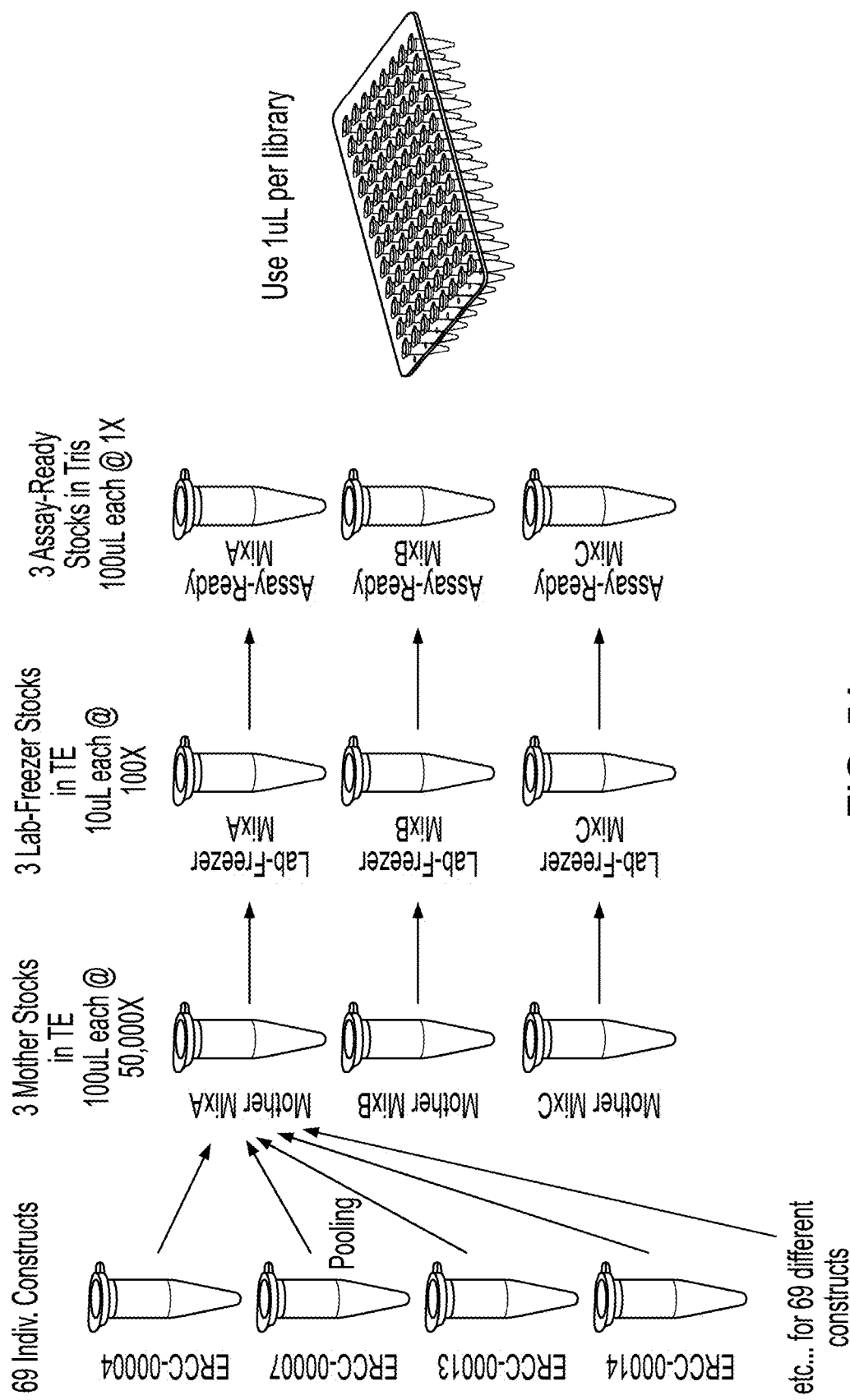
FIG. 5A is a schematic illustration of an example workflow to generate spikes mixes to conduct differential abundance analysis using a DAA system, according to an embodiment.

FIG. 5A is a schematic illustration of an example method to generate internal spike-in standard mixes. 69 unique constructs of template spikes are shown to be pooled to form three mother stocks that may be frozen to be used for assays. Some example combinations of template spikes to generate spike-in mixes is shown in Table 2 below. "PCR Conc ng/uL" shows the concentration of the negative control template spike polynucleotides (described above) and "PCR Conc. Molecules/uL" shows absolute copy number.

Table 2 shows how the quantified stocks can be used to make a 50,000× master stock having predefined concentration (molecules/uL) in each of Mix A, Mix B, and Mix C (tubes A, B, and C). An example procedure can include—take 1.34 ul ERCC-0004, dilute it 10× in TE and add to tube A; take 1.00 uL ERCC-0007, dilute it 10× in TE and add to tube A . . . take 1.00 uL ERCC-00171 and don't dilute it (dilution factor=1) and add to tube A, then bring volume of tube A up to 100 uL (add 0.21 ul TE). Mix A will have 1.88E+07 copies of ERCC-0004 in the 50,000× stock mix. A 5× tube of Mix A will have 1.88E+02 copies.

Figure 5B:
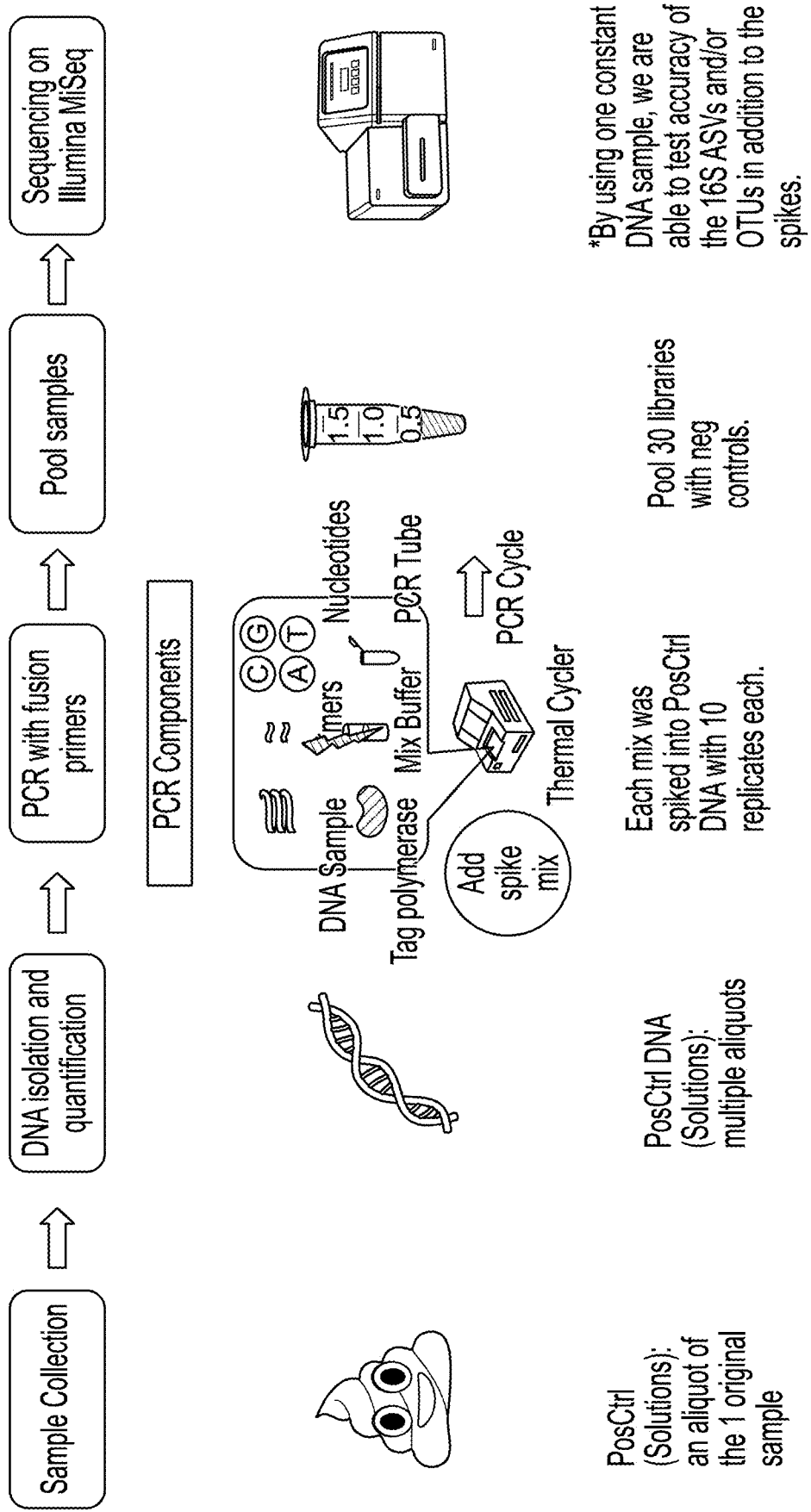
FIG. 5B is a schematic illustration of an example workflow to prepare sequence data to conduct differential abundance analysis using a DAA system, according to an embodiment.

The prepared spike-in mixes can be used as internal standards and directly added to PCR mixes during processing of an experimental DNA sample. FIG. 5B is a schematic illustration of an example procedure where a sample DNA is mixed with an internal spike-in mix and processed through PCR and sequenced (e.g. using Illumina MiSeq). The procedure illustrated in FIG. 5B can be in preparation of using the spike-in mixes with sample DNA to validate methods used for differential abundance analysis.

In the procedure, one or more samples can be collected (e.g. bodily fluid of a subject like blood, urine, saliva or, biological matter sourced from the subject such as stool, excised tissue, etc, or a soil sample). For example, At 553 DNA is isolated from each sample and quantified using standard protocols such as MagAttract PowerMicrobiome DNA/RNA kit (Qiagen). gDNA quantification can be carried out for example using a Quant-iT™ PicoGreen™ dsDNA Assay Kit (ThermoFisher Scientific).

At 555 the sample is mixed with the internal spike-in standard mixes and fusion primers and processed through PCR. As an example of PCR of 16S rDNA, V4 region (PosCtrl DNA, multiple aliquots) PCR Library Amplification PCR can be performed using Platinum Hot Start Master Mix (ThermoFisher Scientific). The forward 16S V4 Primer can be GTGCCAGCMGCCGCGGTAA (SEQ ID NO: 1).

Figure 5C:
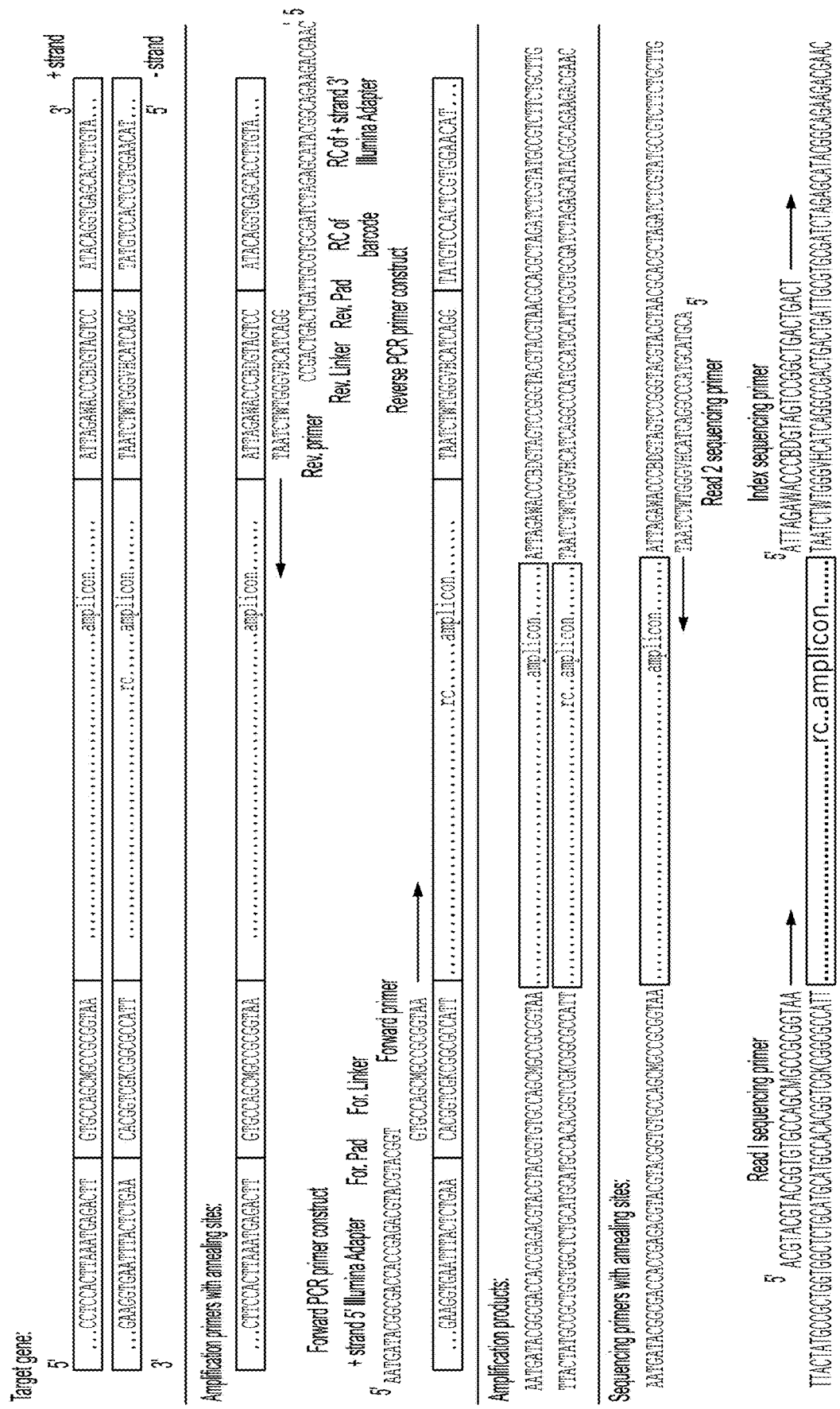
FIG. 5C shows examples of PCR forward and reverse primers to generate amplicons for Illumina sequencing (see, e.g., Caporaso et al., 2011, PNAS, 108:4516).

The PCR forward and reverse primers to generate amplicons for Illumina sequencing, can be the same as those illustrated in FIG. 5C derived from the scientific publication by Caporaso et al., 2011, PNAS, 108:4516. The linker provides extra space so annealing to the chip doesn't interfere with the sequencing reaction.

```
Forward primer:
                                           (SEQ ID NO: 2)
AATGATACGGCGACCACCGAGACGTACGTACGGTGTGCCAGCMGCCGCGGT

AA

Reverse primer:
                                           (SEQ ID NO: 3)
5'-CAAGCAGAAGACGGCATACGAGATNNNNNNNNNNNNNAGTCAGTCAGCC

GGACTACHVGGGTWTCTAAT

Reverse 16S V4 Primer:
                                           (SEQ ID NO: 4)
GGACTACHVGGGTWTCTAAT
```

TABLE 3

| Reagent | Volume |
| --- | --- |
| Platinum Hot Start Master Mix (ThermoFisher Scientific) | 12.5 uL |
| Forward Primer (10 uM) | 0.5 uL |
| Reverse Primer with barcode (10 uM) | 0.5 uL |
| Sample DNA (6.25 ng/uL) | 2 uL |
| 5X standard (Mix A, MixB or Mix C as defined in Table 2) | 2 uL |
| PCR-grade water | 7.5 uL |
| Total | 25 uL |

The master mix that is put into each well of the 96-well plate can contain the Platinum Hot Start Master Mix, the Forward Primer and water only (20.5 ul). Then, individually, 2 ul sample can be aliquoted to each well. In some instances, where there is only one sample the same sample is pipetted into all wells except a negative control well). 2 uL of standard spike-in mixes A, B or C is aliquoted in into each well, and 0.5 ul of Reverse Primer is aliquoted into each well. Table 3 provides a list of reagents and their volumes. The reverse primer can include a unique barcode sequence so that the PCR amplicon for each well is identifiable by the barcode that's incorporated through the barcode sequence in the reverse primer (i.e., one has a 96 well plate with 96 reverse primers that are unique only in the barcode sequence).

At 557 of the procedure 500, after amplification of the 96-well plate, all samples can be pooled and sequenced—the sequence can be used to identify the sample source of each amplicon sequence. The PCR can be run using the following conditions.

Thermocycler conditions:
Initial denaturation: 94° C.
Cycles:
Denature at 94° C., 30 sec
Anneal primers at 50° C., 30 sec
Extend DNA at 72° C., 30 sec
Repeat steps a, b, c 25 times
Final extension at 72° C., 10 min
Hold at 4° C.

PCR samples can be purified using the AMPure XP PCR Purification, Cleanup & Size Selection kit (Beckman Coulter) then stored at 20° C. Amplicons in each PCR reaction product can be quality checked using Agilent DNA 7500 Kit and Agilent 2100 Bioanalyzer (Agilent Technologies). Amplicons in each PCR reaction product can be quantified using Quant-iT™ PicoGreen™ dsDNA Assay Kit (ThermoFisher Scientific). After quality control and quantification, at 559 of the procedure 500, equimolar amounts of each amplicon product can be added to a single tube for sequencing with the Illumina MiSeq system. DNA can be diluted to 4 nM and using protocol provided in Illumina's "16S Metagenomic Sequencing Library Preparation" manual sequencing can be carried out.

In some instances, a PhiX control library can be prepared by diluting denatured V4 library to 6 pM and diluting denatured PhiX control library to 6 pM, the spiking in 15% PhiX library to the 6 pM V4 library (90 uL 6 pM PhiX library, 510 uL 6 pM V4 library).

From information available via Illumina (at the URL www.illumina.com/products/by-type/sequencing-kits/cluster-gen-sequencing-reagents/phix-control-v3.html) "PhiX Control v3 is a reliable, adapter-ligated library used as a control for Illumina sequencing runs. The library is derived from the small, well-characterized PhiX genome, offering several benefits for sequencing and alignment. The versatile PhiX Control v3 is provided as a ready-to-use library, and can be utilized in diverse applications to add value to your workflow and increase confidence in your results. The PhiX library provides a quality control for cluster generation, sequencing, and alignment, and a calibration control for cross-talk matrix generation, phasing, and prephasing. It can be rapidly aligned to estimate relevant sequencing by synthesis (SBS) metrics such as phasing and error rate."

Sequencing at 559 of procedure 500 can be carried out with MiSeq Reagent Kit v3 (600 cycle). The combined library (V4 spiked with PhiX) can be loaded into the sample port. Sequence results can be processed and analyzed as described further below.

Using Spike-In Standard Mixes for Validation of Differential Abundance Analyses

Figure 6:
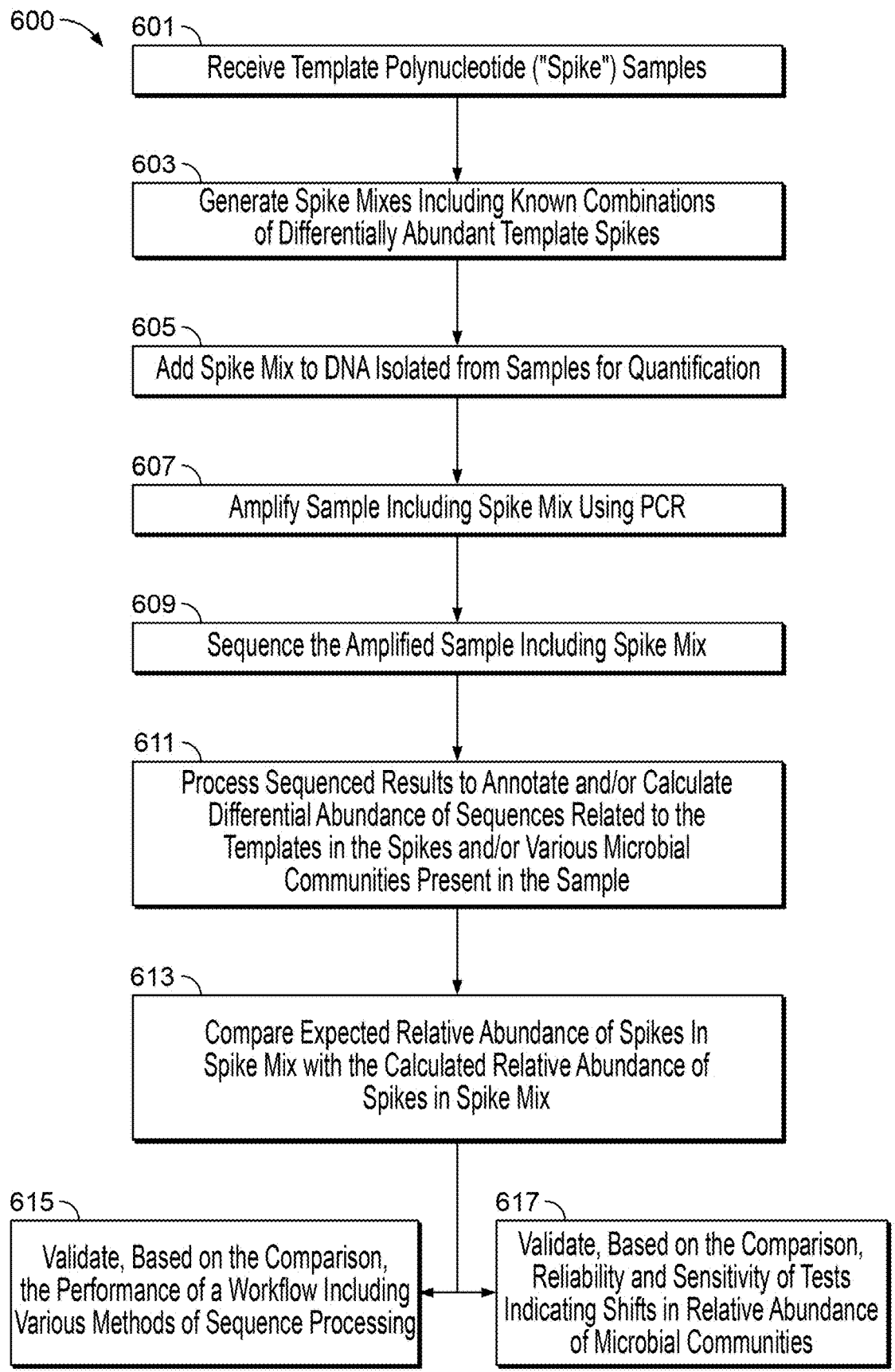
FIG. 6 is a flowchart describing a method for validating results obtained from a differential abundance analysis, according to an embodiment.

FIG. 6 illustrates a method 600 of using internal spike-in standard mixes for validating the performance of sequence processing pipelines. Method 600 also illustrates the use of internal spike in standard mixes in providing measures of confidence (e.g. measures of reliability and sensitivity of tests indicating a diagnosis or detection of a condition (e.g. health condition) based on results from differential abundance analyses. Portions of method 600 can be substantially similar to the procedure 500 described above with reference to the illustration in FIG. 5B. Accordingly, the similar portions are not further described in detail herein. For example, the method 600 at 601 includes receiving a library of template polynucleotide spikes and at 603 includes generating spike mixes including known combinations of differentially abundant template spikes. The template spikes can be substantially similar to those described above with reference to FIGS. 3A-3D, and the spike mixes can be similar to the mixes described above with reference to FIGS. 4A, 4B, and 5A-5C. At 605 the spike mixes can be added to DNA isolated from one or more samples and at 607 the combined mixture can be amplified using PCR methods, and at 609 sequenced, as described with reference to the procedure 500 illustrated in FIG. 5 and described above.

At 611 the sequencing results can be processed using a predetermined workflow pipeline. The workflow pipeline can be one of many including the example pipelines described in further detail below. Following sequence processing at 611, at 613 an expected set of results can be generated using prior information about the spike mix added to each sample (e.g. information relating to the expected relative abundance or shift in abundance of each template spike given the spike mix that was added). The expected results can be compared against the calculated results obtained from sequence processing. The comparison can be used for any suitable validation of the workflow that was used to obtain the calculated results, or to validate the significance of the results obtained. At 615, for example, based on the comparison, the performance of two or more workflow pipelines can be evaluated using the same data. At 617, based on the comparison of expected and calculated results at 613, the significance or confidence associated with results generated from the calculated results can be ascertained. For example, a measure of reliability or accuracy of detecting shifts in relative abundance can be computed using the difference between the expected and calculated data for each abundance level of template spikes, and these measures can be used to validate results obtained from analyzing microbiome data obtained from unknown samples.

Example Workflow Pipelines Evaluated for Differential Abundance Analysis

Figure 7A:
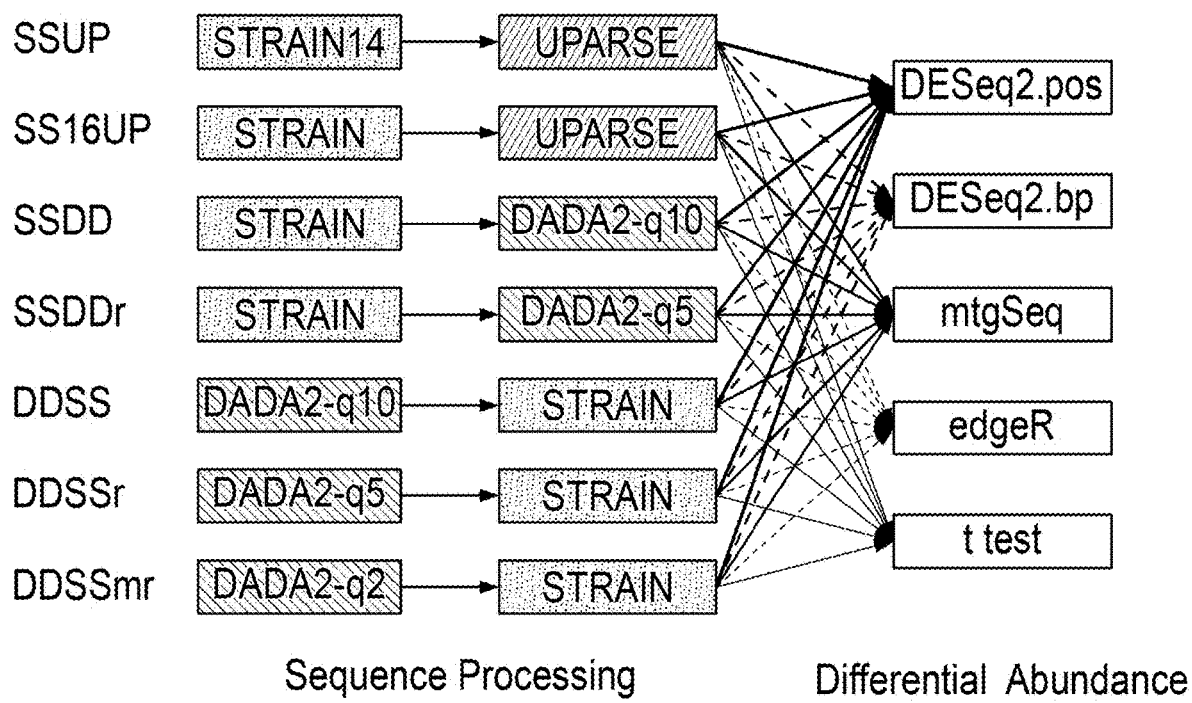
FIGS. 7A and 7B are a schematic illustrations of several example workflow pipelines that can be used for differential abundance analyses, which can be evaluated and validated using a DAA system according to an embodiment.
Figure 7B:
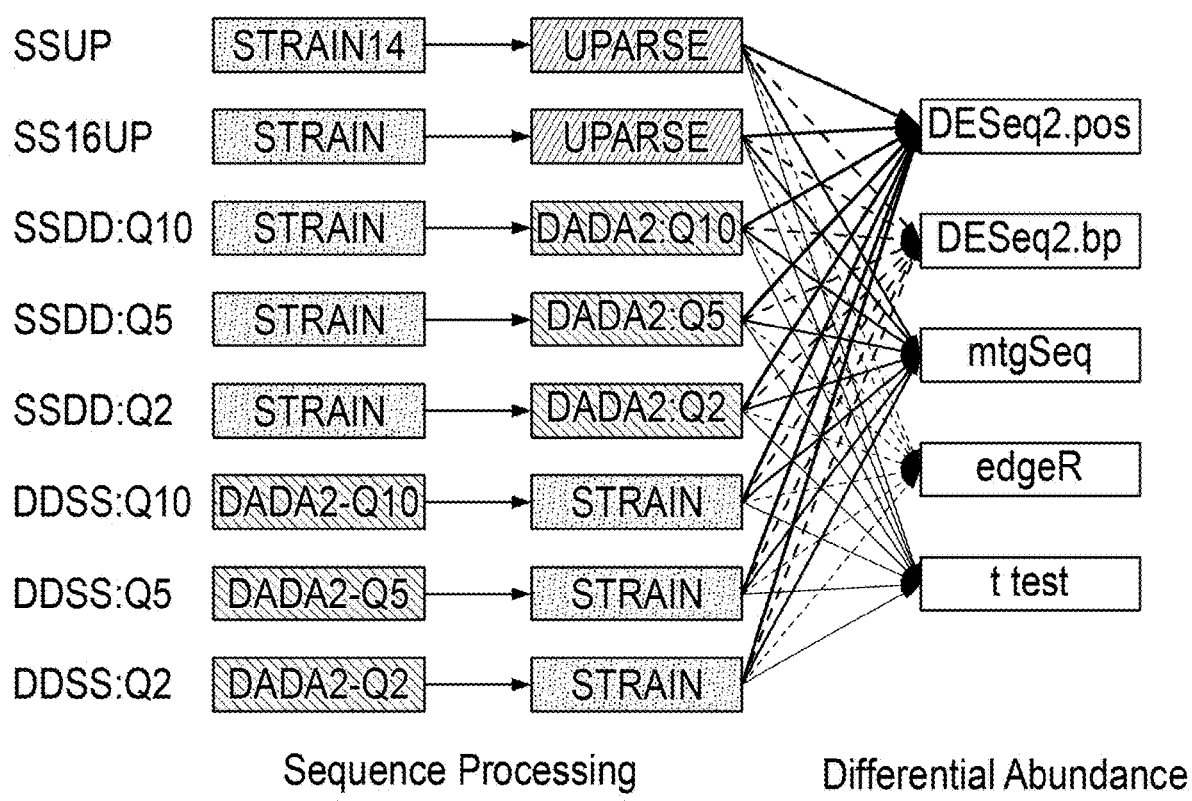

As a demonstrative example, the DAA system and the methods of generating and using standard spike-in mixes described herein were used to compare and evaluate a set of selected sequence processing workflow pipelines, and evaluate the results obtained from using these pipelines. FIGS. 7A and 7B illustrate sets of selected workflow pipelines that were evaluated. In some example workflow pipelines, as indicated, the sequence readings were run through an annotation tool or mapping algorithm (e.g. STRAIN) before running through clustering or grouping routines (e.g., UPARSE) and statistical testing for differential abundance analyses using statistical analysis tools (e.g., DESeq2, mtgSeq, edgeR, t-test, etc.). In some workflow pipelines, annotation was done after running through error correcting routines (e.g., DADA2). Some example pipelines were tested in the example implementation described herein.

De Novo Clustering of Sequences Using UPARSE

Using UPARSE, sequences were clustered into OTUs at 97% sequence similarity. Representative sequences were inferred from each OTU cluster. Notably, OTUs generated were not comparable across studies and a combined OTU table cannot be generated for analysis across multiple studies. In pipelines that used the UPARSE routines, sequence reads were first merged and oriented using USEARCH 10.0.240 (e.g., using -fastq_mergepairs and -orient commands, respectively, using default settings) (see Edgar, 2020, Bioinformatics, 26:2460-2461). Reads were quality filtered based on a maximum expected error of 1 before being dereplicated and sorted by size (discarding singletons) using the -derep_fulllength and -sortbysize commands in USEARCH. De novo clustering of Operational Taxonomic Units OTUs was then performed at 97% identity threshold using the -cluster_otus command in USEARCH.

Sequence Processing Using DADA2

In pipelines using DADA2, amplicon sequence variants (ASVs) were inferred by modeling the error in the sequence reads and then inferring 'true' sequences after error correction. This method is expected to infer single-nucleotide differences between ASVs. Notably, using DADA2 the resulting ASVs are comparable across studies. To implement DADA2 routines raw sequence reads were processed with DADA2 using default settings for filtering, learning errors, dereplication, ASV inference, and chimera removal (Callahan et al., 2016, Nat Methods, 13:581-583). Truncation quality (truncQ) was set to 2, 5 or 10 depending on the sequencing processing workflow. For both forward and reverse reads, 10 nucleotides were trimmed from the start and end of each read.

Mapping Reads to Strain Databases

STRAIN=StrainSelectR is a new Second Genome R package that utilizes USEARCH to map all reads against a reference database of StrainSelect2016 and the spikes simultaneously. STRAIN14=StrainSelect2014 is a python-script based classification tool using USEARCH to map reads to StrainSelect2014. Spikes were identified after the fact by mapping OTU representative sequences to the spike template sequences. In 4 of the 7 total sequence processing workflows (noted as SS14 or SS16-xx), reads were mapped against an in-house strain database first. Reads were then merged and oriented using USEARCH (-fastq_mergepairs and -orient commands respectively) (Edgar, 2020, Bioinformatics, 26:2460-2461). In addition, reads that matched to specific strains were not carried through to subsequent analysis for the SS ##-xx workflows. Reads were mapped to two strain databases: STRAIN and STRAIN14. STRAIN refers to read mapping (usearch) against a database of 16S rRNA gene sequences that were obtained from 16S rRNA gene sequencing, genomes, draft genomes, and metagenomic assemblies of known prokaryotic strains; STRAIN14 refers to an older version of the same database.

Differential Abundance Testing

For all tests, performed prevalence filtering was performed. An OTU/ASV/strain/spike was kept if it was present in at least 5% of samples. For features with less than three positive samples in each group, one read was added the deepest sequenced samples per group so that three samples had positive values (a requirement for metagenomeSeq).

Five unique statistical tests were applied: (i) DESeq2 (1.18.1) with positive counts method applied to handle sparse microbiome data, (ii) DESeq2 with betapriors applied, (iii) edgeR (3.20.5), (iv) metagenomeSeq (1.20.1), and (v) t-tests (stats package, v3.4.1) (Love et al., 2014, Genome Biol, 15:1-21; Robinson et al., 2009, Bioinformatics, 26:139-140; McCarthy et al., 2012, Nucleic Acids Res, 40:4288-4297). DEseq2 (poscounts) mimics parameters commonly used for microbiome analyses (DEseq2 (bp), betapriors=TRUE, previous microbiome standards), but allows implementation of a newer version of DEseq2. Both DEseq2 analyses are expected to give similar results.

DESeq2 was used for two different tests: DESeq2 with positive counts method applied to handle sparse microbiome data and DESeq2 with betapriors applied (Love et al., 2014, Genome Biol, 15:1-21). For the DESeq2 with positive counts, estimateSizeFactors( ) was applied using the type=poscounts setting before differential abundance testing with DESeq( ). For DESeq2 with betapriors, DESeq( ) was used for differential abundance testing using the setting betapriors=TRUE. For testing with edgeR, we followed the procedures for differential abundance testing outlined in McMurdie and Holmes 2014 (Robinson et al., 2009, Bioinformatics, 26:139-140; McCarthy et al., 2012, Nucleic Acids Res, 40:4288-4297; McMurdie and Holmes, 2015, PLoS Comput Bio 10). For metagenomeSeq, css normalization was applied with cumNorm( ), then differential abundance testing was carried out with fitFeatureModel( ) (Paulson et al., 2013, Nat Methods, 10:1200-1202). For t test, we used an unpaired t test for differential abundance testing. In addition, we calculated log 2 fold-change (l2FC) with foldchange( ) and foldchange2logratio( ) from the gtools package v3.5.0 (Warnes G R, Bolker B, Lumley T. 2015. gtools: Various R Programming Tools. 3.5.0). Adjusted p-values were calculated using the Benjamini-Hochburg method with p.adjust( ) (stats package, v3.4.1) (Team, 2017, PLoS Comput Biol 10).

Pipeline Rankings Calculations.

For each unique workflow, each spike comparison (mix A vs mix B, mix B vs mix C, etc) was defined as a true positive, true negative, false positive, or false negative based on the adjusted p value and the expected and observed log 2FCs, in which a true positive was a spike comparison that was adjusted-p<0.05 and absolute $\log_2 FC>0$ when the spike was expected to be differentially abundant. Since all libraries were made from the same sample biospecimen (e.g., stool), there were no 16S amplicons expected to be significantly different in abundance between groups. Therefore, we also determined the number of true negative and false positive comparisons involving 16S amplicons. These six values were used for the calculation of the majority the metrics used in pipeline ranking.

Detection rate was calculated as the number of spikes found in a workflow divided by the total number of spikes (69 spikes total). Sensitivity was calculated as the total true positive spikes comparisons divided by the total number of expected differentially abundant spike comparisons. Specificity was calculated as the total true negative spikes comparisons divided by the total number of spike comparisons that were not expected to be differentially abundant. The false negative rate was calculated as the total false negatives divided by the total number of expected differentially abundant spike comparisons. Accuracy was calculated as (total true positive+total true negative)/(total expected differentially abundant+total spike comparisons expected to be differentially abundant). Precision was calculated as total true positives/(total true positives+total false negatives). Theta and sigma were calculated from the linear regression of observed 69 log 2FC and expected log 2FC. Theta was calculated using the slope of this regression as absolute (atan(((slope-expected slope)/(1+expected slope*slope))))*(180/), in which the expected slope was 1 (observed log 2FC=expected log 2FC). Normalized theta was calculated as 1−(theta/180). Sigma was calculated as the square root of the sum of residual errors of each spike comparisons compared to a line with a slope of 1 (observed log 2FC=expected log 2FC). Sigma normalized was calculated in relation to sigma values for all 40 unique workflows, in which sigma normalized=1−(sigma−minimum sigma)/(maximum signal−minimum sigma). The inverse 16S false positive rate was calculated as 1−(total false positive 16S comparisons/total 16S comparisons). Spk16_PPV (positive predictive value) was calculated as total true positives/(total true positives+total false positives+total false positive 16S comparisons). The final pipeline ranking metric was calculated as below: (theta_normalized/2)+(sigma_normalized/2)+detect_rate+Sensitivity+Specificity+Accuracy+Precision+Spk16_PPV*1.5−(FalsePos16S_Rate+FalseNeg_rate). FIGS. 8-25 show results obtained.

Figure 8A:
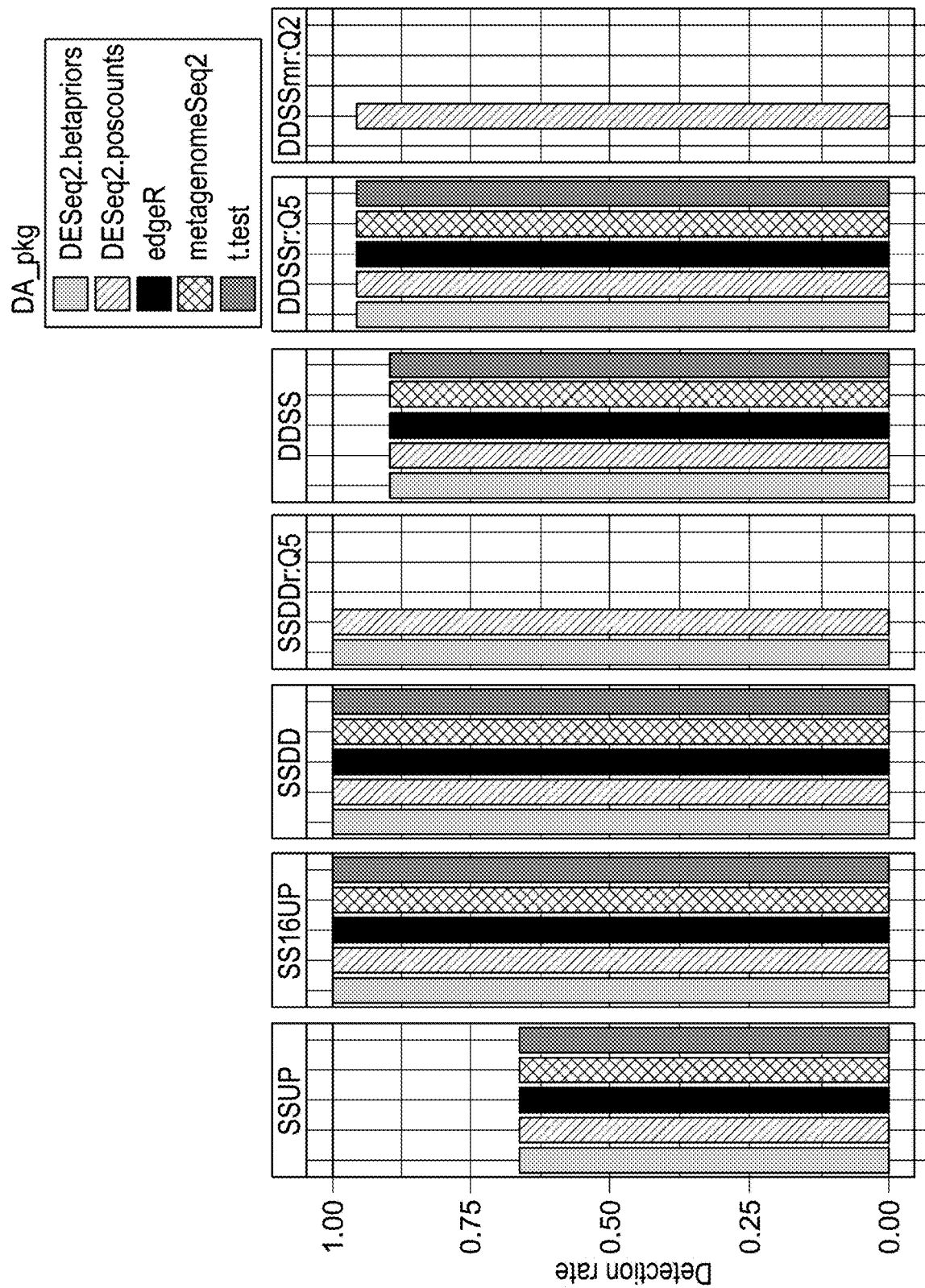
FIG. 8A is an example result from evaluating several workflow pipelines for differential abundance analyses using detection of template spikes as the evaluation metric, using a DAA system according to an embodiment.
Figure 8B:
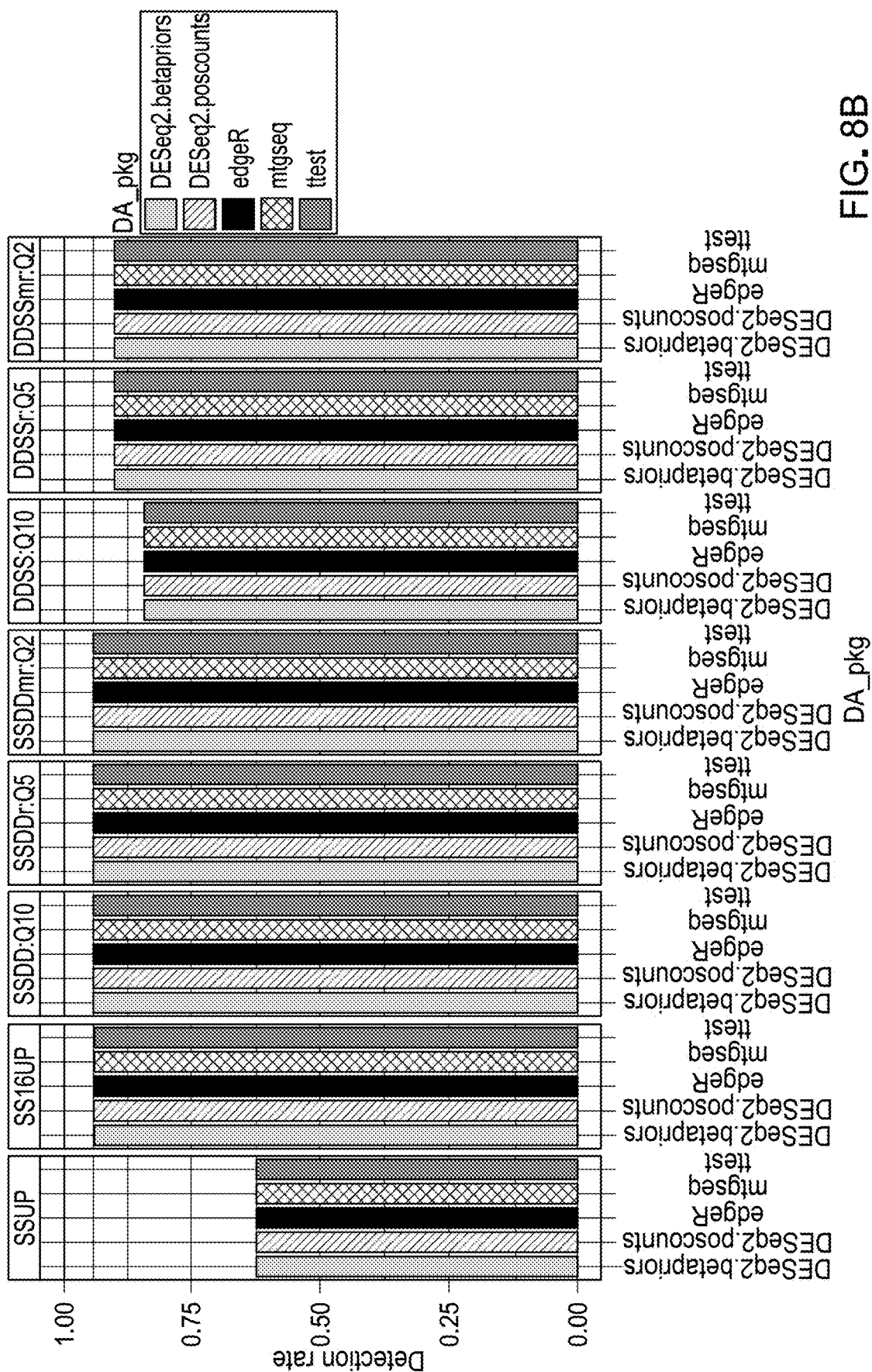
FIG. 8B is an example result from evaluating several workflow pipelines for differential abundance analyses using detection of template spikes as the evaluation metric, using a DAA system according to an embodiment.

FIGS. 8A and 8B illustrate graphs plotting the spike detection rate achieved by each workflow pipeline of the list of pipelines tested—labelled as SSP, SS16UP, SSDD, SSDDr, DDSS, DDSSr, and DDSSmr, with each pipeline tested using each of the analytical tools from the list of DESeq2.betapriors, DESEq2, poscounts, edgeR, metagenomeSeq2, and t-test. Plots show a normalized detection rate of detected spikes divided by total number of spikes (69). As indicated DADA2 missed up to 7 spikes but recovery improved with tuning parameters used. SSUP recovered 47/69, with assignment of OTU representative sequences.

Figure 8D:
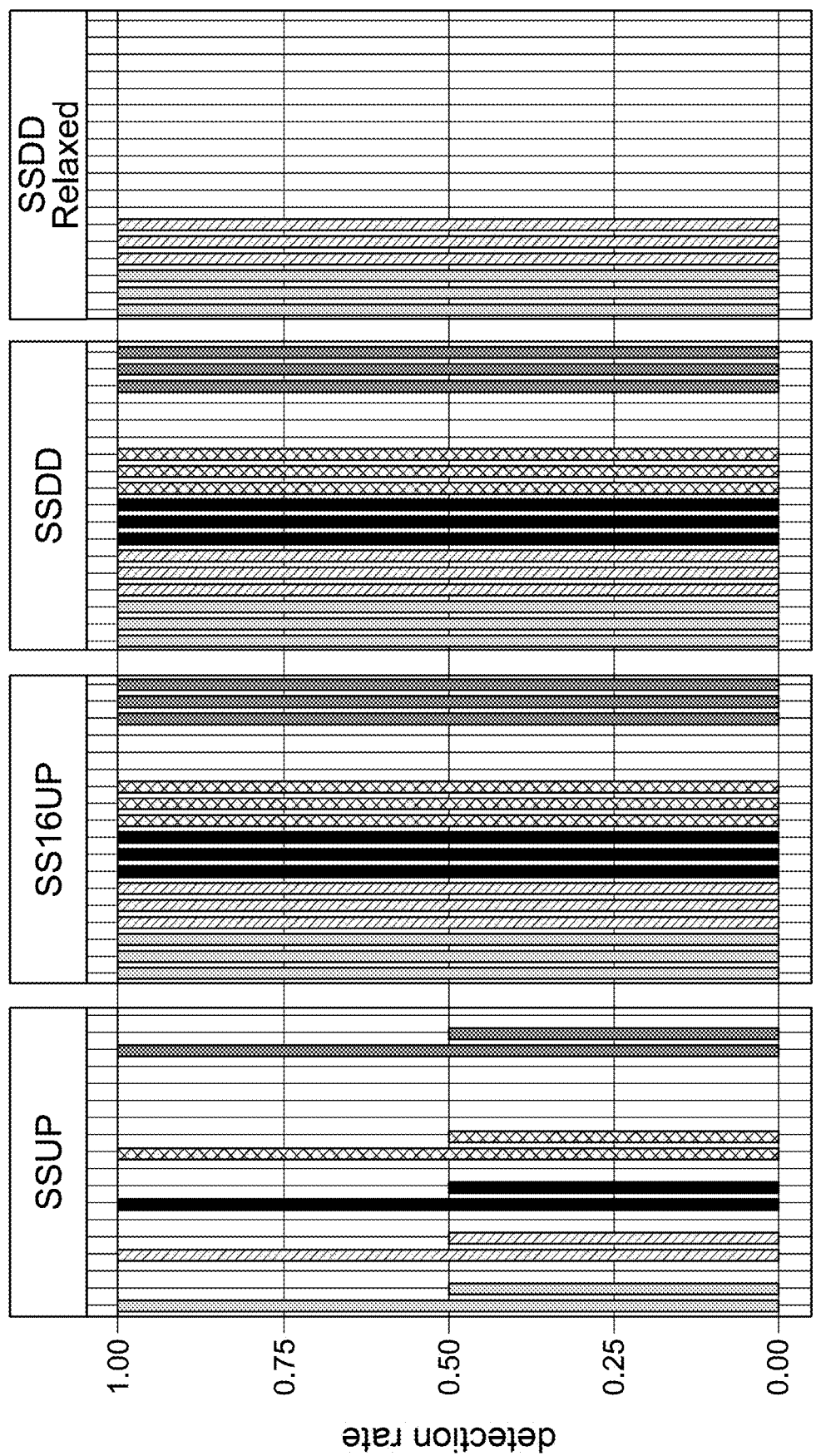
FIG. 8D shows the result from FIG. 8A with further indication of detection of template spikes across the different classes of template spikes categorized by the levels of relative abundance shown in FIG. 8C.
Figure 8D:
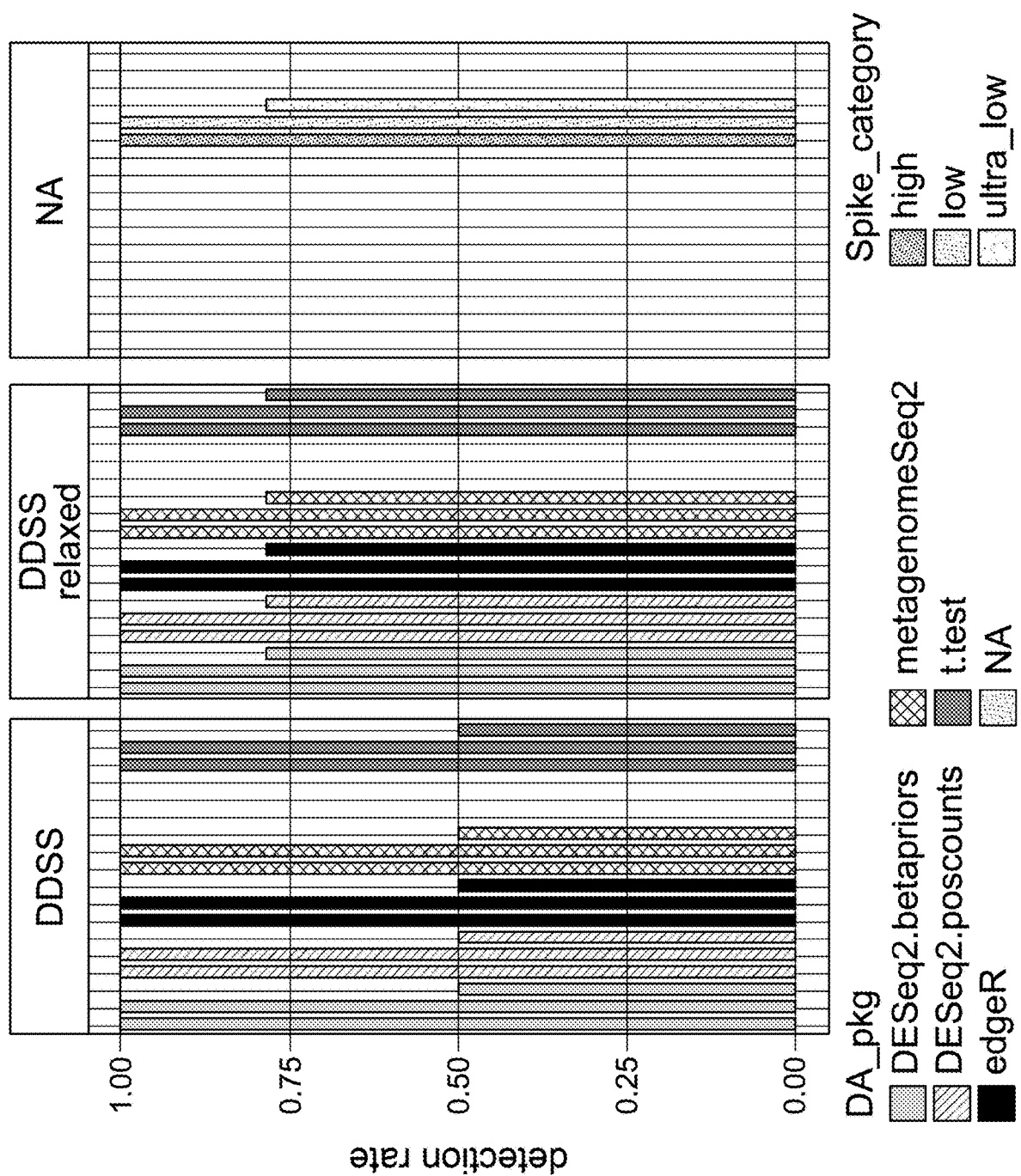
Figure 8E:
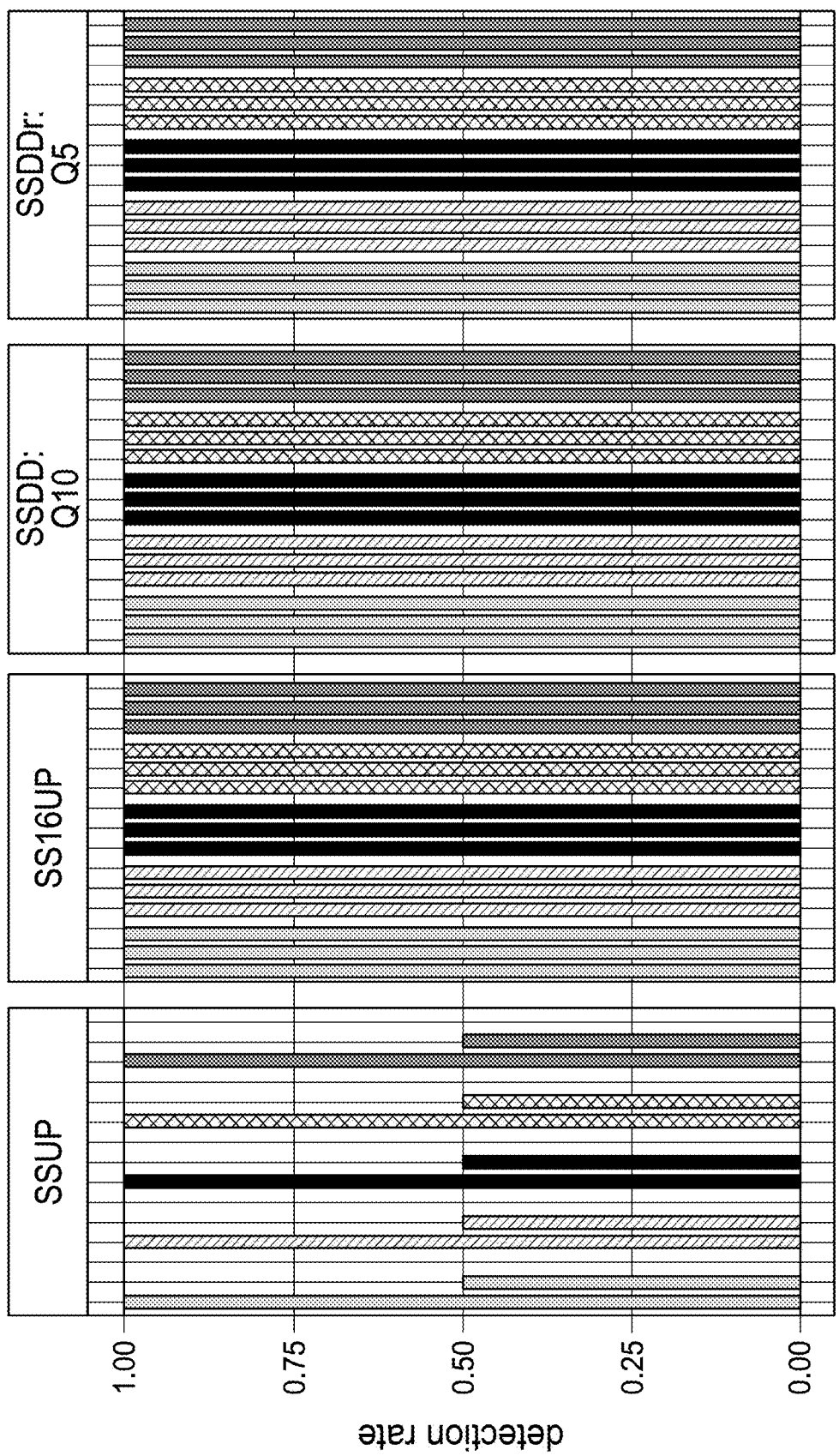
FIG. 8E shows the result from FIG. 8B with further indication of detection of template spikes across the different classes of template spikes categorized by the levels of relative abundance shown in FIG. 8C.
Figure 8E:
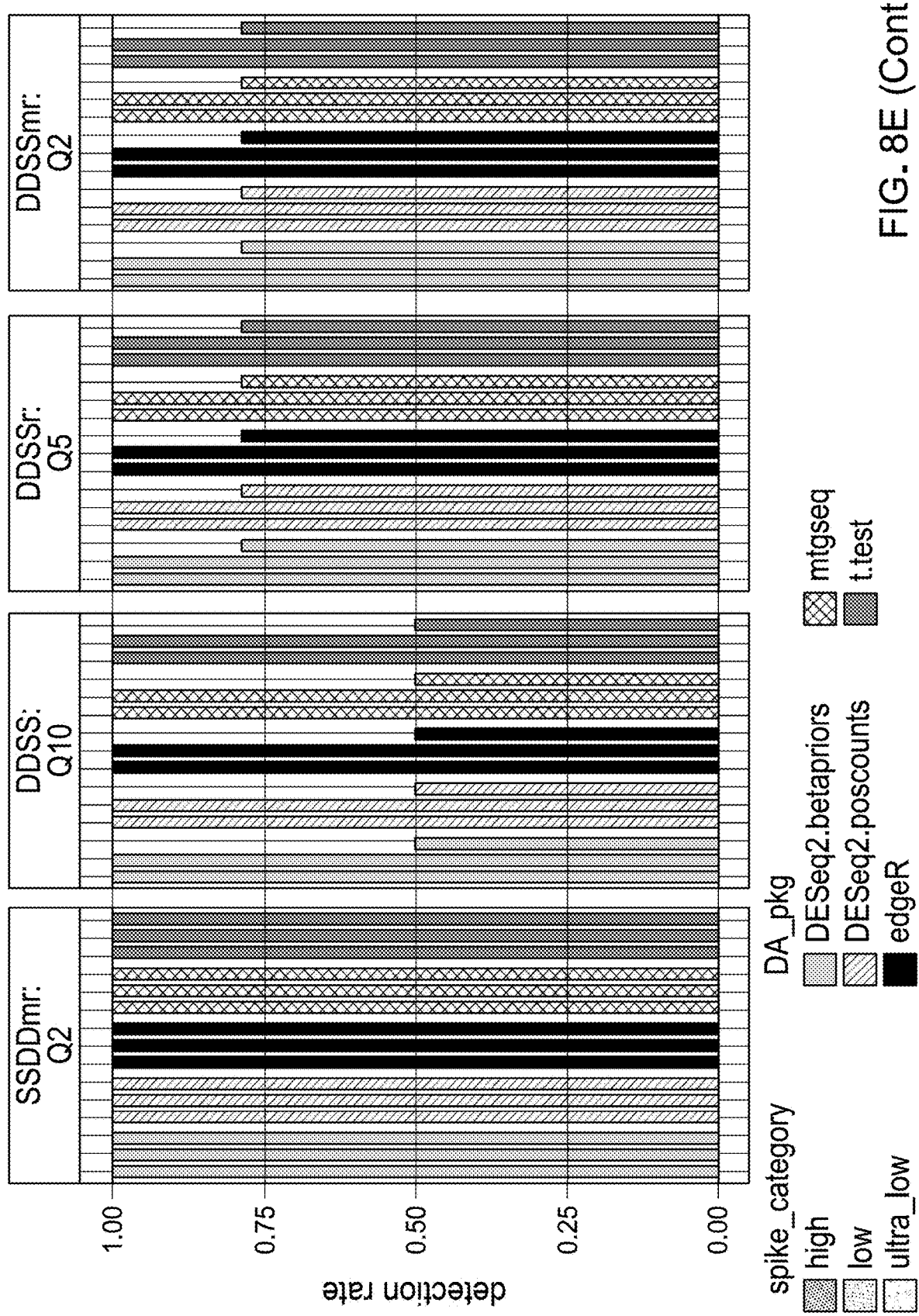

Spikes were also categorized based on max expected abundance of the spike with the following computation. Abundance was estimated as input copies per ul of 1× stock, with 5 ul/PCR rxn used. max Relative Abundance of a spike category was then used to classify 16S ASVs or OTUs into abundance categories. The table in FIG. 8C illustrates a division of spikes based on the relative levels of abundance. As an example, 5 ul of 1× were added to each library of mix A, B, or C such that the anticipated sequencing coverage resulted in ~15% of reads as spikes. maxRA spike category=max Relative Abundance of each spike across all samples & pipelines. Thus the performance of the pipelines can be further subdivided and evaluated based on different levels of abundance. FIG. 8D and FIG. 8E show results obtained using each of the listed pipelines, also considering the levels of abundance of spikes, known a priori. The results indicated that the missing spikes were ultra-low spikes, which likely had few to no sequence reads.

Figure 9:
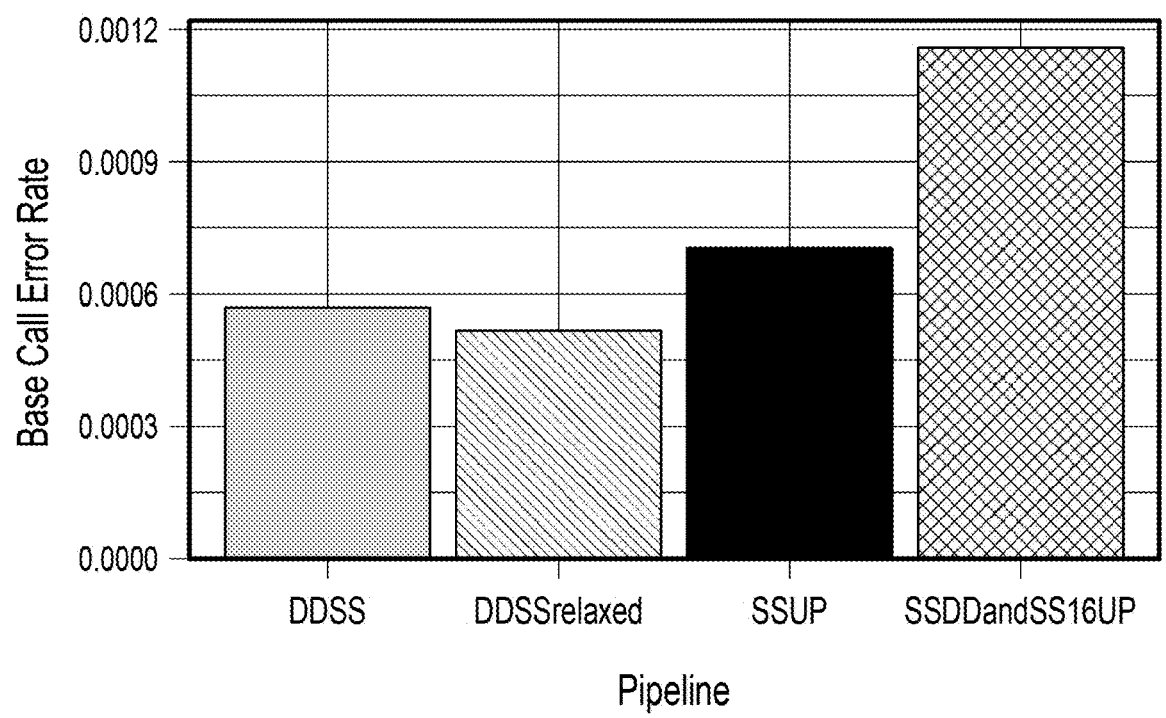
FIG. 9 is an example result from evaluating workflow pipelines for differential abundance analyses using base call error rate as the evaluation metric, using a DAA system according to an embodiment.

FIG. 9 illustrates a graph plotting the performance of the pipelines based on error rates. Base-call error rates on spike representative sequences were used to compute performance measures. Spikes were assigned differently based on pipelines. For example, in pipelines including DDSS, DDSSrelaxed, SSUP cluster (ASV/OTU) representative sequences were searched for spikes. In pipelines including SSDD, SS16DD: strainselectR searches individual reads for spikes. As indicated all pipelines performed well with pipelines implementing DADA2 first having improved sequence fidelity (relatively lower error rates).

FIGS. 10A and 10B show example truth tables with computation of performance accuracy of the pipelines in detecting a condition for example a disease condition based on the differential abundance analyses. The truth table variables are as follows. True positives (TP): were when the analyses predicted yes (the subject(s) have the disease), and they do, in truth, have the disease. True negatives (TN): were when the analyses predicted no (the subjects do not have the disease), and in truth they don't have the disease. False positives (FP): were when analyses predicted yes, but they don't actually have the disease (a.k.a. "Type I error."). False negatives (FN): were counted when the analyses predicted no, but they actually do in truth have the disease (a.k.a "Type II error."). Positive predictive value (PPV) was computed as the proportion of positive results that are TRUE. Calculated as true positives/(true positive+false positive).

Figure 11A:
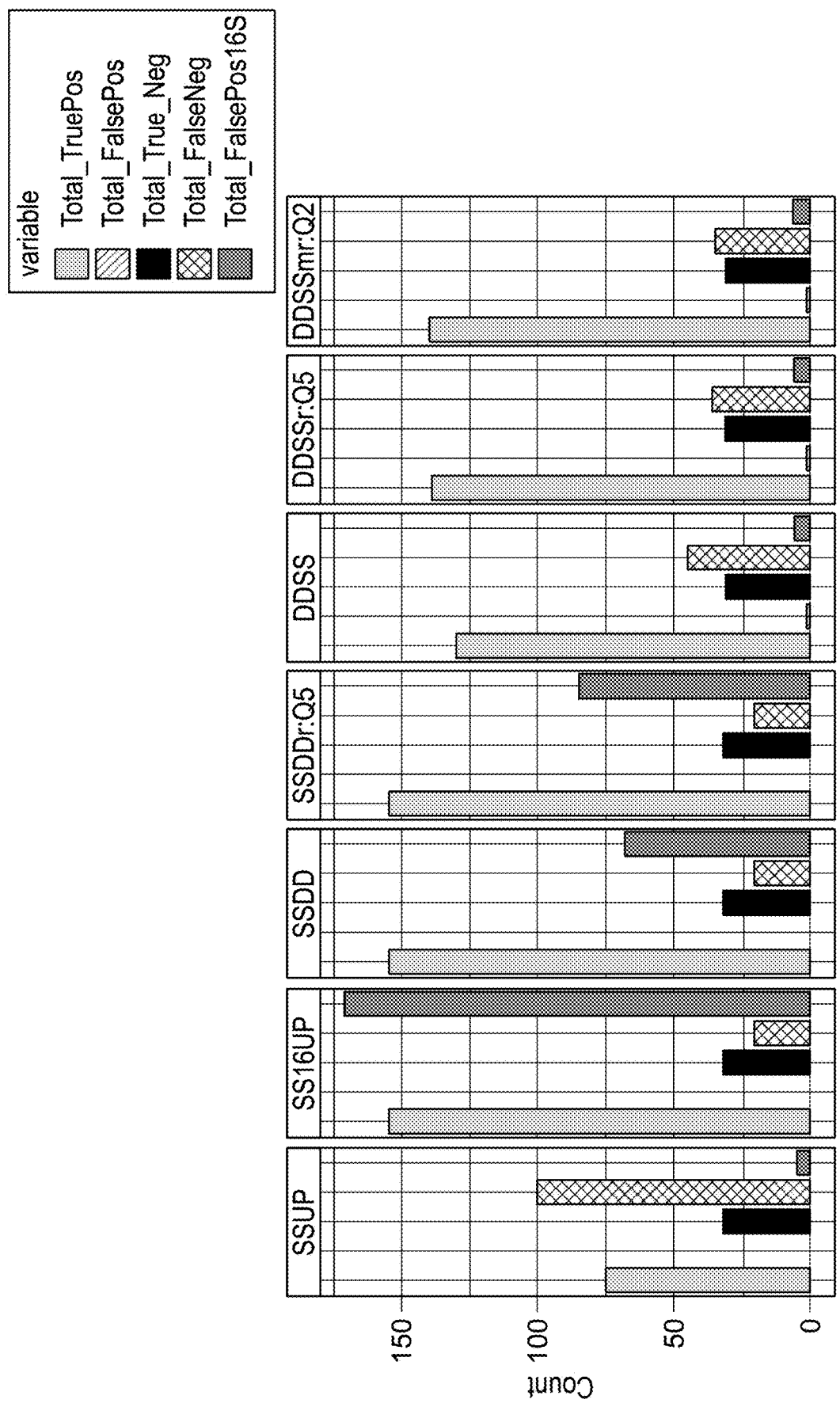
FIGS. 11A and 11B are example results from evaluation of workflow pipelines for differential abundance analyses, using a DAA system according to an embodiment.
Figure 11B:
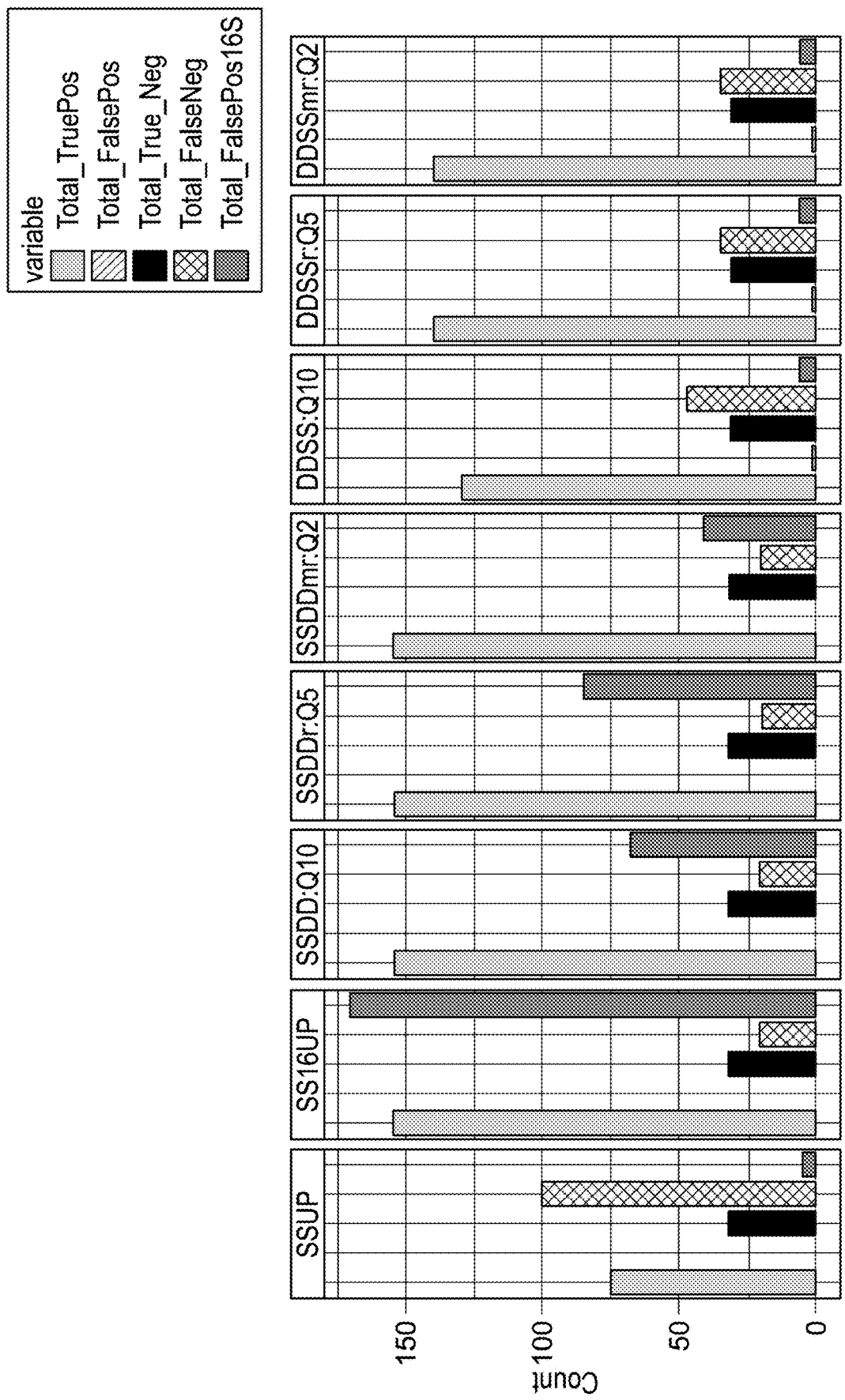
Figure 12A:
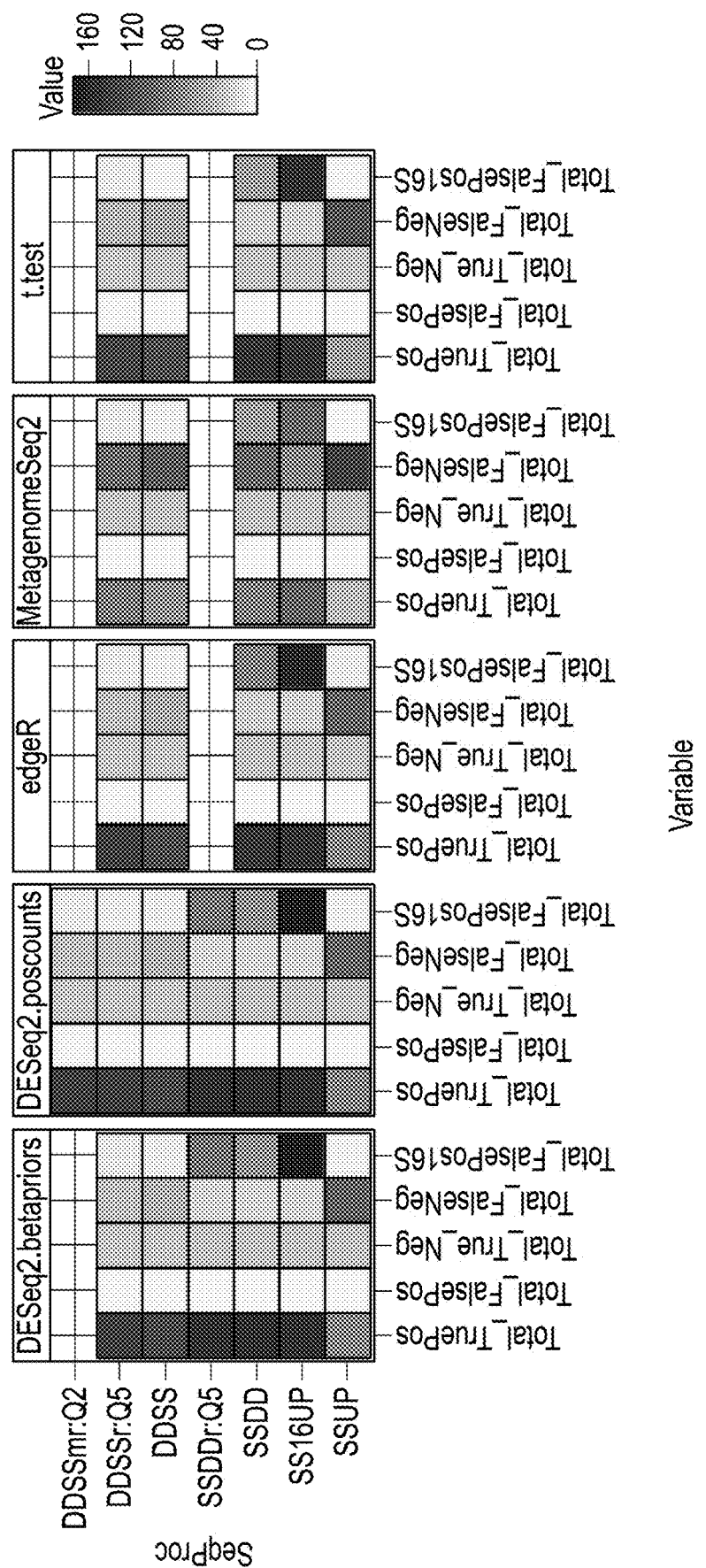
FIGS. 12A and 12B are a schematic representations of example results from evaluation of workflow pipelines for differential abundance analyses, using a DAA system according to an embodiment.
Figure 12B:
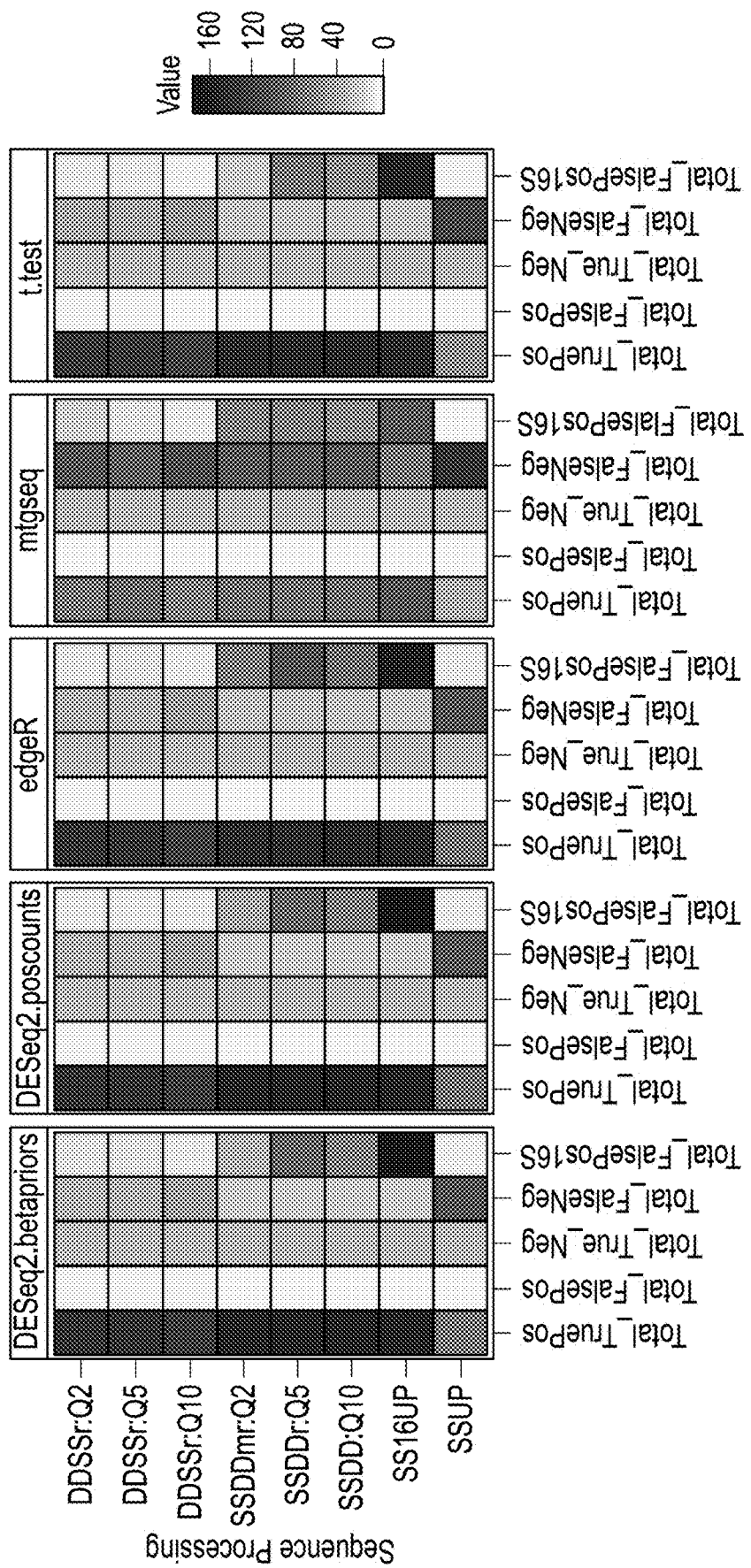
Figure 13A:
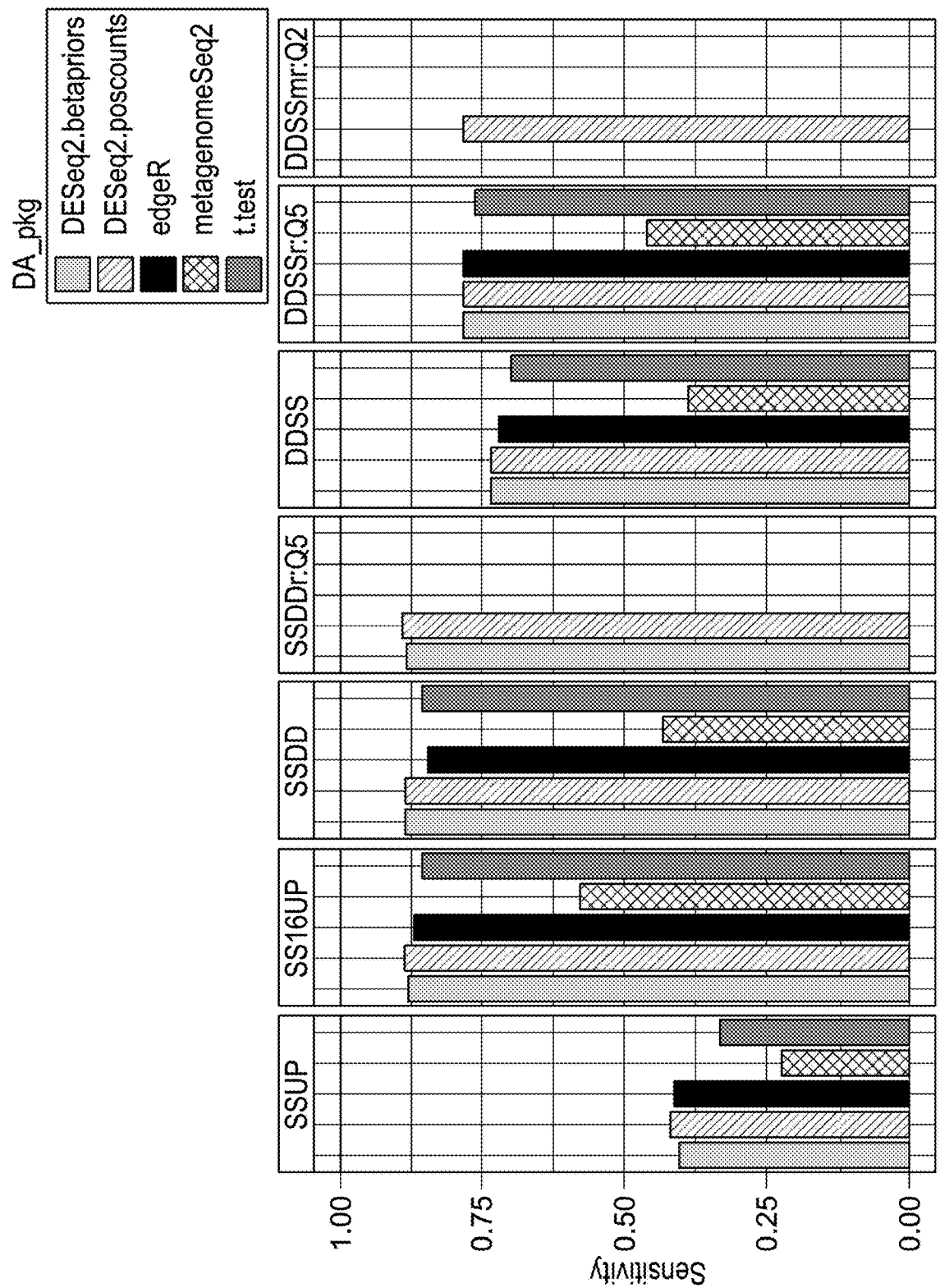
FIGS. 13A and 13B are example results from evaluation of workflow pipelines for differential abundance analyses using sensitivity as the evaluation metric, using a DAA system according to an embodiment.
Figure 13B:
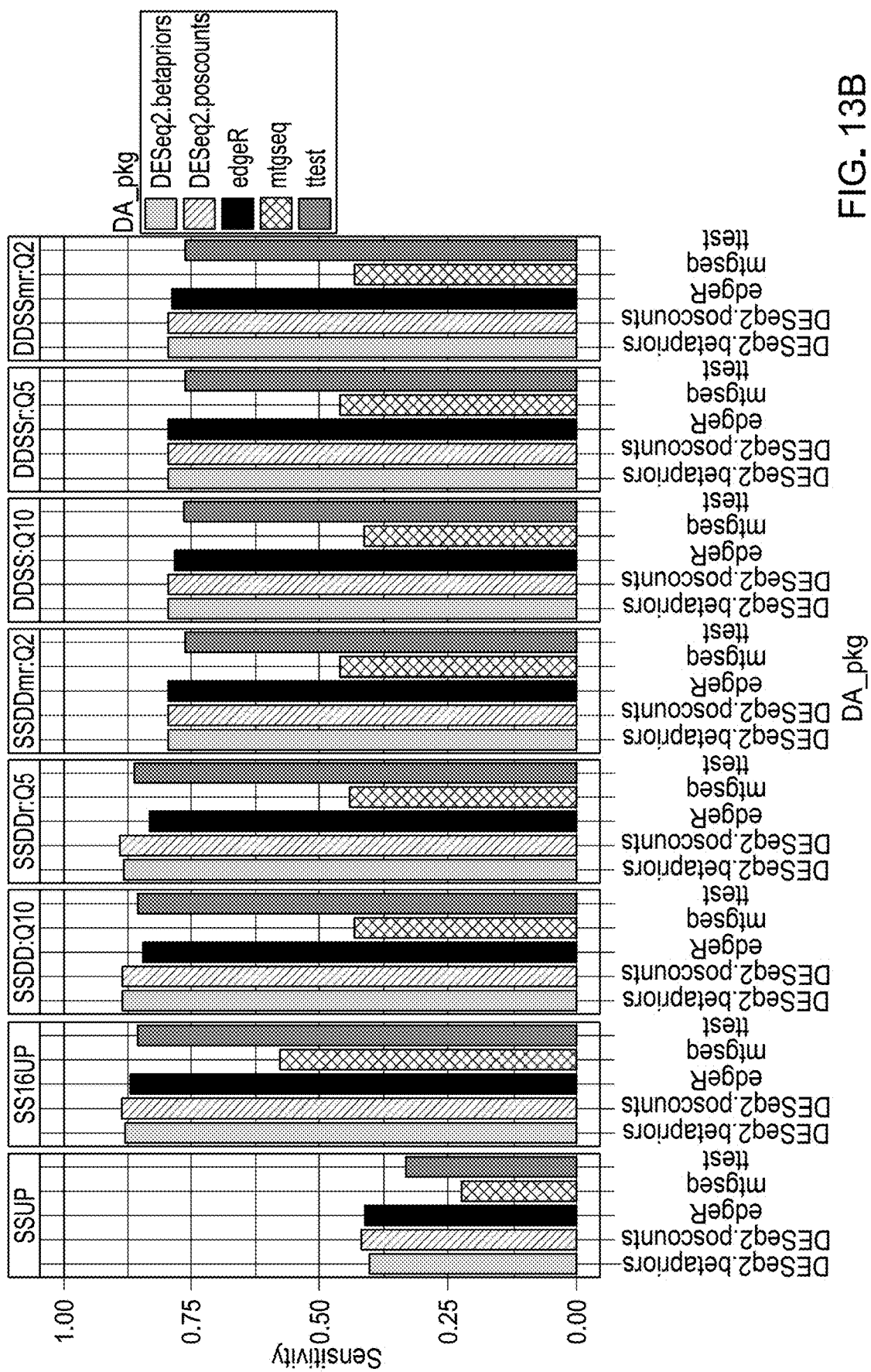
Figure 14A:
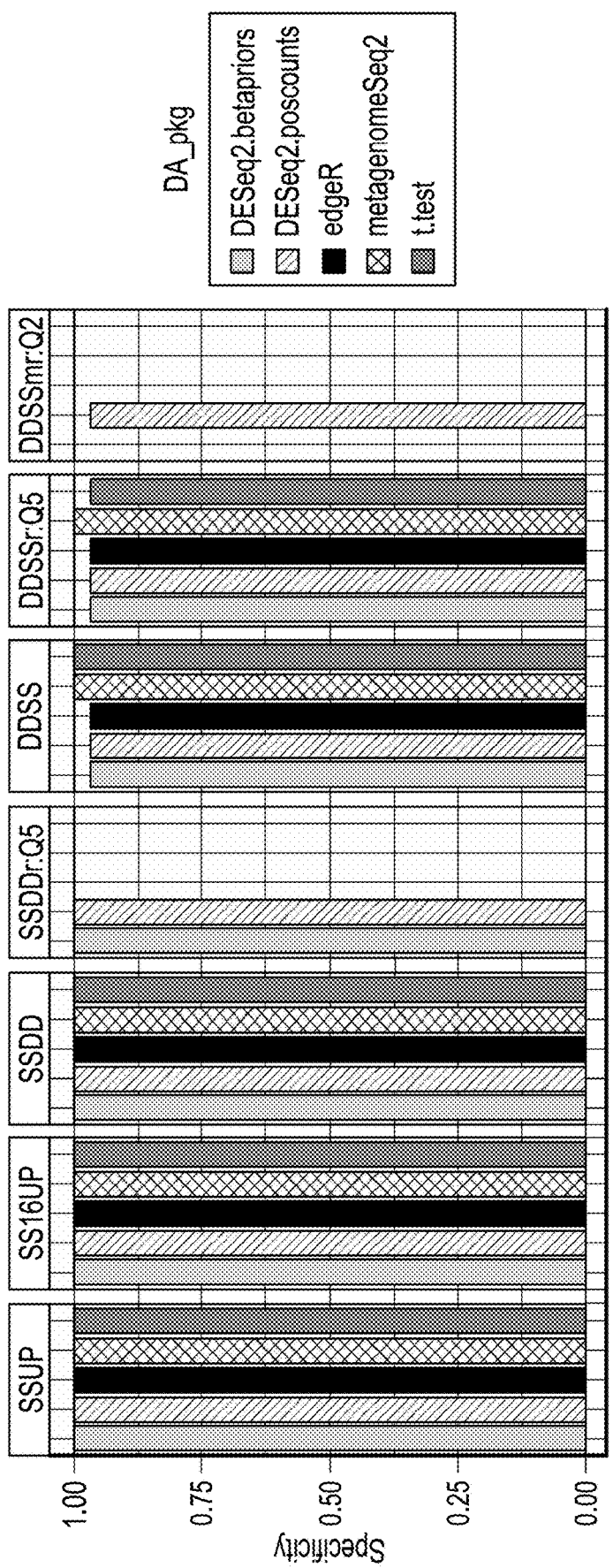
FIGS. 14A and B are an example results from evaluation of workflow pipelines for differential abundance analyses using specificity as the evaluation metric, using a DAA system according to an embodiment.
Figure 14B:
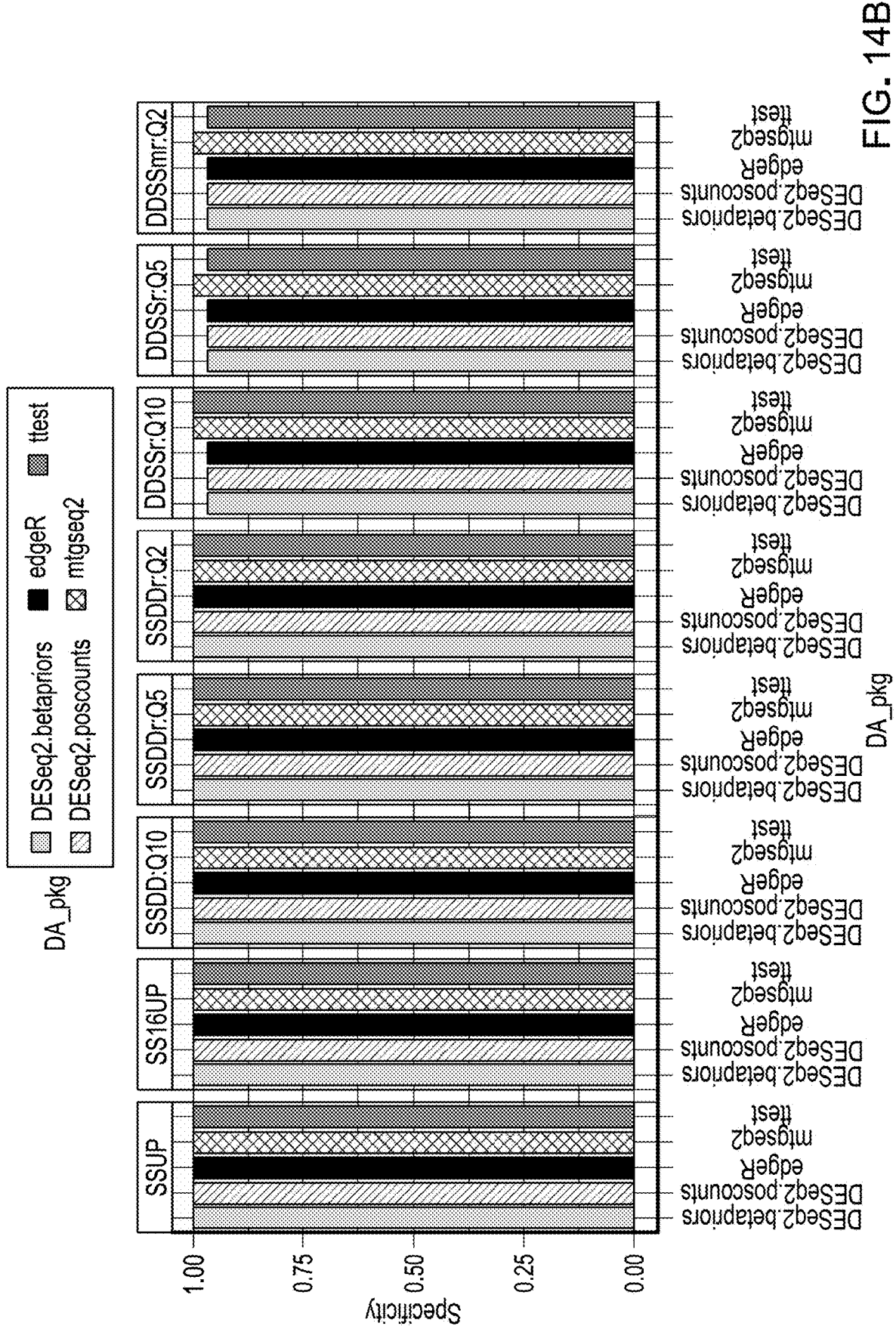
Figure 15A:
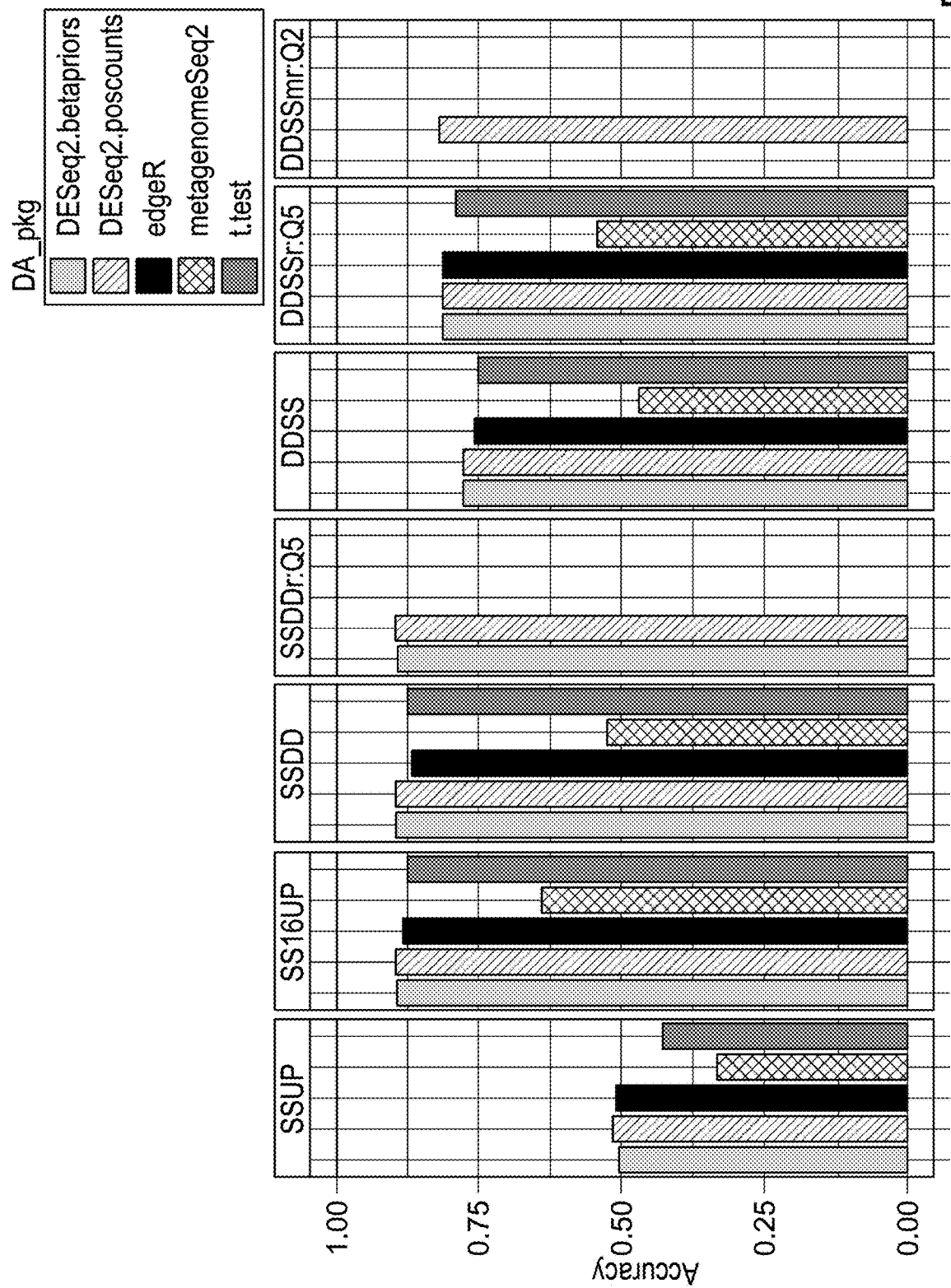
FIGS. 15A and B are an example results from evaluation of workflow pipelines for differential abundance analyses using detection accuracy as the evaluation metric, using a DAA system according to an embodiment.
Figure 15B:
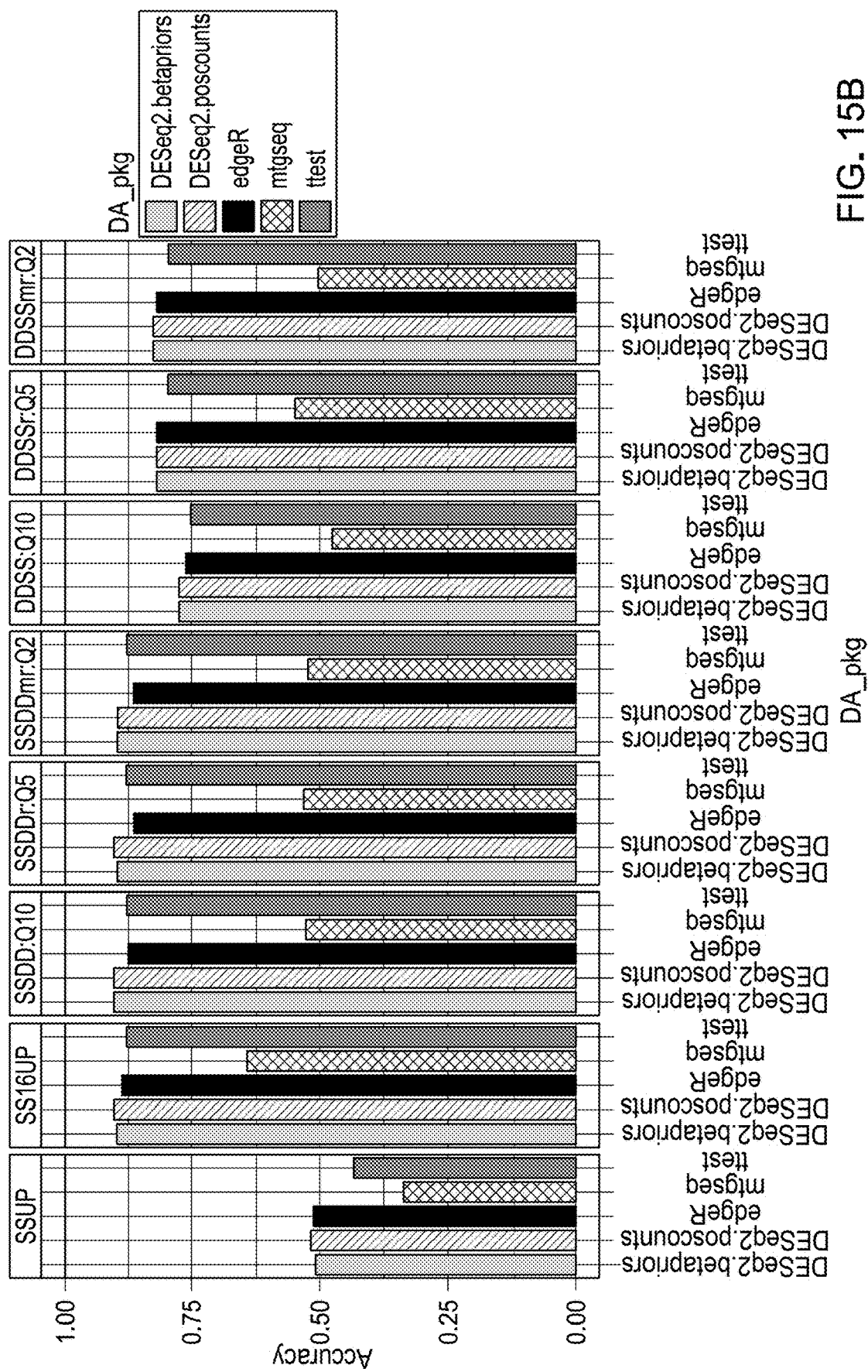

FIGS. 11A and 11B show plots of truth table variables for the pipelines including differential analysis by DESeq2.poscounts. Pipelines varied in the number of false positive 16S (Total_FalsePos16S) and false negative spikes (Total_FalseNeg). FIGS. 12A and 12B are schematic representations showing that false positives and false negatives in spike detection. FIGS. 13A and 13B are plots of sensitivity measures using the labelled workflow pipelines. True positive rate was used to measure sensitivity. That is, when the diagnosis is actually yes, how often the analysis predicts yes. Computed by TP/actual yes also known as "Sensitivity" or "Recall". SSDD and SSUP pipelines edged out DDSS pipelines in this metric of performance. FIGS. 14A and 14B show plots of specificity measuring the instances of when the diagnosis is actually no (no disease condition), and the frequency with which the analyses predicts no. Computed by TN/actual no, which is equal to (1−False Positive Rate). DDSS pipelines with DESeq2, edgeR, or t.test were less than 100% specific. FIGS. 15A and 15B are plots of accuracy measures of the various pipelines, measuring how often the model or analyses were correct. This was computed as (TP+TN)/total N. DESeq2 and edgeR achieved very similar accuracy within each sequence processing method.

Figure 16A:
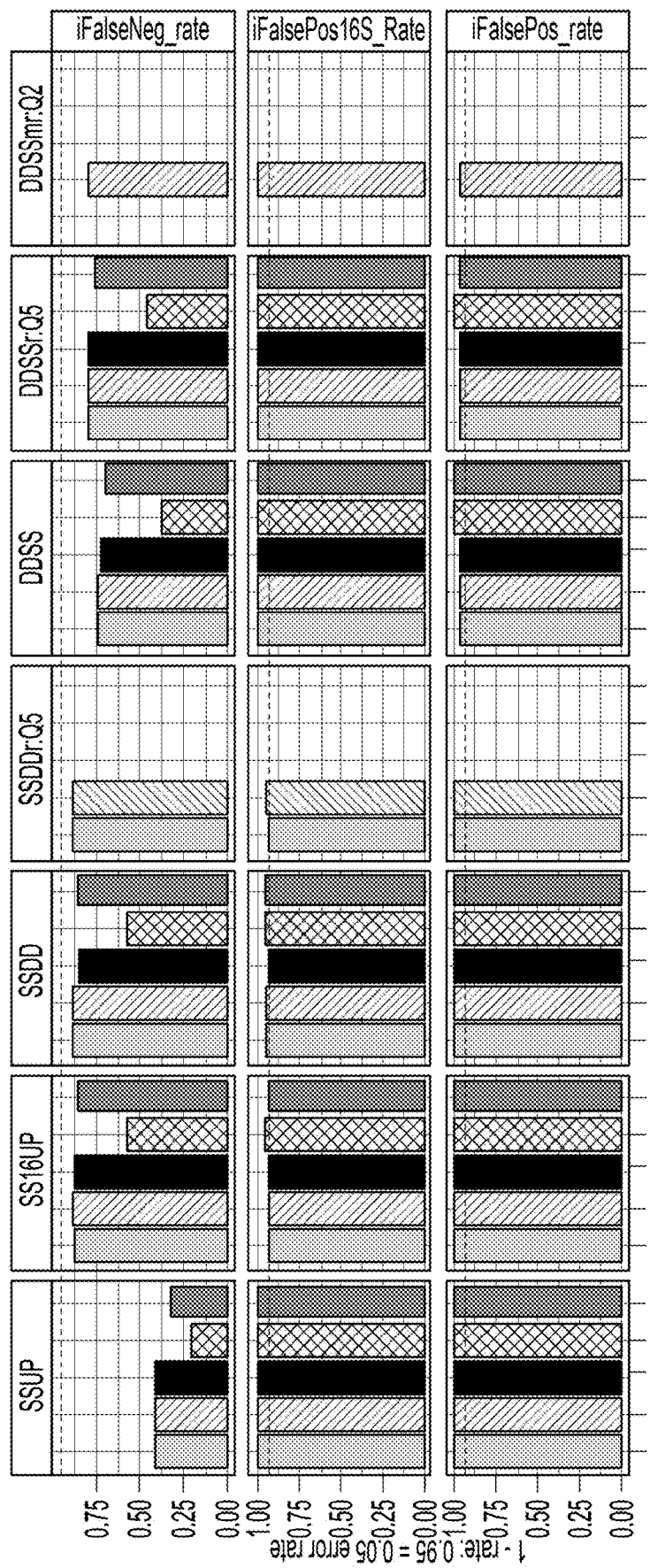
FIGS. 16A and 16B are plots of inverse error rates used for evaluation of workflow pipelines for differential abundance analyses, using a DAA system according to an embodiment.
Figure 16B:
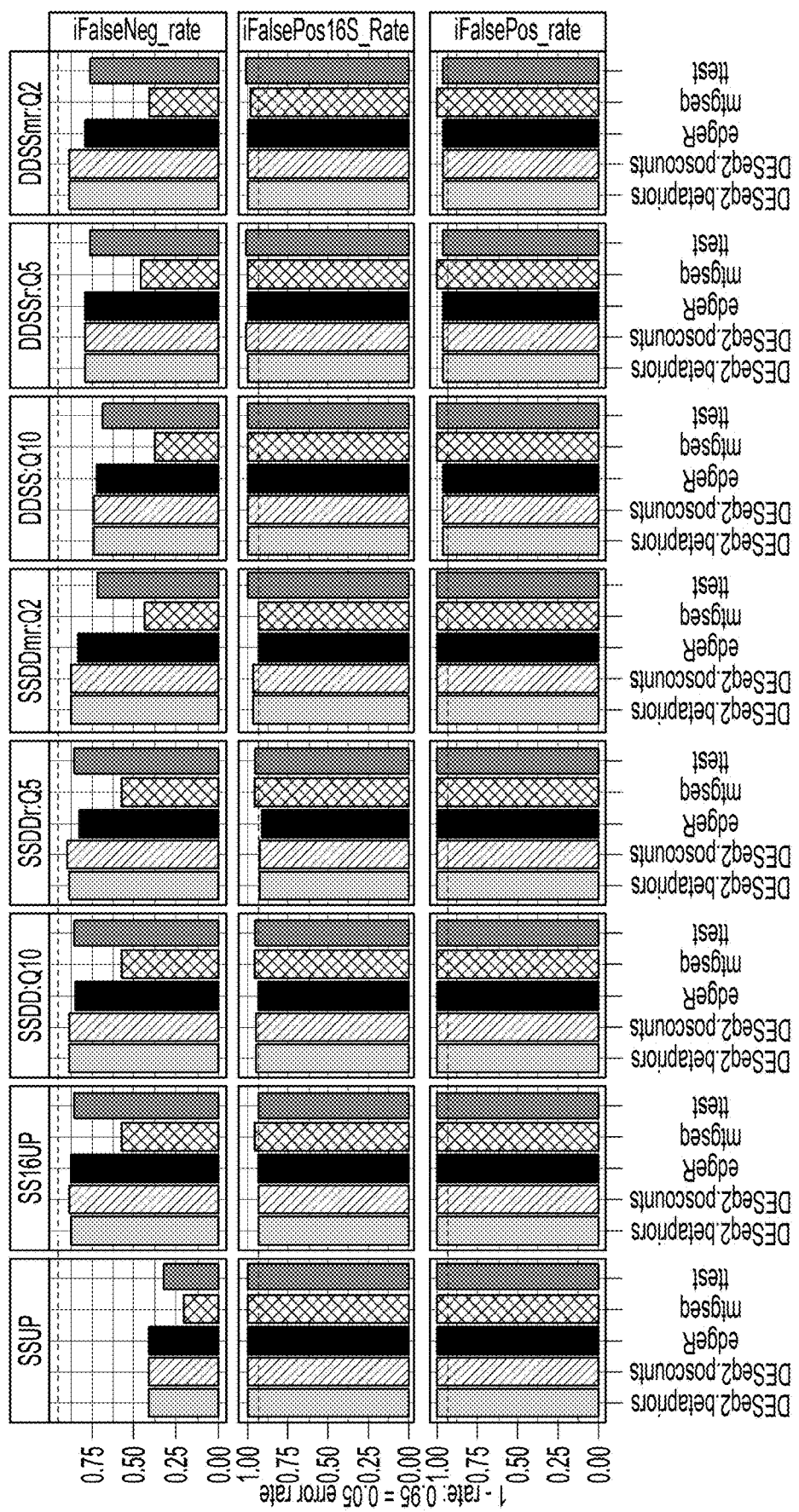
Figure 17A:
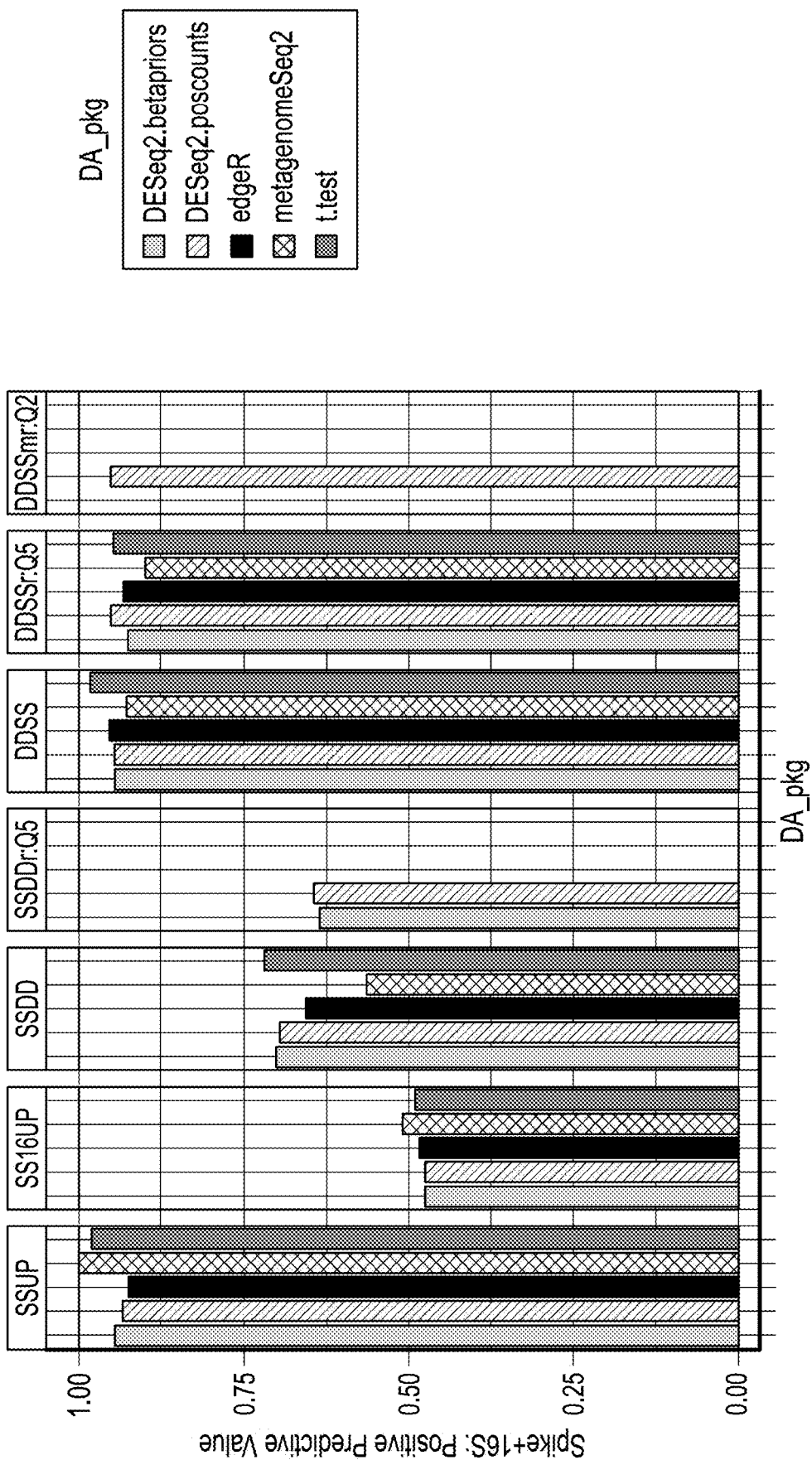
FIGS. 17A and 17B are plots of positive predictive value used for evaluation of workflow pipelines for differential abundance analyses, using a DAA system according to an embodiment.
Figure 17B:
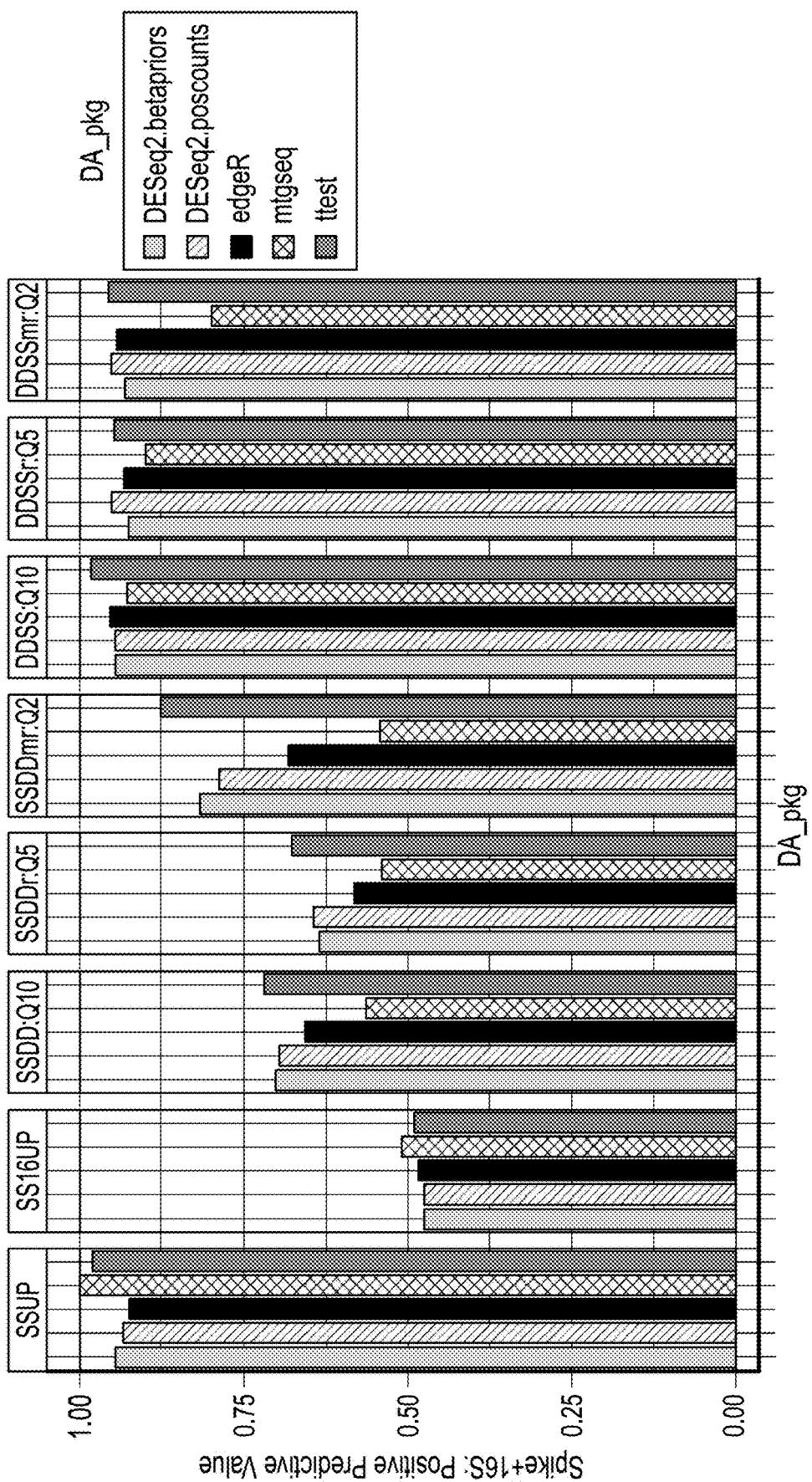

FIGS. 16A and 16B show plots of inverse false positive rates (iFalsePositive Rate) and inverse false negative rates. iFalse Positive Rate was calculated as the instances when the diagnosis is actually no, how often does the model or analysis predict yes. Computed as (1−(FP/actual no)). iFalse Negative Rate was calculated as the instances when the diagnosis is actually yes, how often does the analysis predict no. Computed as (1−(FN/actual yes)). As indicated all false positive rates were less than 0.05, when filtering DA results by padj<0.05. FIGS. 17A and 17B show plots of Spike+16S PPV, calculated as a count of instances when it's predicted yes, how frequently is it a true yes. Computed using the formula TP/(TP+FP+FP 16S). Spike+16S Positive Predictive Values were highest in DDSSx and SSUP, leading to more confidence in predicted hits.

Figure 18A:
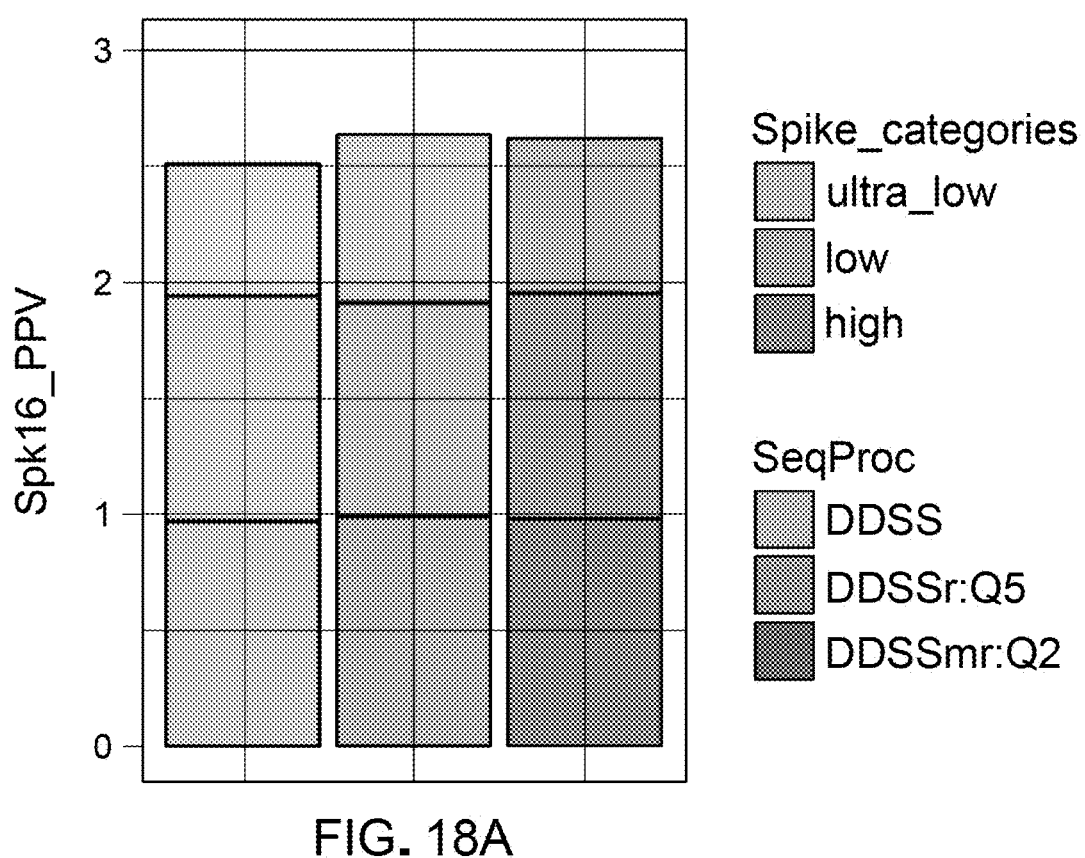
FIG. 18A is a plot of positive predictive value, categorized by relative levels of abundance, used for evaluation of workflow pipelines for differential abundance analyses, using a DAA system according to an embodiment.

As described above, the evaluation of differential abundance analyses pipelines can be carried out by also considering the performance in categories subdivided by the relative abundance of the spike templates. FIG. 18A shows a quantification if Spike+16S PPV, calculated as a count of instances when it's predicted yes, how frequently is it a true yes, while also considering abundance of the spikes. Computed as TP/(TP+FP+FP_16S) within each category of spike abundance levels. As shown Spike+16S Positive Predictive Values were nearly 1 (max) for the high and low abundance spikes. Ultra low spikes had improved performance with the 'relaxed' and 'more relaxed' pipelines. The table in FIG. 18B lists the category of spikes based on relative abundance and the corresponding Spike16_PPV values.

Figure 19A:
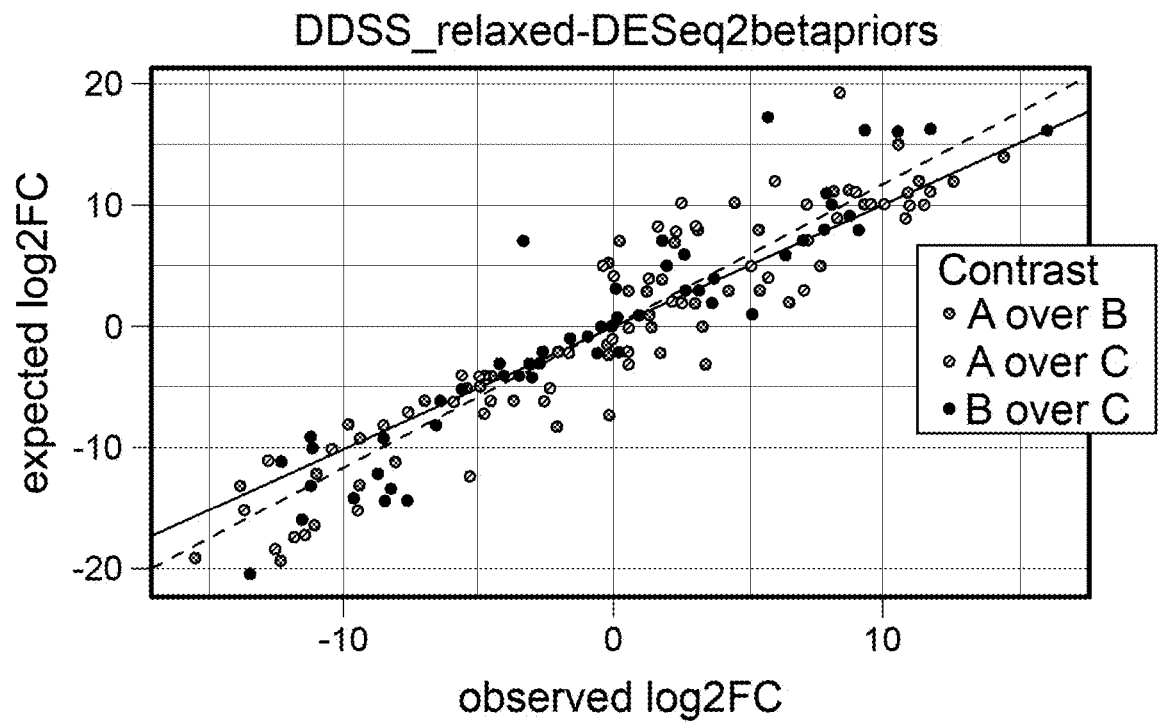
FIGS. 19A and 19B are schematic representations of quantified differences between expected and observed results of differential abundance analyses using a DAA system according to an embodiment.
Figure 19B:
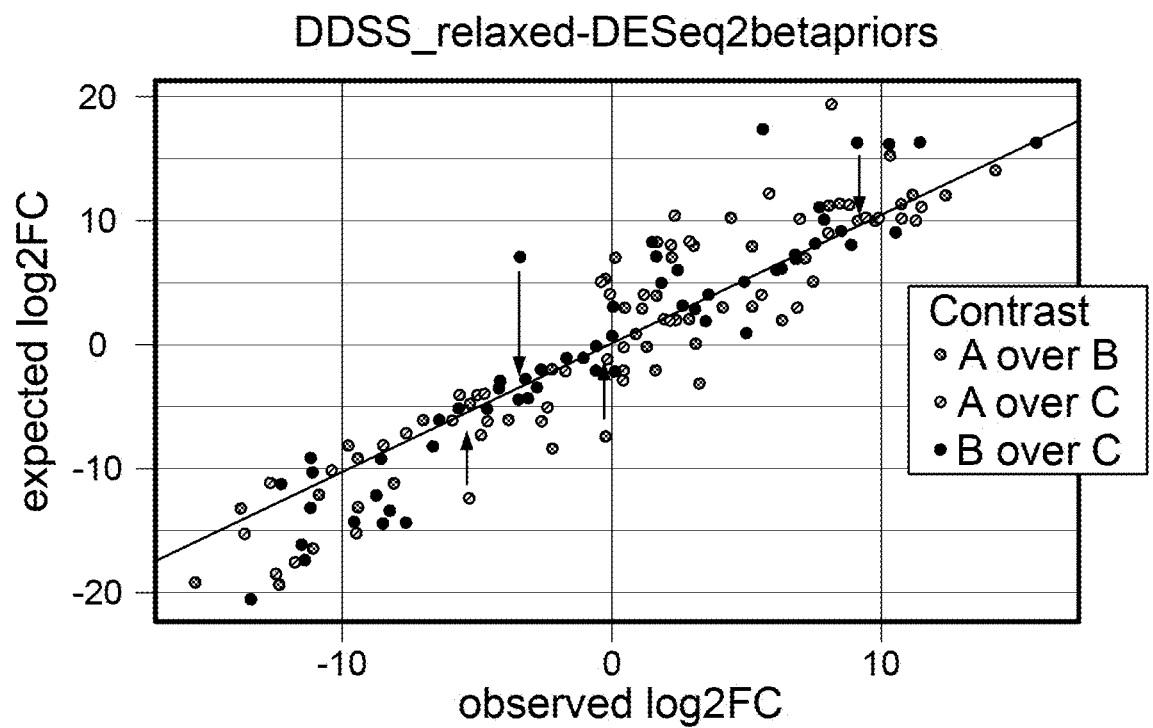
Figure 20A:
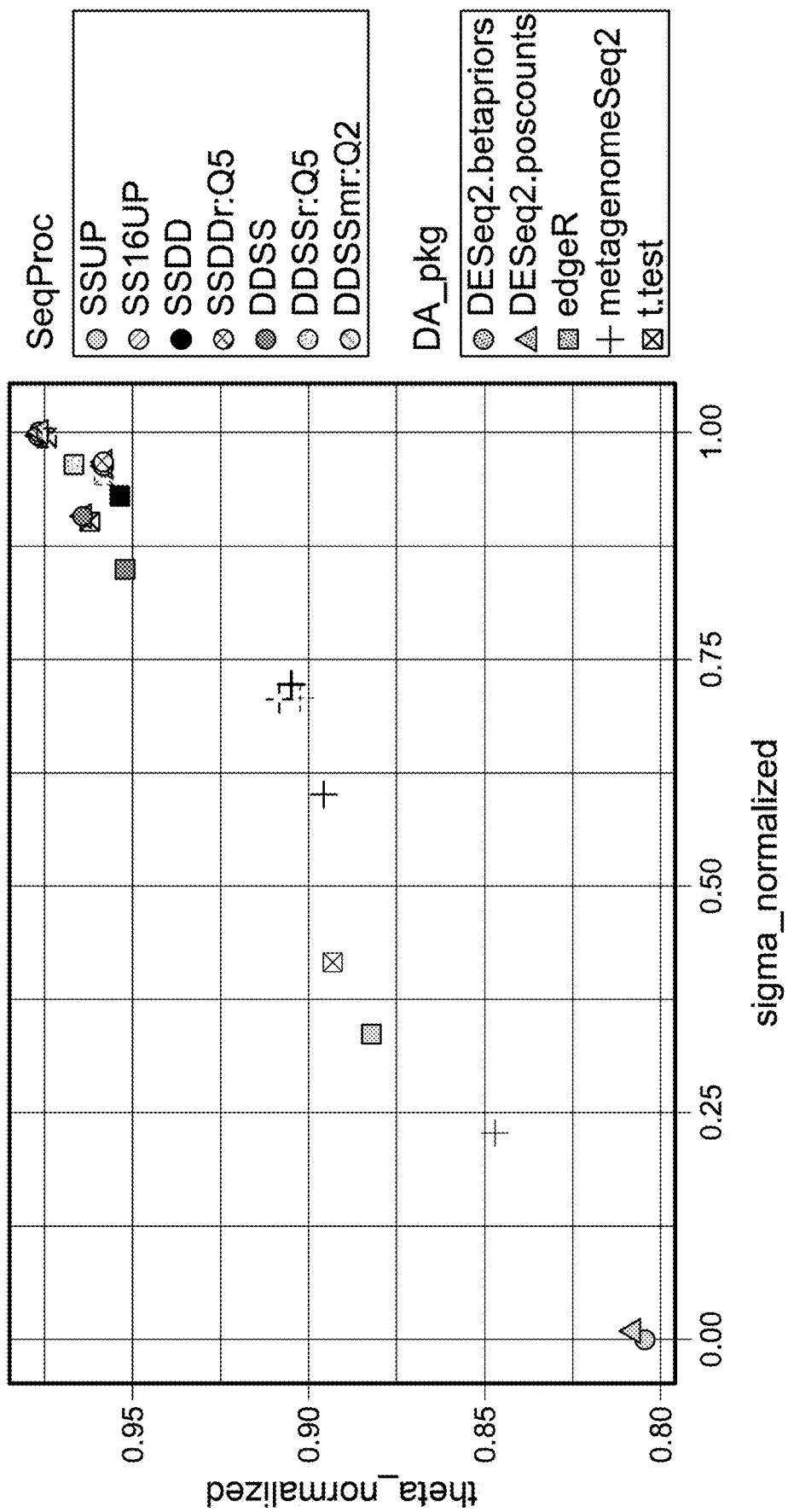
FIGS. 20A and 20B are schematic representations of results from evaluating pipelines for differential abundance analyses using a DAA system according to an embodiment.
Figure 20B:
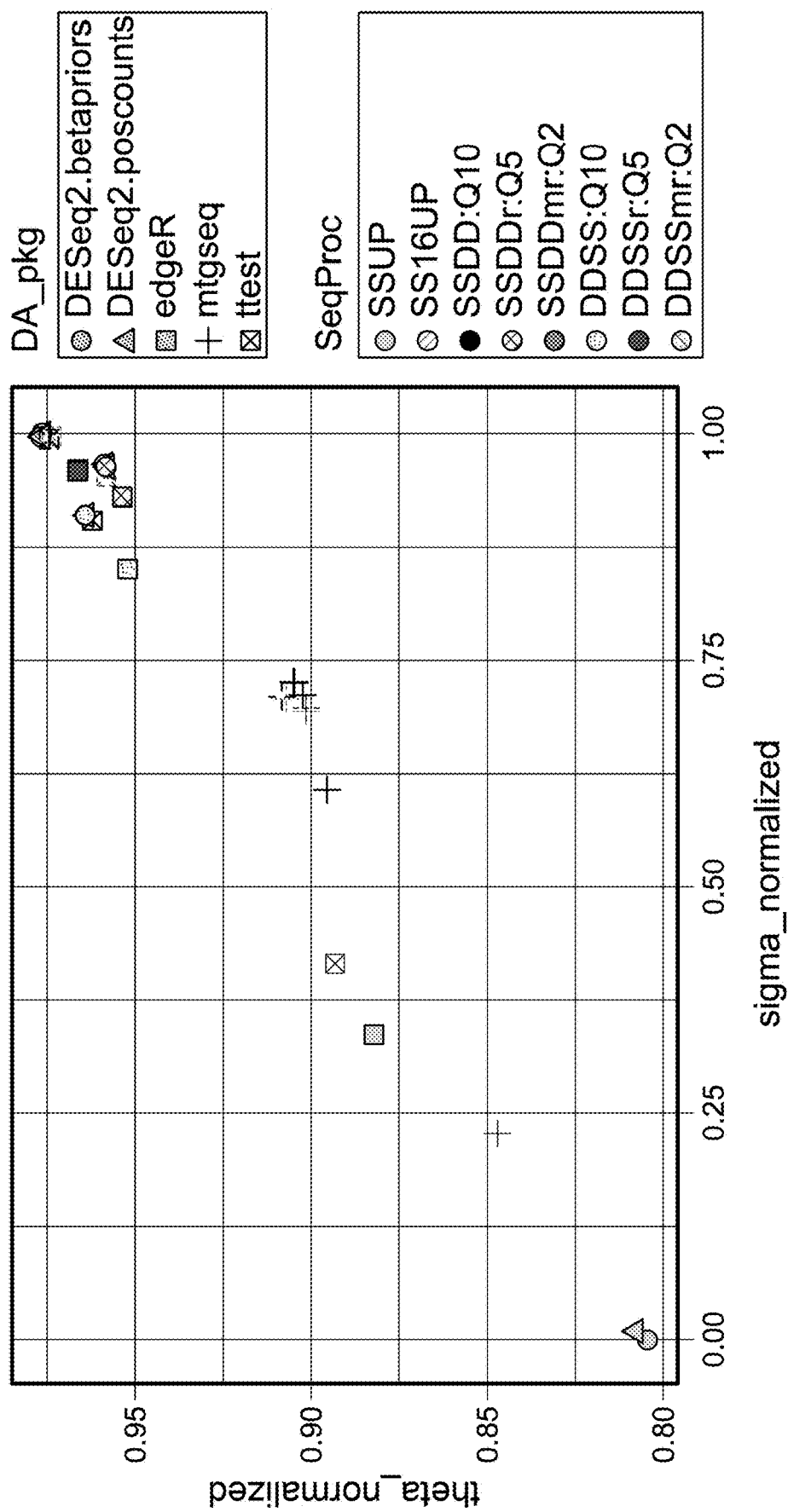

FIGS. 19A and 19B are plots of values sigma and theta, respectively, used to assess the accuracy of the calculated differential abundance for each OTU or ASV. The distribution shows a plot of expected counts against observed counts of spikes. Theta is computed as the angle between the fitted line of points and the expected log 2FC (a line of slope=1) [in degrees]. Inverse, normalized theta is computed as (1−(theta/180°)). Sigma is computed as the residual standard error of points from the expected log 2FC (a line of slope=1), indicated by arrows in FIG. 19B. Values were scaled 0-1. Inverse, normalized sigma was computed as (1−(scaled sigma value)). FIGS. 20A and 20B are plots of the inverse of theta and sigma values. By plotting the inverse, the smaller values (better values, in this example) are shown in the top right corner. DDSS pipelines outperformed the SSDD pipelines. DDSS pipeline performance improved as quality threshold was reduced.

Figure 21A:
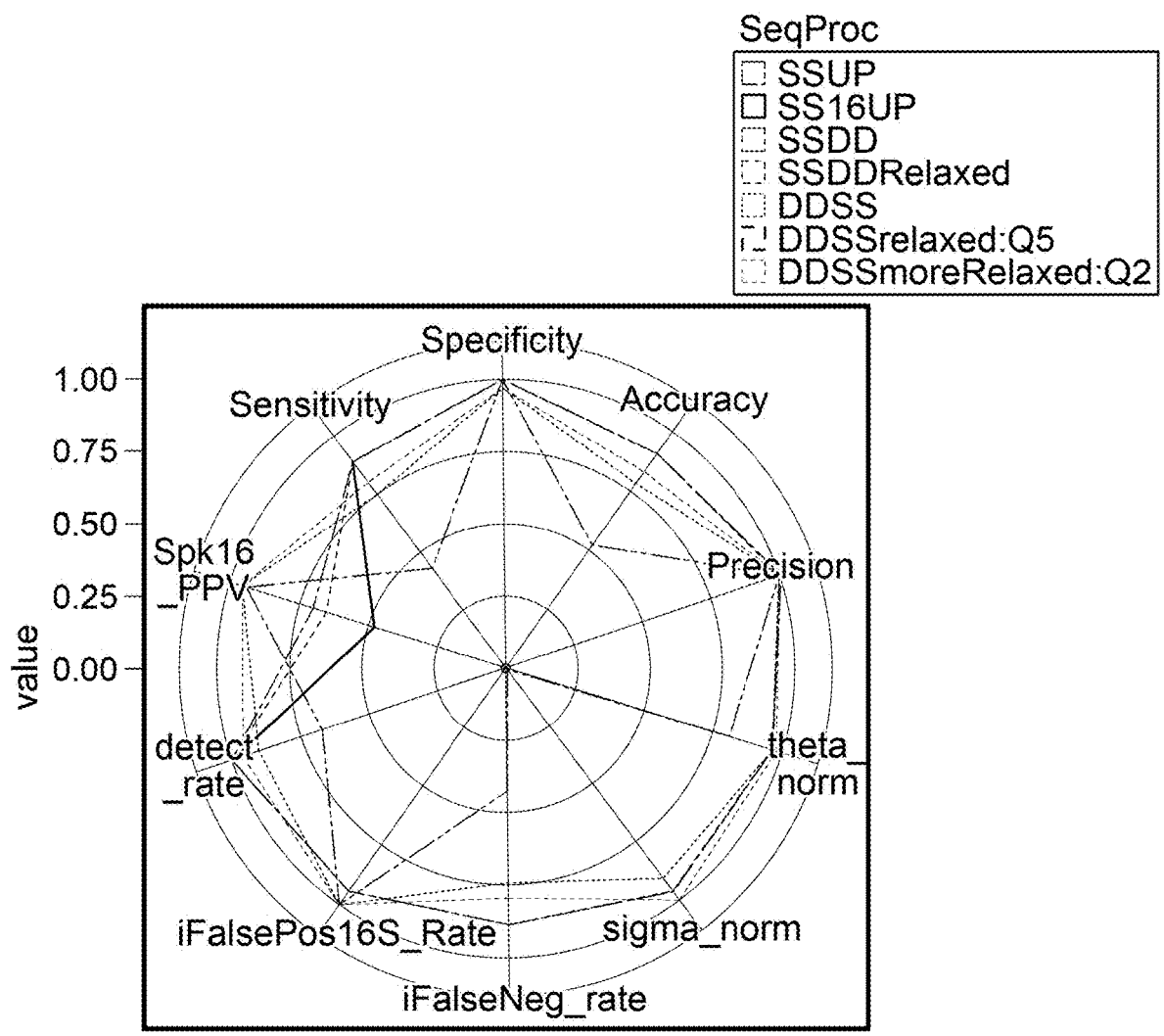
FIGS. 21A and 21B are schematic representations of results from evaluating pipelines for differential abundance analyses, quantified by multiple evaluation parameters, using a DAA system according to an embodiment.
Figure 21B:
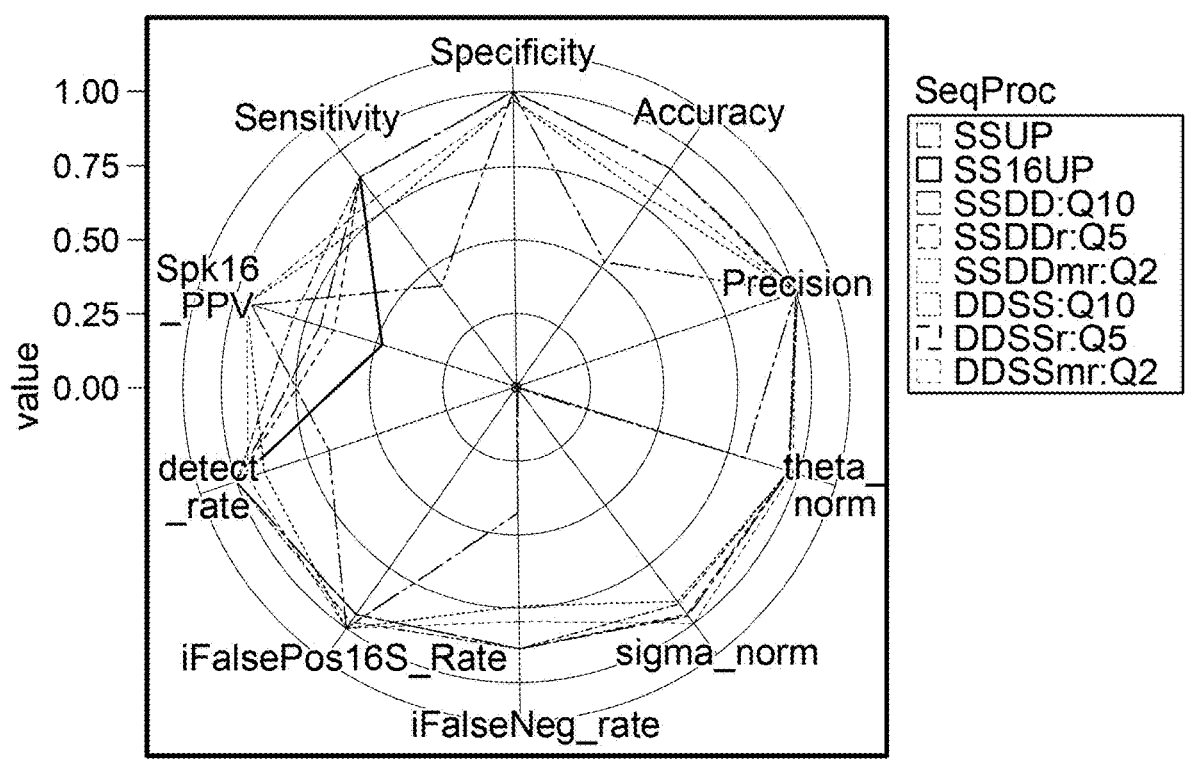
Figures 23A, 23B, 23C:
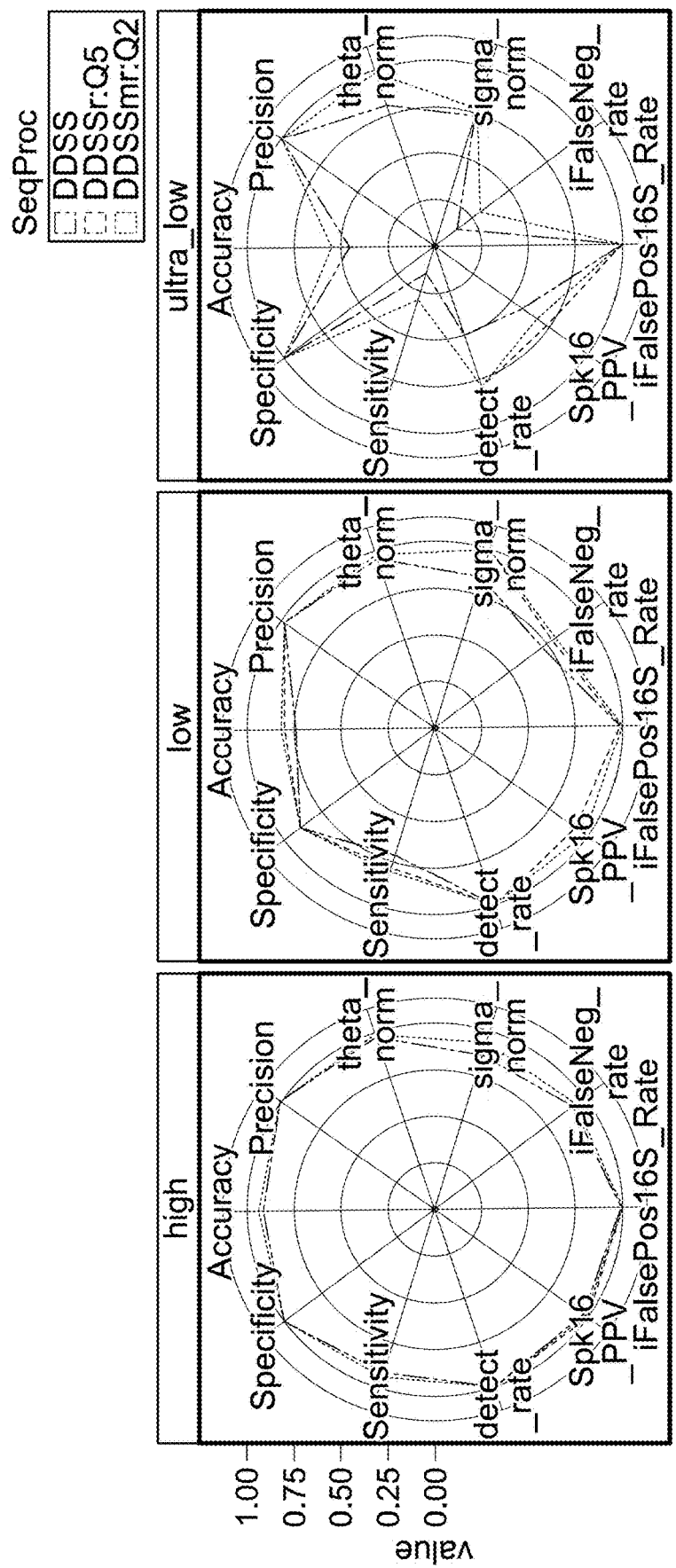
FIGS. 23A-C are a set of schematic representations of results from evaluating pipelines for differential abundance analyses, quantified by multiple evaluation parameters, using a DAA system according to an embodiment.
Figure 24A:
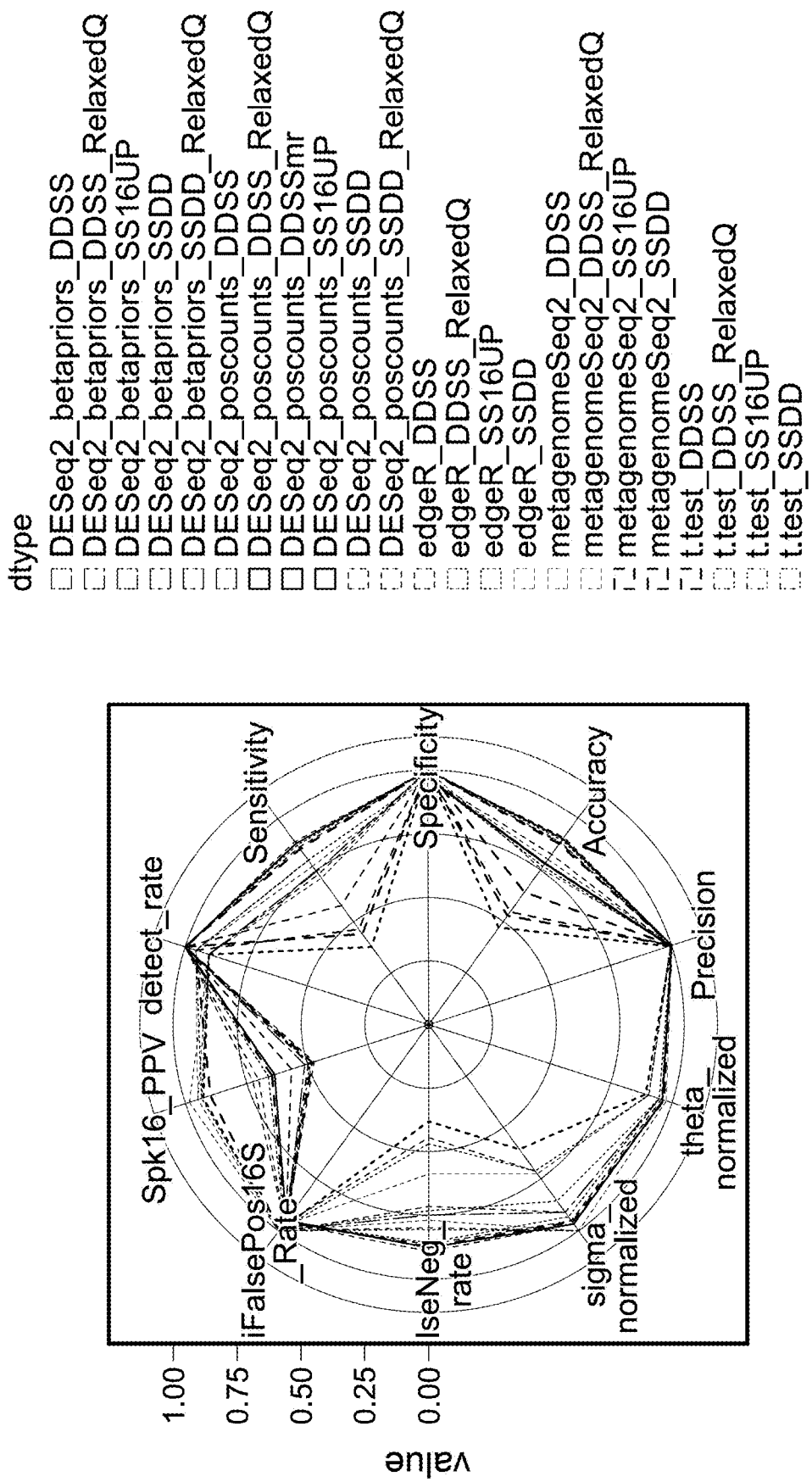
FIGS. 24A and 24B are additional schematic representations of results from evaluating pipelines for differential abundance analyses, quantified by multiple evaluation parameters, using a DAA system according to an embodiment.
Figure 24B:
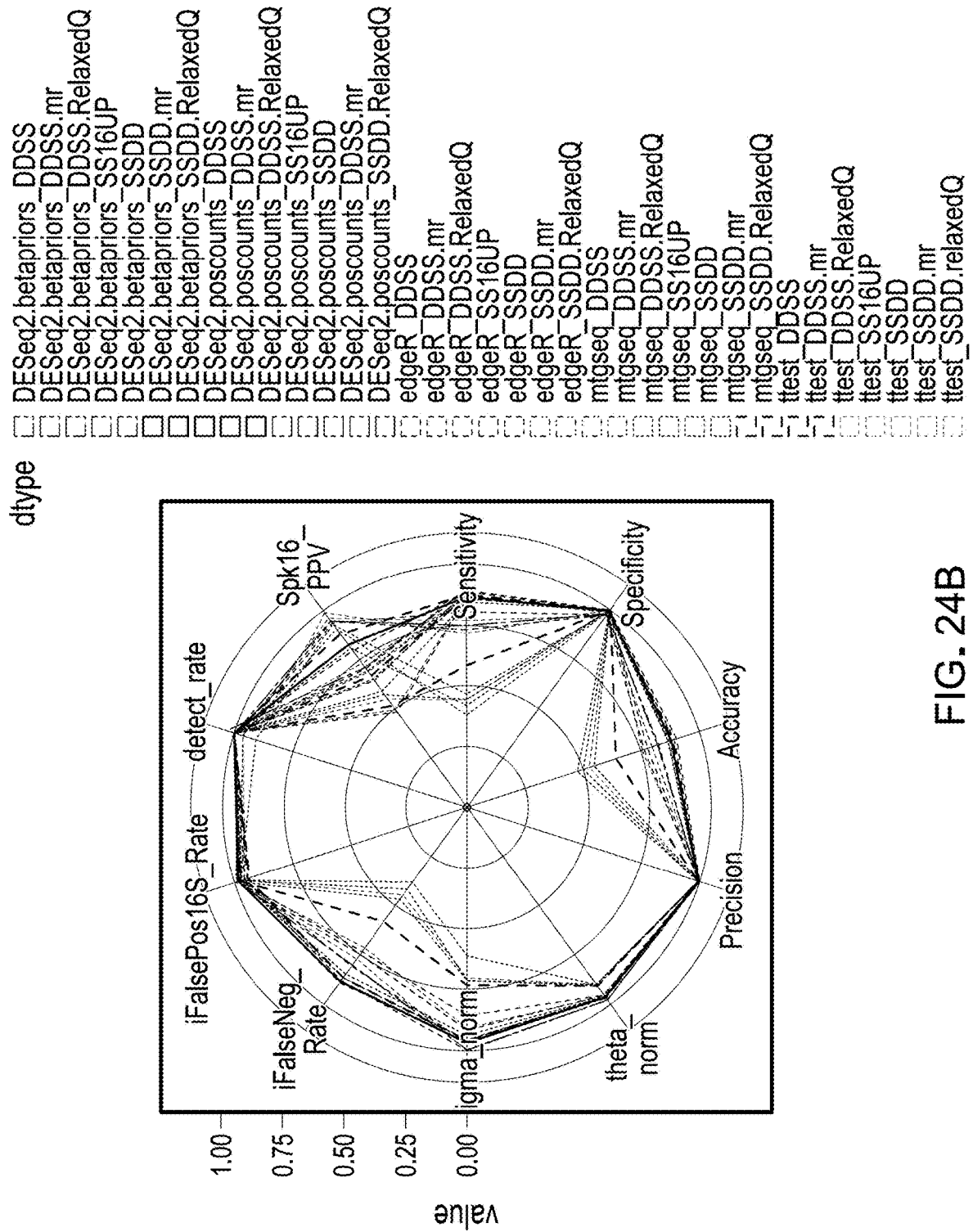
Figure 25A:
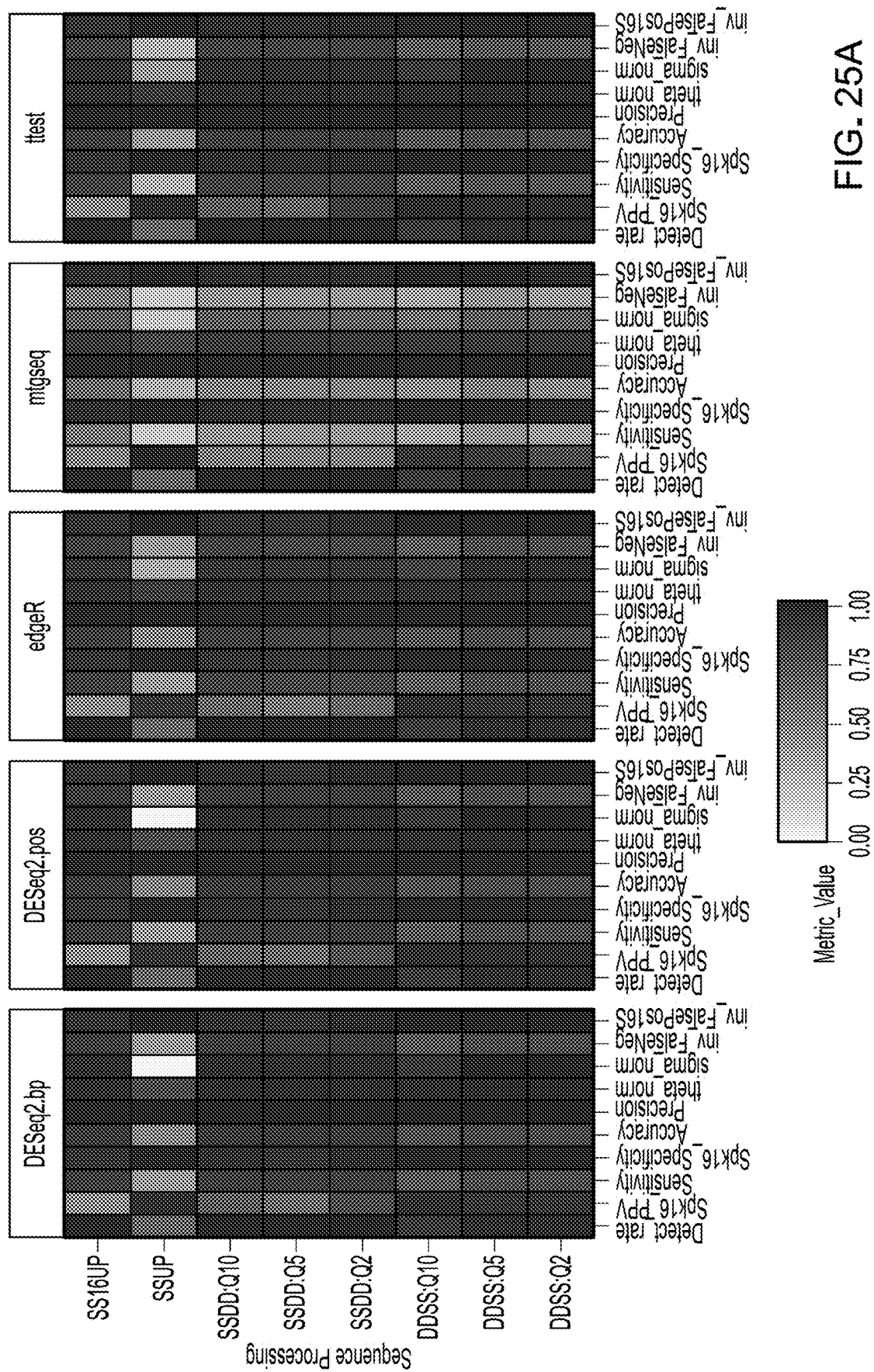
FIGS. 25A and 25B are additional schematic representations of results from evaluating pipelines for differential abundance analyses, quantified by multiple evaluation parameters, using a DAA system according to an embodiment.
Figure 25B:
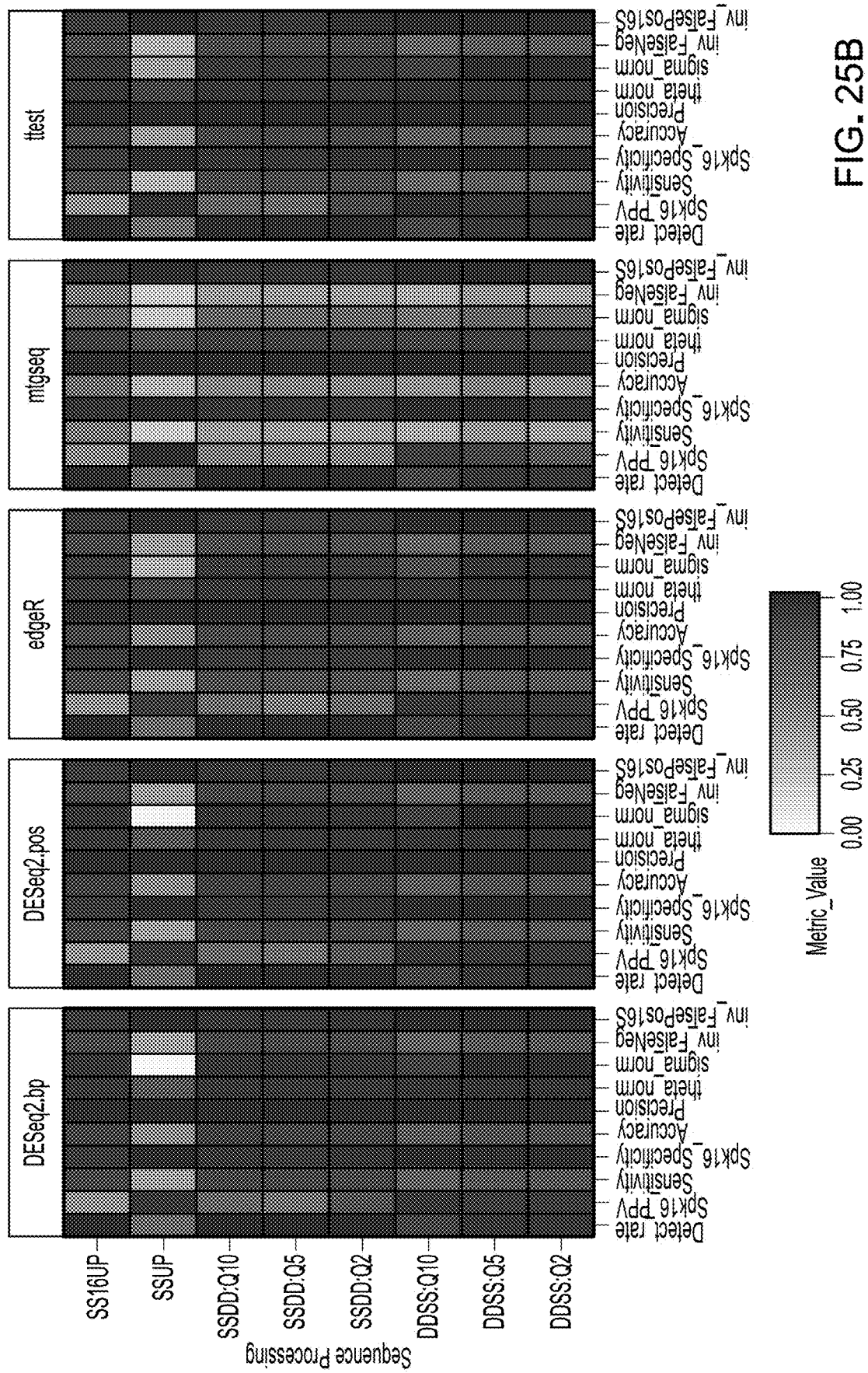

FIGS. 21A and 21B are plots of performance of the pipelines using several metrics including sensitivity, specificity, accuracy, precision, theta-norm, sigma-norm, detection rate, Spike16_PPV, etc., each metric being represented by a vertex of the polygon plot. The plot shows results for pipelines using differential analysis using DESeq2.poscounts, each pipeline indicated by a colored line. FIGS. 22A and 22B are tables showing a ranking of the pipelines based on scores associated with the performance of each pipeline. DDSSmr:q2+DESeq2 ranked highest with added weight on Spike16_PPV (SG preference). FIGS. 23A-23C show polygon plots representing performance of pipelines categorized by the relative abundance of the spikes, with FIGS. 23A, 23B and 23C representing performance of pipelines for spikes of high abundance, low abundance and ultra-low abundance, respectively. The plots show evaluation of differential analyses pipelines using DESeq2.poscounts. DDSSmr:q2 pipeline balances all metrics, for high and low abundance spikes. FIGS. 24A and 24B illustrate plots evaluating performance of pipelines using all the tested statistical analyses tools. Workflow pipelines performed unevenly, particularly on accuracy, sensitivity and Spike16_PPV, with 1 being a perfect score for all metrics. As described previously i=inverse for FalsePos and FalseNeg rates. FIGS. 25A and 25B are schematic representations of performance of the workflow pipelines on a color scaled map. As indicated in FIG. 24, workflows performed unevenly, particularly on accuracy, sensitivity and Spike16_PPV.

Example Applications of this Technology:

The described systems and methods can be used to generate internal standard spike-in mixes and use the mixes to evaluate a vast range of workflow pipelines using several measures or metrics of performance as described herein. By comparing expected results (based on known levels of spikes in mixes used) and observed results obtained using the various pipelines one can choose a workflow pipeline that best suits the needs of a study of research protocol. For example, studies sensitive to accuracy and detection sensitivity can used those metrics to pick the pipeline whereas studies that can tolerate lower detection rates but need low false positive rates can chose based on false positive rates. They can also select an overall high-ranked pipeline as described in the example above.

Once a particular pipeline is chosen the validation systems and methods described herein also provide an internal control for the validity of results obtained using that pipeline for a specific study. For example, the results obtained based on sparse data can be of variable robustness and reproducibility. As an example, in a typical RNA-Seq experiment from a single organism, between 15 to 85% of an organism's genes are observed in any one biospecimen. As another example, in a microbiome NGS experiment, the data tables are much sparser with only 1 to 3% of the study's cumulative features encountered in any one biospecimen. Using the systems and methods described herein, one can use the same spike in mixes that were used to select a pipeline for analysis in combination with test specimens when running the study. For example, in a blind study of samples from a group of normal and diseased spike-mixes can be randomly allotted and documented. The workflow pipeline can be followed as before. The results can be drawn for detection of spikes as well as detection of target genes or RNA sequences of interest. Results of spikes can be categorized based on their known relative abundance levels in the spike mixes used with each sample (which is documented and known) and the results of the categories of spikes based on abundance levels can be compared to results of the target sequences based on their abundance levels. For example, if performance of the pipeline measured using a particular metric (e.g. sensitivity) is significantly lower for spikes with ultra-low abundance this measure of results for the target sequences can be disregarded due to lack of statistical confidence in performance of the pipeline. Whereas in instances where the performance of the pipeline is measured to be superlative even for the spikes with ultra-low abundance, from a comparison of expected and observed results for the spikes in the spike-in mixes, the results obtained using the same pipeline for target sequences tested in the samples can be taken with high confidence even for the target sequences that are of ultra-low abundance. Thus the systems and methods described herein provide an internal control that can be used to weigh the significance of results for the target sequences with ultra-low abundance that may otherwise be difficult to quantify and be used to design critical diagnosis or treatment strategies based on the results.

Figure 26:
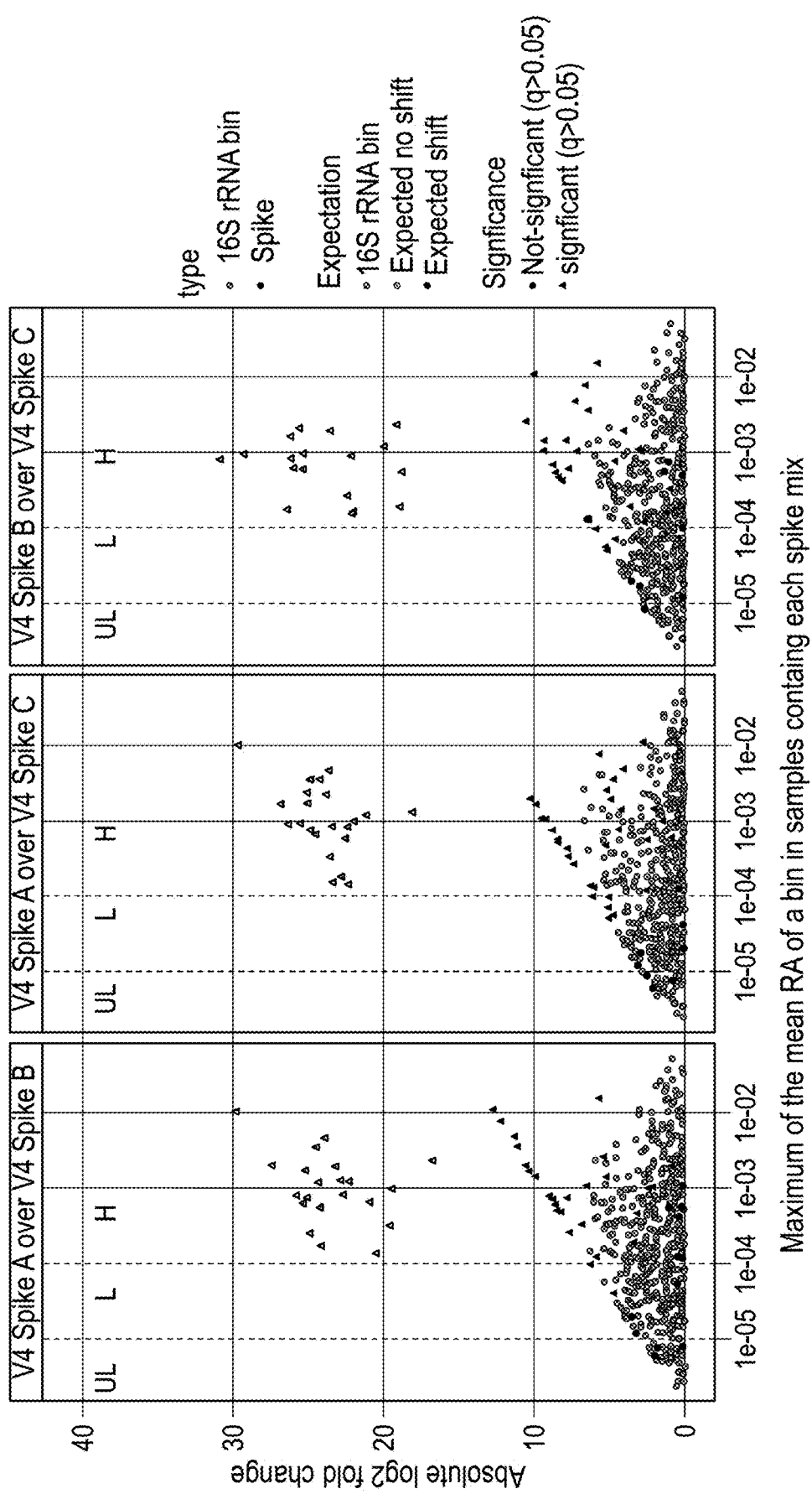
FIG. 26 is an example result from estimation of PPV and miss rate for spikes based on their abundance.

In some embodiments, spike mix can be added to stool samples collected at baseline from patients with different diseases or patients receiving checkpoint inhibitor therapy (e.g., melanoma subjects undergoing checkpoint inhibitor therapy). Based on the relative abundance of the spikes in samples, a spike was designated as high (H)-, low (L)- or ultra-low (UL) abundance spike as shown in FIG. 26. Statistical measures, e.g., positive predictive value (PPV) and miss rate (MR), can be calculated based on how many of the expected shifts (illustrated as black colored points in FIG. 26) were recovered as significant shifts (illustrated as triangular points in FIG. 26) in the analysis. PPV is the ratio of true positive to true positive+false positive and provides an indication of what proportion of the significant shifts detected are high confidence shifts. In this example, for high & low-abundance shifts, PPV=1 was observed which indicates that there is high confidence in these shifts. Since no ultra-low abundance spikes were detected, PPV could not be estimated in this example. Miss rate can be calculated at as the rate of not detecting or identifying an expected shift as significant. In this example, for high abundance shifts, the miss rate was 14.4%, 46.6% for low abundance shifts and 100% (i.e. all shifts in ultra-low abundance spikes were missed) for ultra-low abundance spikes.

Figure 27:
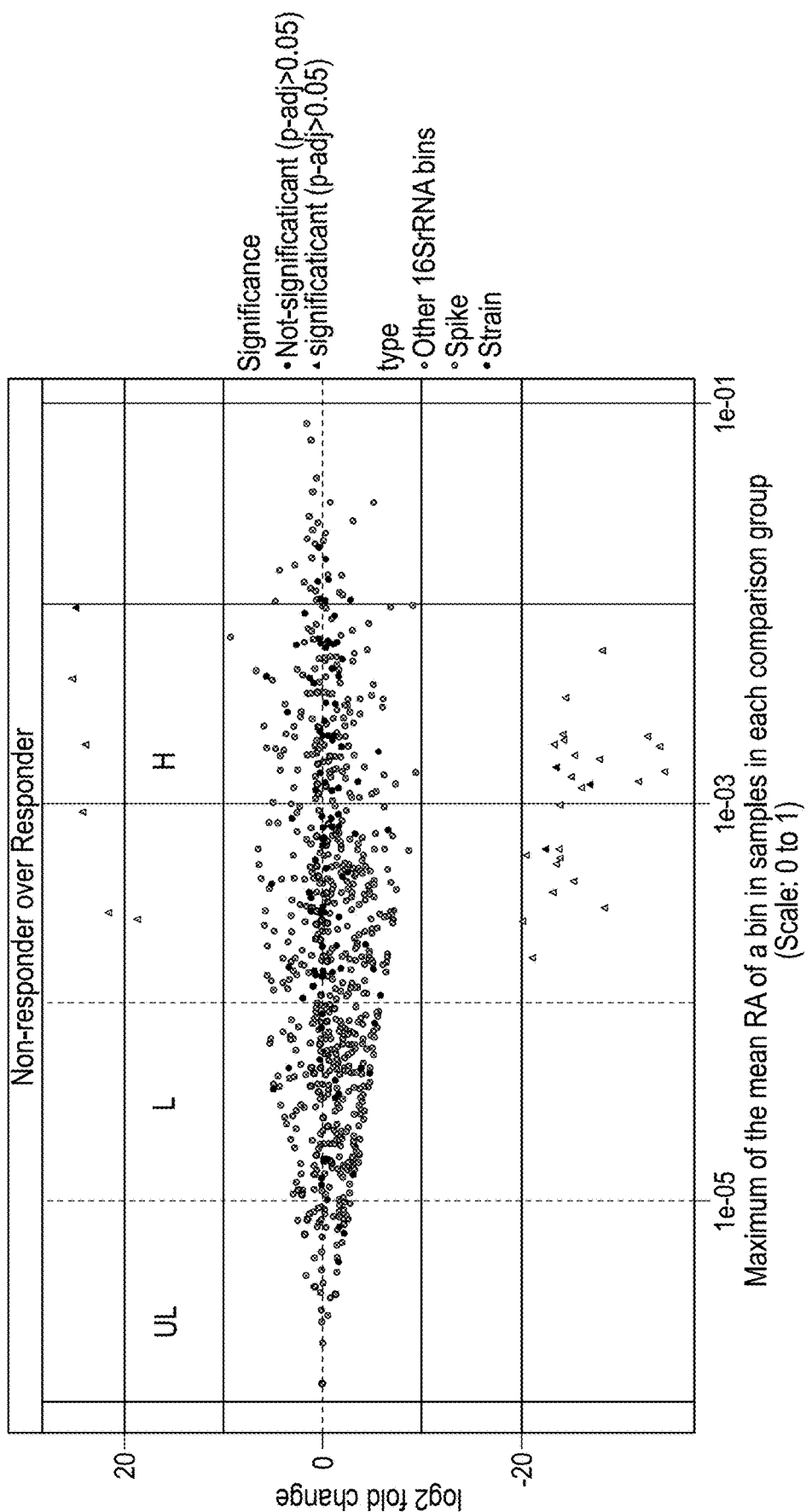
FIG. 27 is an example result from applying PPV and miss rate from the spike mix analysis to identify confidence associated with significant microbiome shifts identified in the non-responder over responder contrast in melanoma subjects on check-point inhibitor therapy.

The spike mix analysis can be applied to determine confidence associated with strains identified as significant (illustrated as black-triangular points on FIG. 27) in the comparison of stool samples from responders and non-responders to check-point inhibitor therapy. By comparing the relative abundance of strains identified as significantly enriched or depleted in non-responder to the relative abundance of spikes, it can be determined that all detected strain shifts are high confidence (all strain shifts were high abundance shifts & PPV for shifts for high abundance spike was 1, indicating that PPV for strains that are high abundance is 1). Also based on the analysis of spikes, there was low sensitivity to shifts in ultra-low abundant strains i.e. there is a high likelihood that there is missing shifts in some ultra-low abundant strains. Thus spike mix as applied to the analysis of microbiome from human stool samples, enables us to determine the accuracy associated with shifts in strains.

As used in this specification, the singular forms "a," "an," and "the" include plural referents unless the context clearly dictates otherwise. Thus, for example, the term "a member" is intended to mean a single member or a combination of members, "a material" is intended to mean one or more materials, or a combination thereof.

As used herein, the term "microbiome" refers to the totality of microbes (e.g. bacteria, archaea, fungi), their genetic elements (genomes) in a defined environment. The microbiome may be of any origin, for example a gut microbiome, an oral microbiome, an intestinal microbiome, a bronchial microbiome, a skin microbiome or a vaginal microbiome. According to a particular embodiment, the microbiome is a gut microbiome. In order to analyze the microbiome, samples are taken from a subject.

As used herein, the term "differential abundance analysis" refers to analyzing and comparing the relative abundance of taxa in two or more samples or groups. Differential abundance analysis allows determination of which specific microbes are significantly differentially abundant between two groups through statistical testing. Significant changes in certain microbes' abundances can be linked to inflammatory bowel disease, diarrhea, obesity, HIV, diet, culture, age, and antibiotic use.

As used herein, the term "spike" refers to a number of microbial cells wherein the number of the cells is known and can be used to perform microbial profiling and make calculations based on the output of the know "spike" cells. The spike microbes are usually not normally found in a given environment. These microbes are mixed into samples at known quantities which can allow quantification of the sample's total microbial load and calculation of the relative abundance in the sequencing output.

As used herein, the term "sample" refers to a composition that contains an analyte or analytes to be analyzed or detected or used otherwise. A sample can be heterogeneous, containing a variety of components (e.g., DNA, RNA, different proteins) or homogenous, containing one component. In some instances, a sample can be naturally occurring, a biological material, and/or a man-made material (e.g. a synthetic control polynucleotide). Furthermore, a sample can be in a native or denatured form. In some instances, a sample can be a single cell (or contents of a single cell) or multiple cells (or contents of multiple cells), a blood sample, a tissue sample, a skin sample, a urine sample, a stool sample, a water sample, and/or a soil sample. In some instances, a sample can be from a living organism, such as a eukaryote, prokaryote, mammal, human, yeast, and/or bacterium or the sample can be from a virus. In some instances, a sample can be one or more stem cells (e.g., any cell that has the ability to divide for indefinite periods of time and to give rise to specialized cells).

The user devices, remote devices, central authority devices or DAA system devices disclosed herein can be any suitable electronic devices. For example, in some embodiments, the electronic device can be a personal computer (PC), a personal digital assistant (PDA), a smart phone, a laptop, a tablet PC, a server device, a workstation, and/or the like. The electronic device can include at least a memory, a processor, a network interface, and an output device. For example, in some embodiments, the output device can be any suitable display that can provide at least a portion of a user interface for a software application (e.g., a mobile application, a PC application, an internet web browser, etc.) installed on the electronic device. In such embodiments, the display can be, for example, a cathode ray tube (CRT) monitor, a liquid crystal display (LCD) monitor, a light emitting diode (LED) monitor, and/or the like. In other embodiments, the output device can be an audio device, a haptic device, and/or any other suitable output device. The network interface can be, for example, a network interface card and/or the like that can include at least an Ethernet port and/or a wireless radio (e.g., a WiFi® radio, a Bluetooth® radio, etc.). The memory can be, for example, a random access memory (RAM), a memory buffer, a hard drive, a read-only memory (ROM), an erasable programmable read-only memory (EPROM), and/or the like. The processor can be any suitable processing device configured to run or execute a set of instructions or code. For example, the processor can be a general purpose processor, a central processing unit (CPU), an accelerated processing unit (APU), and Application Specific Integrated Circuit (ASIC), and/or the like. The processor can be configured to run or execute a set of instructions or code stored in the memory associated with using, for example, a PC application, a mobile application, an internet web browser, a cellular and/or wireless communication (via a network), and/or the like, as described in further detail herein.

Various terms are used herein and in the appended claims to describe, for example, various parts, portions, layers, etc. of an interaction between a user of an electronic device and a user of a different electronic device. For example, the terms "communication" and "message" and "information" can be used interchangeably and refer generally to data being sent, in substantially one direction, from a user of an electronic device to a user of another electronic device. By way of example, a communication or message from a user of a first electronic device to a user of a second electronic device can be an email, a voice message, an instant message (IM), an SMS, and/or the like, as described herein. A response to the email from the user of the second electronic device to the user of the first electronic device can similarly be referred to as a communication or message or information.

As used herein, the terms "modality," "communication mode," and "channel" can be used interchangeably and refer generally to one or more modes of communication using, for example, one or more electronic devices. Such modes of communication can be associated with a specific format (e.g., a data unit format) that, in some instances, can be unique to that mode of communication (e.g., a different protocol, a different data unit structure or arrangement, etc.). For example, a cellular telephone (e.g., a smart phone) can send a communication to another cellular telephone using a short message service (SMS) modality. Thus, when referring to a modality or channel it should be understood that the modality or channel includes, defines, and/or otherwise is associated with a data unit format suitable for transmission of data via that communication mode.

As used herein the term "data processing unit" or "processor" or "Input/Output unit" or a "Communicator" can refer to, for example, any computer, electronic switch, switch fabric, portion of a switch fabric, router, host device, data storage device, line card, backplane or the like used to process, transmit and/or convey electrical and/or optical signals. An I/O unit or a communicator can include, for example, a component included within an electronic communications network. In some embodiments, for example, a data processing unit can be a component included within or forming a portion of a core switch fabric of a data center. In other embodiments, a processor or I/O unit can be an access switch located at an edge of a data center, or a host or peripheral device (e.g., a server) coupled to the access device. For example, an access switch can be located on top of a chassis containing several host devices.

As described herein, the term "nucleic acid," refers to a molecule comprising one or more nucleic acid subunits. In some embodiments, a "nucleic acid molecule" refers to the phosphate ester polymeric form of ribonucleosides (adenosine, guanosine, uridine or cytidine: "RNA molecules") or deoxyribonucleosides (deoxyadenosine, deoxyguanosine, deoxythymidine, or deoxycytidine: "DNA molecules"), or any phosphoester analogs thereof. Such as phosphorothioates and thioesters, in either single stranded form, or a double-stranded helix. In other words, a nucleic acid may be single-stranded and/or double-stranded. Nucleic acids comprise "nucleotides", which, as used herein, can include those moieties that contain purine and pyrimidine bases, and modified versions of the same. Such modifications can, for example, include methylated purines or pyrimidines, acylated purines or pyrimidines, alkylated riboses or other heterocycles. In addition, the term "nucleotide" or "polynucleotide" includes those moieties that contain hapten or fluorescent labels and may contain not only conventional ribose and deoxyribose sugars, but other sugars as well.

A "polynucleotide' or "nucleotide sequence' is a series of nucleotide bases (also called "nucleotides' in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids' (PNA) formed by conjugating bases to an amino acid backbone. This also includes nucleic acids containing modified bases, for example thio-uracil, thioguanine and fluoro-uracil.

Modified nucleosides, nucleotides or polynucleotides can also include modifications on the sugar moiety, e.g., wherein one or more of the hydroxyl groups are replaced with halogen atoms or aliphatic groups, or are functionalized as ethers, amines, or the like. Double stranded DNA-DNA, DNA-RNA and RNA-RNA helices are possible. The term nucleic acid (NA) molecule, and in particular DNA or RNA molecule, refers only to the primary and secondary structure of the molecule, and does not limit it to any particular tertiary forms. Thus, this term includes double-stranded DNA found, interalia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule' is a DNA molecule that has undergone a molecular biological manipulation.

The terms "polynucleotide", "nucleotide", "nucleotide sequence", "nucleic acid", "NA sequence", "sequence" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, intrans, messenger RNA (mRNA), transfer RNA, ribosomal RNA, short interfering RNA (siRNA), short-hairpin RNA (shRNA), microRNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones. As disclosed above, a polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used in this specification, a "sequence" refers to any suitable portion of data related to sequence information regarding a nucleic acid molecule. For example, sequence can refer to a DNA or RNA sequence, such as, information about the sequence of nucleotide bases or sequence of base pairs, and/or the like. In some instances, the verb form "sequence" or "sequencing" used in this specification refers to the act of obtaining the sequence information of a nucleic acid molecule.

A network can be, for example, a local area network (LAN), a wide area network (WAN), a metropolitan area network (MAN), a worldwide interoperability for microwave access network (WiMAX), a telephone network (such as the Public Switched Telephone Network (PSTN) and/or a Public Land Mobile Network (PLMN)), an intranet, the Internet, an optical fiber (or fiber optic)-based network, a virtual network, a cellular network, and/or any other suitable network. Moreover, the network can be implemented as a wired and/or wireless network. In some embodiments, the network can include one or more networks of any type such as, for example, a LAN and the Internet.

A communication device or communicator can be any suitable device that can communicate with the network (e.g., any or the data processing units described above, and/or any combination or part thereof). Moreover, the communication device can include one or more wired and/or wireless interfaces, such as, for example, Ethernet interfaces, optical carrier (OC) interfaces, and/or asynchronous transfer mode (ATM) interfaces. In some embodiments, the communication device can be, for example, a network interface card and/or the like that can include at least an Ethernet port and/or a wireless radio (e.g., a WiFi® radio, a Bluetooth® radio, etc.).

A memory can be, for example, a random access memory (RAM), a memory buffer, a hard drive, a read-only memory (ROM), an erasable programmable read-only memory (EPROM), and/or the like. In some embodiments, the memory can be configured to store, for example, one or more modules that can include instructions that can cause a processor to perform one or more processes, functions, and/or the like.

A processor can be any suitable processing device configured to run or execute a set of instructions or code such as, for example, a general purpose processor (GPU), a central processing unit (CPU), an accelerated processing unit (APU), an application specific integrated circuit (ASIC), a network processor, a front end processor, a field programmable gate array (FPGA), and/or the like. As such, a memory can store instructions to cause the processor to execute modules, processes, and/or functions associated with DAA system, for example.

A database can be, for example, a table, a repository, a relational database, an object-oriented database, an object-relational database, a structured query language (SQL) database, an extensible markup language (XML) database, and/or the like. In some embodiments, the database can be configured to store data such as, for example, unique user identifiers within a DAA system, user information indexed by user identifiers, sequence information, cryptographic function information, cryptographic mapped values, and the like.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™ Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

While various embodiments have been described and illustrated herein, it is to be understood that a variety of other tools, means, and/or structures for performing the functions and/or obtaining the results and/or one or more of the advantages described herein, and each of such variations and/or modifications, is within the scope of the disclosure and example embodiments described herein. More generally, it is to be understood that all parameters, dimensions, materials, and configurations described herein are provided as illustrative examples, and that the actual parameters, dimensions, materials, and/or configurations can depend upon the specific application or applications for which the disclosed teachings is/are used/implemented. Many equivalents to the specific example embodiments described herein are readily recognizable and/or can be ascertained using no more than routine experimentation. It is, therefore, to be understood that the foregoing embodiments are presented by way of example only and that, within the scope of the disclosure and equivalents thereto, and further embodiments within the scope of the disclosure can be practiced otherwise than as specifically described and/or claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The above-described embodiments can be implemented in any of numerous ways. For example, the embodiments or portions thereof can be implemented using hardware, software, and/or a combination thereof. When implemented in software, the software code can be executed on any suitable processor or collection of processors, whether provided in a single computer or distributed among multiple computers/servers/compute devices. Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various disclosed concepts can be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the disclosure as discussed above.

The terms "program" or "software" are used herein can refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present.

Processor-executable instructions can be in many forms, such as program modules, executed by one or more compute devices, and can include routines, programs, objects, components, data structures, etc. that perform particular tasks or implement particular data types, and the functionality can be combined and/or distributed as appropriate for various embodiments.

Data structures can be stored in processor-readable media in a number of suitable forms. For simplicity of illustration, data structures may be shown to have fields that are related through location in the data structure. Such relationships can likewise be achieved by assigning storage for the fields with locations in a processor-readable medium that conveys relationship between the fields. However, any suitable mechanism/tool can be used to establish a relationship between information in fields of a data structure, including through the use of pointers, tags, and/or other mechanisms/tools that establish relationship between data elements.

Various disclosed concepts can be embodied as one or more methods, of which examples have been provided. The acts performed as part of a particular method can be ordered in any suitable way. Accordingly, embodiments can be constructed in which acts are performed in an order different than illustrated/discussed, which can include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms. The use of flow diagrams and/or "step" language/terminology is not meant to be limiting with respect to the order of operations performed. The herein described subject matter sometimes illustrates different components contained within, or connected with, different other components. It is to be understood that such depicted architectures are exemplary and not limiting, and that many other architectures can be implemented which achieve the same or similar functionality and are within the scope of the disclosure. In a conceptual sense, any arrangement of components to achieve the disclosed functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components. The indefinite articles "a" and "an," as used herein in the specification and in claims, unless clearly indicated to the contrary, should be understood to mean "at least one."

The phrase "and/or," as used herein, is to be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein, "or" is to be understood to have the same meaning as "and/or" as defined above, unless context clear indicates otherwise. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein, the phrase "at least one," in reference to a list of one or more elements, is to be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc. It is to be understood that all transitional phrases, such as "comprising," "including," "carrying," "having," "containing," "involving," "holding," "composed of," and the like are open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Although various embodiments and/or instances have been described as having particular features, concepts, and/ or combinations of components, other embodiments and/or instances are possible having any combination or subcombination of any features, concepts, and/or components from any of the embodiments/instances described herein. For example, in some instances the systems and methods can be used to generate the template spikes and/or the spike in mixes. In some instances, the templates for the spikes can be generated and the template spikes themselves can be manufactured using commercially available sources that generated synthetic polynucleotides. In some instances, the systems and methods described can be used to evaluate a list of work flow pipelines to select one or more pipelines based on one or more chosen criteria. In some other instances, the systems and methods can be used to serve as an internal control for validation of results of a study including differential abundance analysis. In some instances, the same system can be used to generate spike-in mixes, use the spike-in mixes to choose a pipeline and to validate results using that pipeline. In some other instances, the systems and methods can be used only to validate results.

While various embodiments have been described above, it should be understood that they have been presented by way of example only, and not limitation. Where methods and steps described above indicate certain events occurring in certain order, the ordering of certain steps may be modified. Additionally, certain of the steps may be performed concurrently in a parallel process when possible, as well as performed sequentially as described above. Although various embodiments have been described as having particular features and/or combinations of components, other embodiments are possible having any combination or sub-combination of any features and/or components from any of the embodiments described herein. Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

EXAMPLES

Example 1: Validating Amplicon Sequence Processing Pipelines with Artificial Internal Standards Microbiome profiling techniques typically yield differential abundance results of certain organisms (or sequences) between cohorts, oftentimes the effect of a given variable or measured parameter. However, the vast majority of statistically significant results generated from these efforts are garnered from low abundance populations, which raises doubt as to the reproducibility and accuracy of these findings. A well-defined suite of NIST-standard nucleic acids was designed, produced in high quantity, and validated via both wet- and dry-lab protocols. This collection of nucleic acid standards was then applied as quantitative microbiome sequencing tracers (QMTs) to appraise the integrity of, and identify weaknesses within, existing 16S rRNA gene sequence analysis workflows.

Collection-to-results workflows were evaluated by spiking samples with known quantities of QMTs. Sample handling, 16S rRNA gene sequence processing (i.e., UPARSE, dada2), and biostatistical analyses (i.e., DESeq2, metagenomeSeq, edgeR, and t.test) were evaluated as parallel, independent workflows. Forty distinct workflows were evaluated for accuracy, sensitivity, specificity, and other related metrics, and were ranked accordingly. The highest ranked workflow consisted of sequence processing with dada2 (for error correction and trimming), taxonomic annotation of amplicon sequence variants (ASVs) in accordance with Greengenes and StrainSelect databases, and differential abundance analysis via the DESeq2 poscounts' method. This combination of techniques was deemed most appropriate for most target questions and applications.

The inclusion of well-defined internal standards is key to validating complex microbiome analyses and statistical methods. While routine in microarray expression studies, complex internal standards are not typically applied in next-generation sequencing-based assays. The design, development, and implementation of three distinct QMT cocktails, each comprising 69 unique 16S rRNA gene sequences are described herein. These QMT cocktails were used to assess the limitations of 40 distinct sequence processing/differential abundance testing workflows. Based on this work alone, and for the first time ever, confidence levels can be appended to the results of differential abundance analyses for each microbiome assay. Furthermore, biases resulting from sample handling, sequencing depth, or other processing considerations can now be readily identified in each sequencing run.

Figure 28:
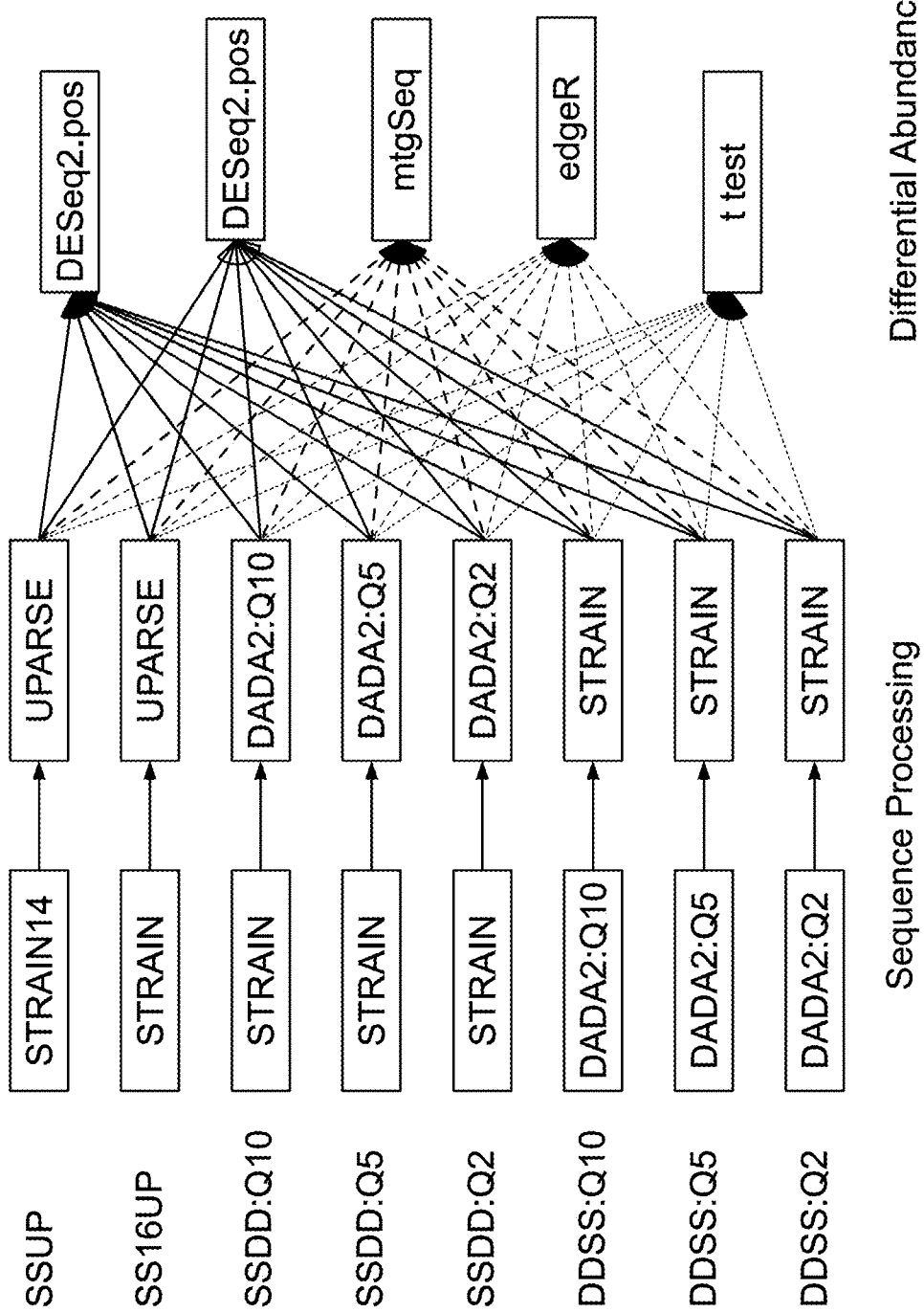
FIG. 28 is a schematic illustration of several example workflow pipelines that can be used for differential abundance analyses, which can be evaluated and validated using a DAA system according to an embodiment.

QMT cocktail was PCR amplified amidst human microbiome stool DNA. Thirty distinct sequencing libraries were generated from ten replicates of each of the three QMT cocktails (designated A, B, and C). A single MiSeq sequencing run generated a total of 12,663,065 reads from the 30 libraries. Raw sequences were processed and analyzed by each of seven distinct pipelines. By including internal QMTS of varying composition, the effectiveness of several processing and analysis techniques in the cradle-to-grave workflow was successfully evaluated (FIG. 28). The StrainSelect-to-UPARSE pipeline (SSUP) yielded the greatest number of usable reads for differential abundance analyses (n=9,424,347; 74%). The dada2-to-StrainSelect pipeline with truncation quality (truncQ) value of 2 (DDSS:Q2, n=8,960,565; 70%) had the next highest level of usable reads. The DDSS:Q10 sequence processing pipeline returned the fewest usable reads for differential abundance analyses (n=4,728,751; 37.8%), slightly more than half of the reads retained by DDSS:Q2. Not surprisingly, sequence retention increased as the stringency of the truncation quality (truncQ) parameter was reduced in the DADA2-first (DDSS) workflows. This was not the case for StrainSelect annotation-first (SSDD) pipelines. Sequence fidelity, i.e., the combined measure of error resulting from PCR and sequencing strategies, also varied between pipelines. Base calling error rates from DDSS pipelines were similar (DDSS:Q2 and DDSS:Q5=0.00052; DDSS:Q10=0.00057), while SSDD pipelines exhibited slightly greater error rates (up to 0.0012, SSDD:Qx). It must be noted that error rates for the SSDD pipelines were identical across Q-values since QMT and strain-level sequence read assignments occurred simultaneously.

Figure 29:
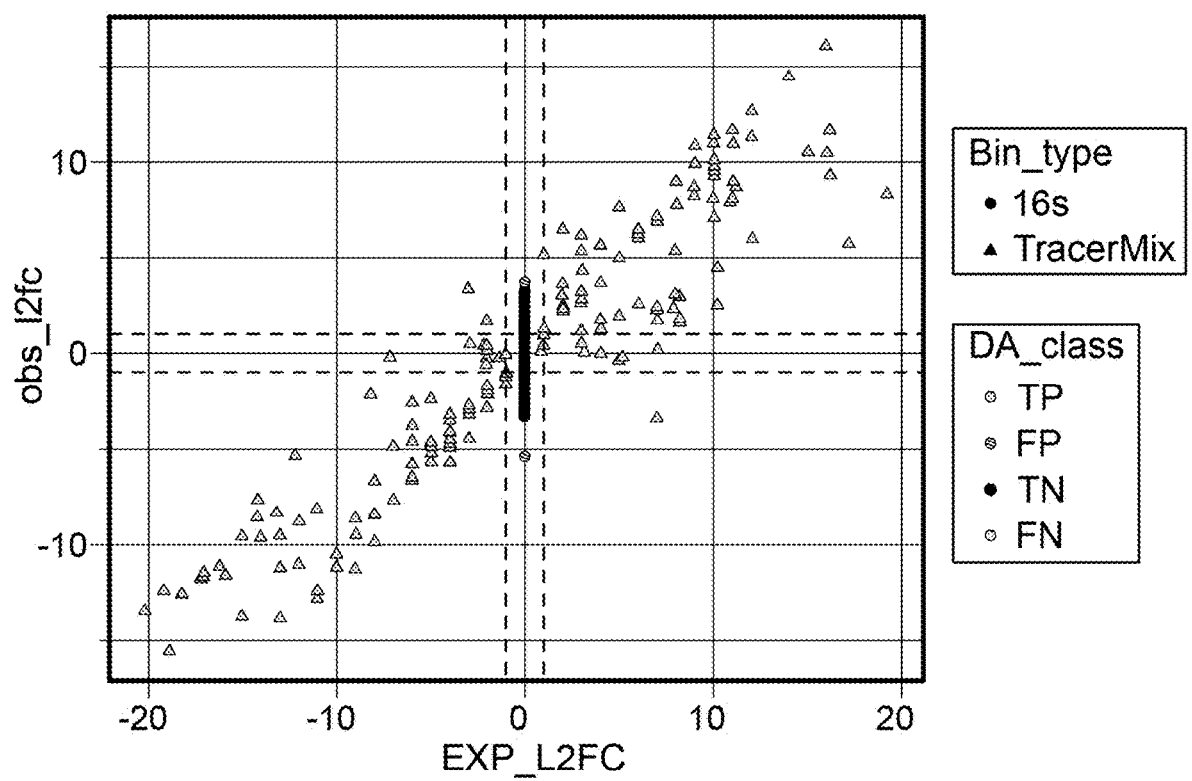
FIG. 29 is a schematic representation of classification of observed differential abundance shifts (observed log 2 fold change, obs_12fc), as compared to expected differential abundance (expected log 2 fold change, Exp_12fc) between mixes for one workflow (DDSS:Q2+DESeq2.poscounts).
Figure 30:
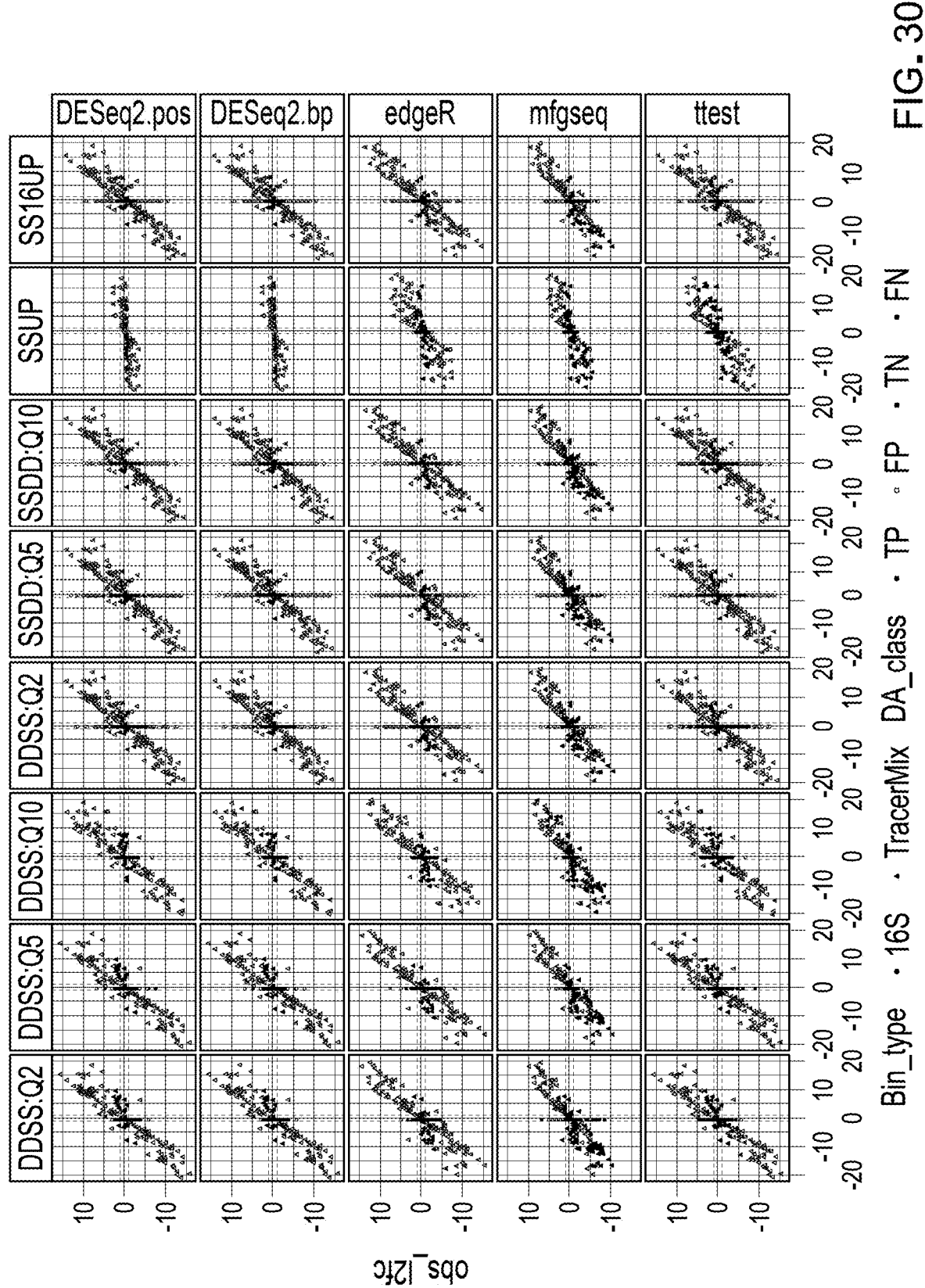
FIG. 30 is a schematic representation of classification of observed differential abundance shifts, as compared to expected differential abundance between mixes for all forty workflows.

Differential abundance results for each distinct QMT in each workflow were categorized into a confusion matrix as true positives, true negatives, false positives, or false negatives, relative to shifts in composition expected from the particular QMT tested (FIG. 29 and FIG. 30). A differential abundance test yielding an adjusted p-value <0.05 AND an absolute effect size (log-2 fold change) greater than 0 was deemed to have exhibited a 'true positive' shift. Since the same stool DNA extract was used for all libraries, none of the observed ASVs, OTUs, or non-dynamic QMTs were expected to yield statistically significant shifts in composition. All QMT, ASV, and OTU differential abundance results yielding an adjusted p-value <0.05 were deemed to have exhibited a 'false positive' shift. Conversely, any results that exhibited an adjusted p-value >0.05 or an effect size of 0 were deemed to have exhibited a 'true-negative' shift. If a dynamic QMT exhibited either no statistically significant test results (adjusted p-value >0.05) or had a null effect size (log-2 fold change equal to 0), it was deemed to have exhibited a 'false negative' shift.

A total of 140 true positive shifts (QMT only), 7 false positive shifts (one QMT and six ASVs), 1,071 true negative shifts (31 QMT and 1,041 ASVs), and 35 false negative shifts (QMT only) were observed for the DDSS:Q2+DESeq2.poscounts differential abundance analysis workflow (FIG. 29). In comparison, a total of 154 true positive shifts (QMT only), 41 false positive shifts (ASVs only), 1,431 true negative shifts (32 QMTs and 1,381 ASVs), and 21 false negative shifts (QMT only) were observed for the SSDD:Q2+DESeq2.poscounts analysis workflow (FIG. 30). The number of true positive QMT shifts varied widely across workflows (mean=122.8, min=37, max=155; 175 possible). There were few false positive QMT shifts (max=1) observed only in the DDSS workflows. The number of false positive shifts from a 16S rRNA sequence (at the ASV or OTU levels) varied considerably across the 40 workflows, ranging from 0-171 shifts (mean=46.3). These false positive shifts accounted for 0-5.8% (mean=0.17%) of all 16S shifts evaluated, per workflow.

Thirty-one to 32 of all 32 null QMT shifts (true negatives) were observed across all pipelines. Between 867 and 2582 true negative 16S shifts were encountered across workflows. This variation stems primarily from the method of binning 16S rRNA sequences into OTUs or ASVs, which resulted in an exceedingly large number of distinct bins. In using only one stool DNA extract common to all libraries, all null shift or statistically insignificant observations of 16S were expected to be negative. As such, there were no false negative 16S shifts. While true negative shifts accounted for 92.9-100% of all observed 16S shifts (mean, 97.3%) across workflows, false negative QMT shifts ranged from 20 to 138 (mean=52.2) per workflow.

Several metrics were considered in evaluating overall performance and comparing the accuracy of each workflow in correctly classifying each QMT or 16S shift. When coupled with DESEq2 or t.test to improve upon accuracy, the SSDD and SS16UP pipelines outperformed the DDSS pipelines with respect to sensitivity and precision. Coupling any sequence processing pipeline with metagenomeSeq to generate differential abundance statistics resulted in the lowest ranked accuracy, precision, and sensitivity values. A modified specificity metric (SPK16 Specificity) was created to summarize the presence of QMT and 16S true negatives concurrently in one metric. Inverse false positive rates and inverse false negative rates considered the frequency of false positives and false negatives, respectively, for QMTs and 16S rRNA sequences. The SSUP and DDSS sequence processing pipelines ranked highest with respect to specificity (SPK16 Specificity metric) and rate of false positives (lowest). These rates, however, varied little (<0.10) between all pipelines. Considerable variation was observed in inverse false negative rates, which ranged from 0.21(SSUP+mtgSeq) to 0.885 (SS16UP+DESeq2.pos, SSDD:Q5/Q10+DESeq2.pos, and SSDD:Q10+DESeq2.bp). Ultimately, no single pipeline was superior to all others with regard to resultant standard classification metrics.

Figure 31:
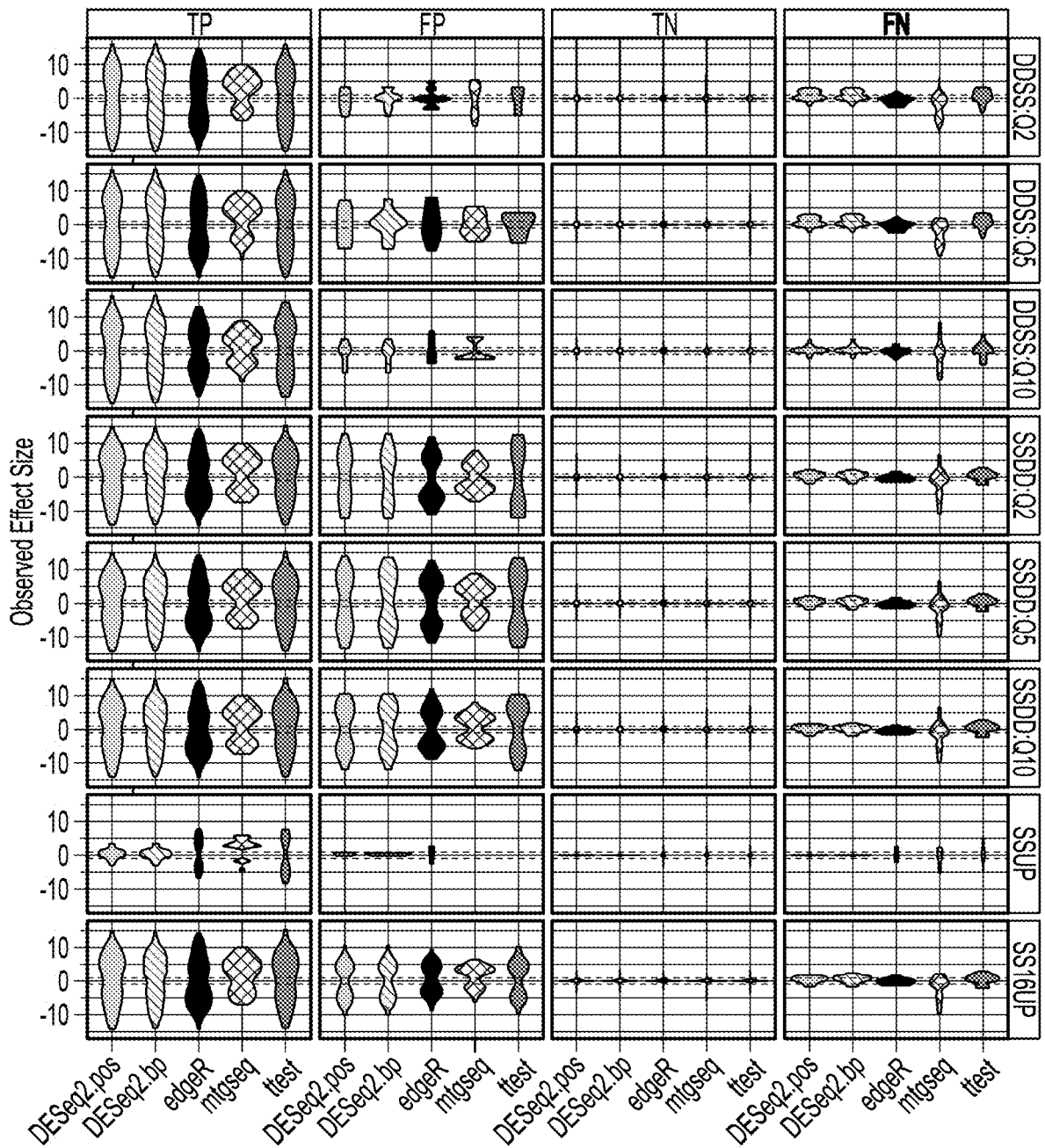
FIG. 31 is a schematic representation of violin plot of observed effect sizes (log 2 fold change in abundance) between any of the three tracer mixes (A vs B, B vs C, A vs C).

A modified positive predictive metric (SPK16_PPV) was created to assess each workflow's accuracy in classifying both QMT and 16S rRNA sequences. Performance pertaining to this modified PPV metric ultimately led to the endorsement and adoption of DDSS:Q2 in the microbiome analysis pipeline (FIG. 31). The DDSS pipeline coupled with any differential abundance analysis technique outperformed all but one of the SSDD pipelines. While SSUP performed impressively with respect to the SPK16_PPV metric, this pipeline suffered a markedly low QMT detection rate. In addition, DDSS pipeline performance improved as quality thresholds (truncQ) were reduced.

However, while performance was consistent across high and medium QMT abundance levels, predictive values plummeted for the QMTs at an 'ultra-low' abundance levels in all of the methods tested.

Figure 32A:
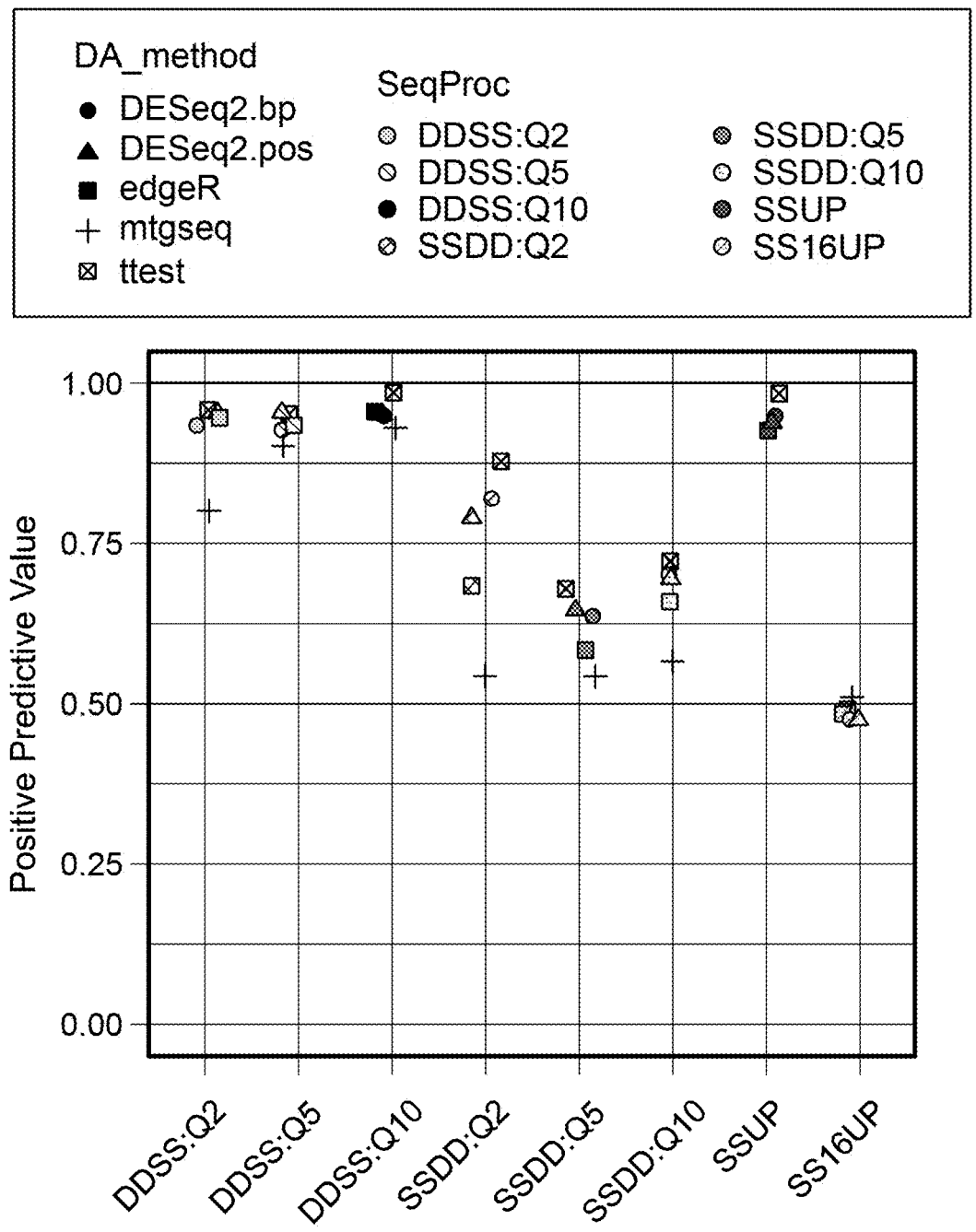
FIG. 32A is a plot of Positive Predictive Value for all differential abundance test methods and sequence processing workflows.
Figure 32B:
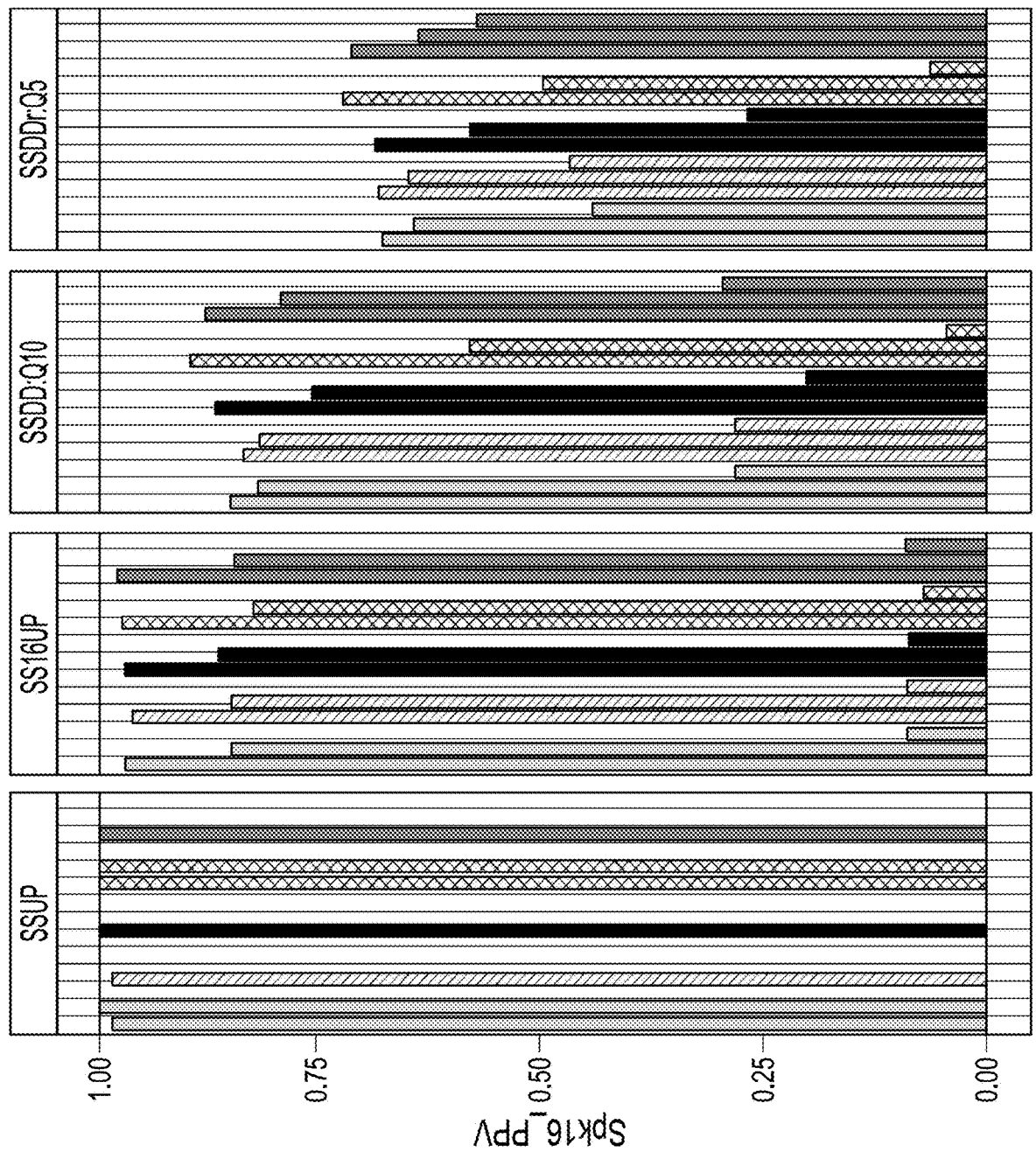
FIG. 32B is a plot of Positive Predictive Value, stratified by maximum observed relative abundance of ASV, OTU, or MCM.
Figure 32B:
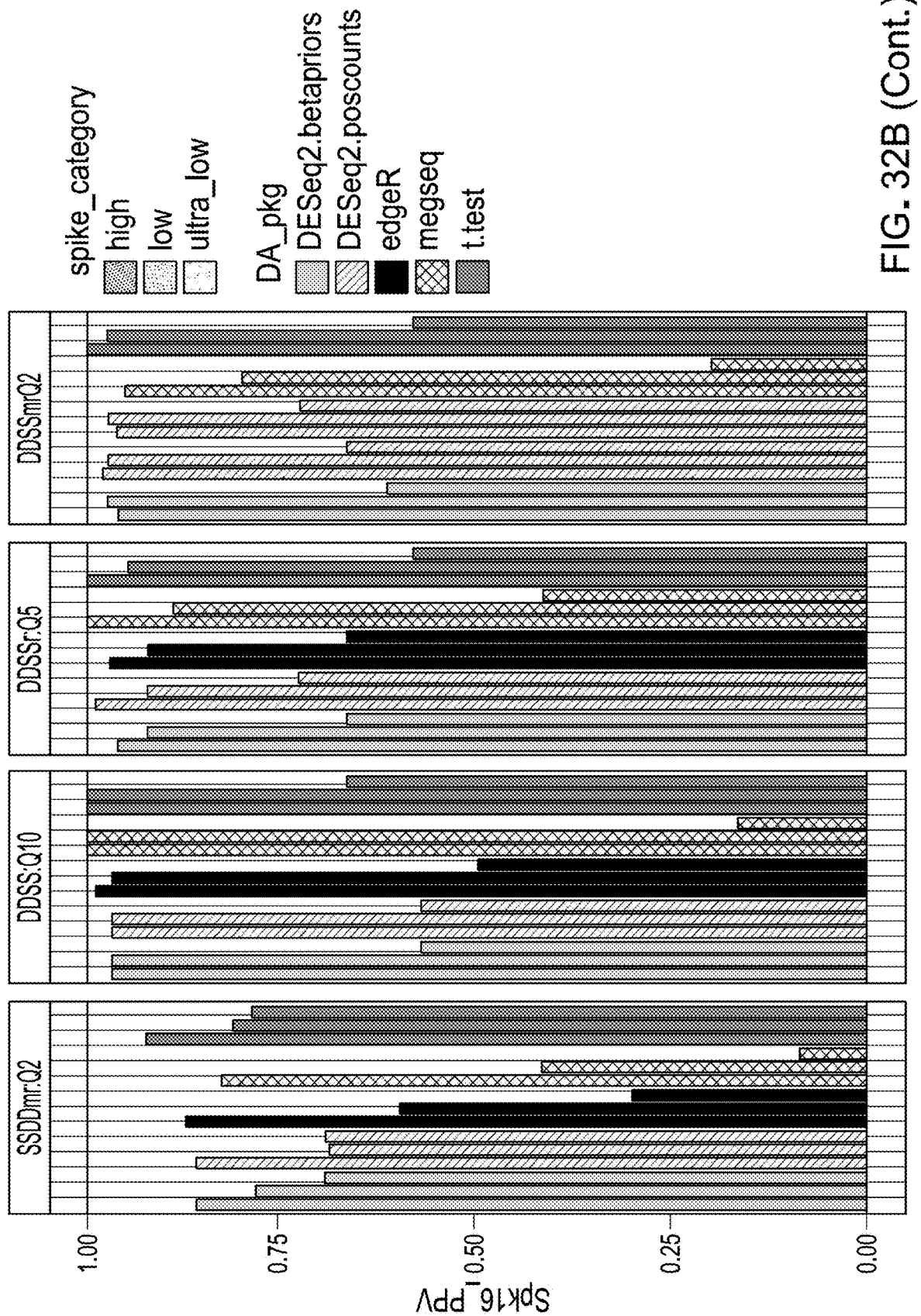

With regard to differential abundance analysis, accurately appraising the extent of change is as important as determining whether any change occurred. QMT results deemed as false negatives frequently exhibited smaller effect sizes (typically <three log-2 fold change in abundance) compared to those observed for QMT results deemed to be true positives via DESeq2.poscounts (>15; FIG. 32). As such, the application of a post-hoc effect size threshold based on each experiment's QMT shift results could significantly minimize false detection of spurious hits. False positives exhibited a smaller range of effect sizes in DDSS workflows than in SSDD or SS16UP workflows, highlighting the need for an effect size threshold to minimize the impact of false positives in downstream applications. To this end, sigma and theta were evaluated as means of quantifying the extent to which observed effect sizes matched the expected effect sizes.

Figure 33:
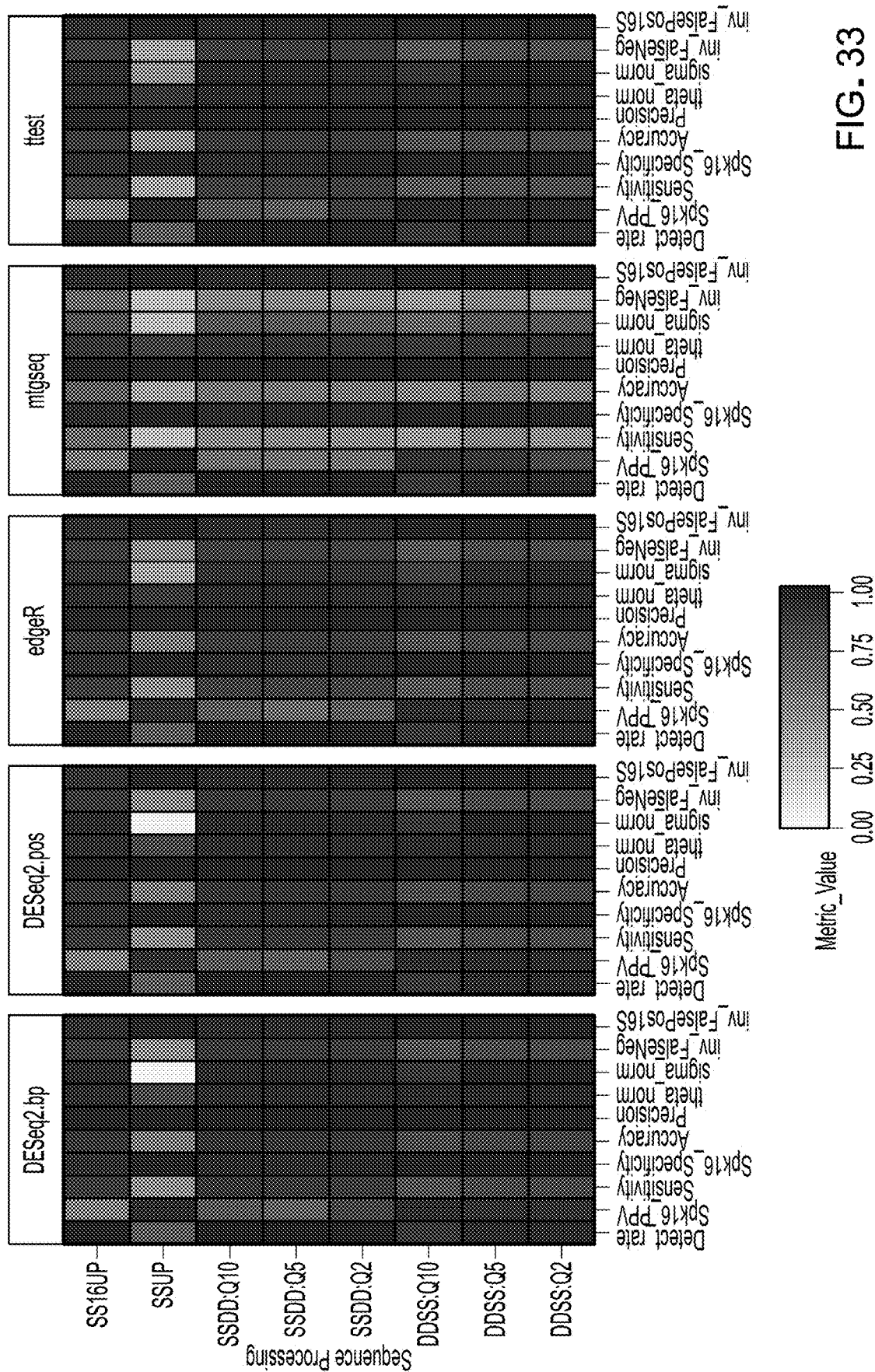
FIG. 33 is an additional schematic representation of results from evaluating pipelines for differential abundance analyses, quantified by multiple evaluation parameters, using a DAA system according to an embodiment.
Figure 34:
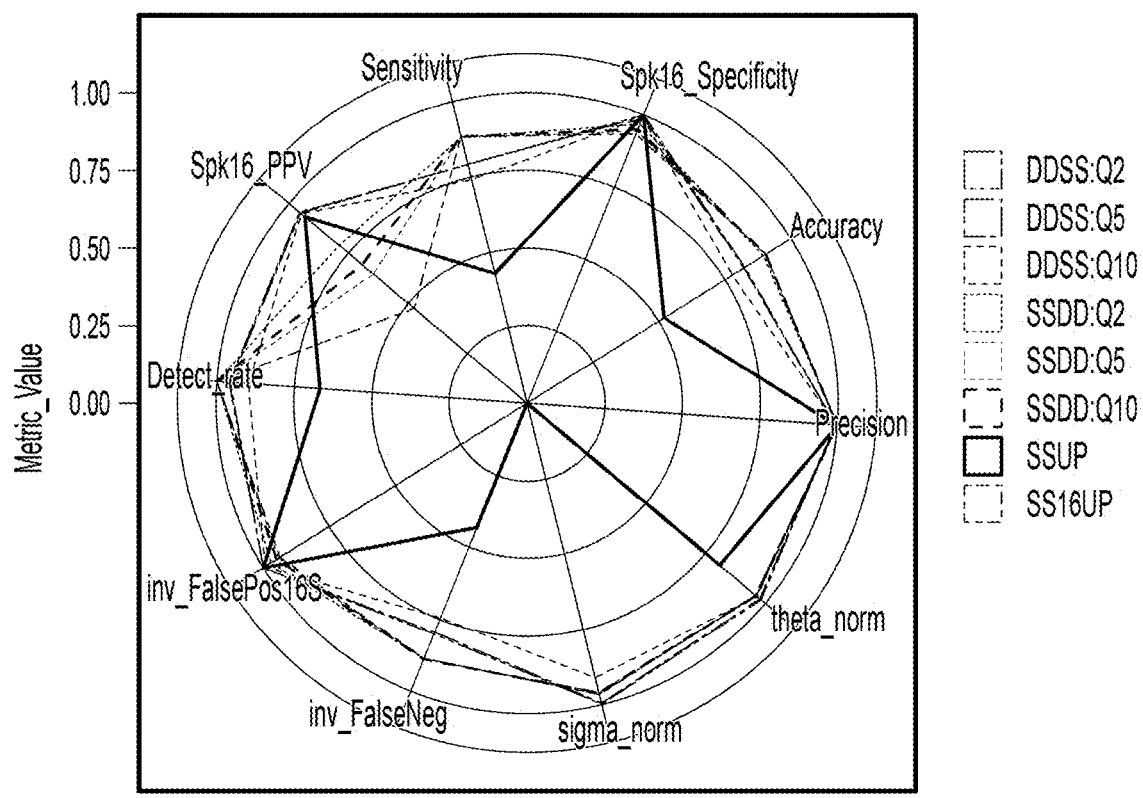
FIG. 34 is a radar plot for all metrics used in calculating overall pipeline score.
Figure 35A:
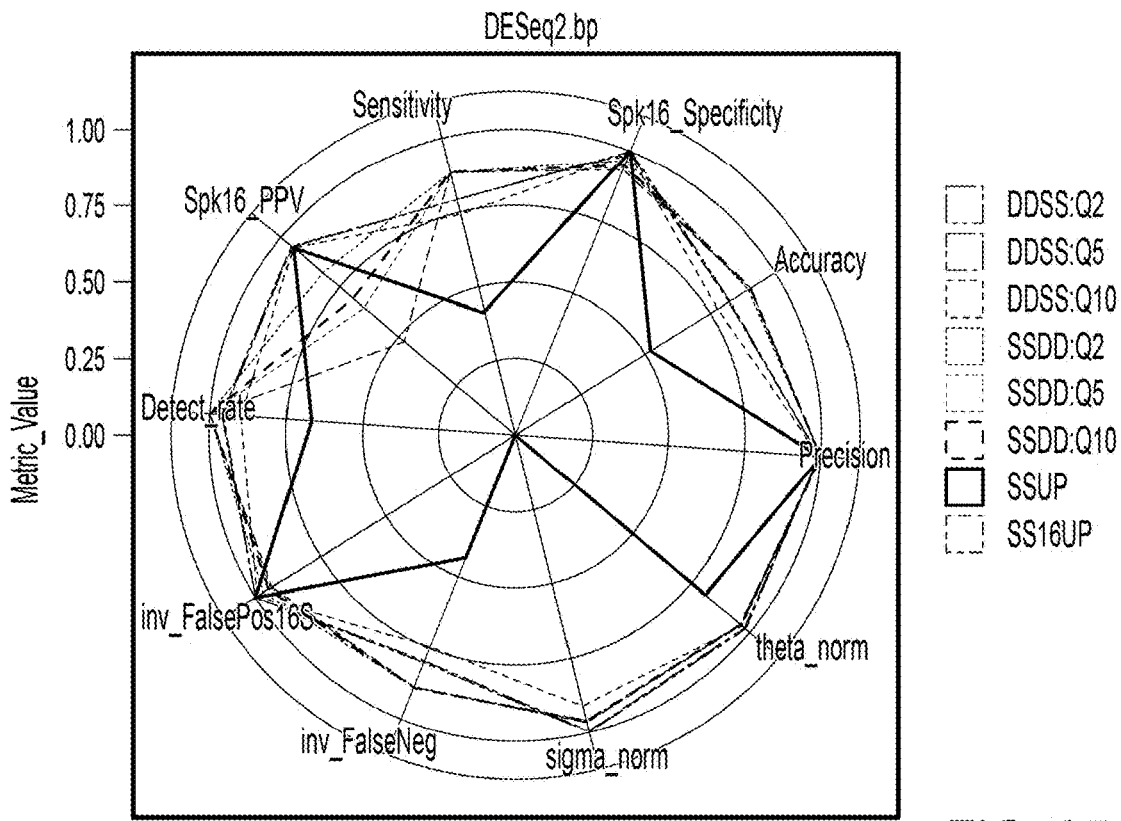
FIG. 35 is a scoring radar plot across all metrics for all sequence processing pipelines in the remaining four differential abundance methods: a) DESeq2.betapriors, b) metagenomeSeq, c) edgeR, and d) t test.
Figure 35B:
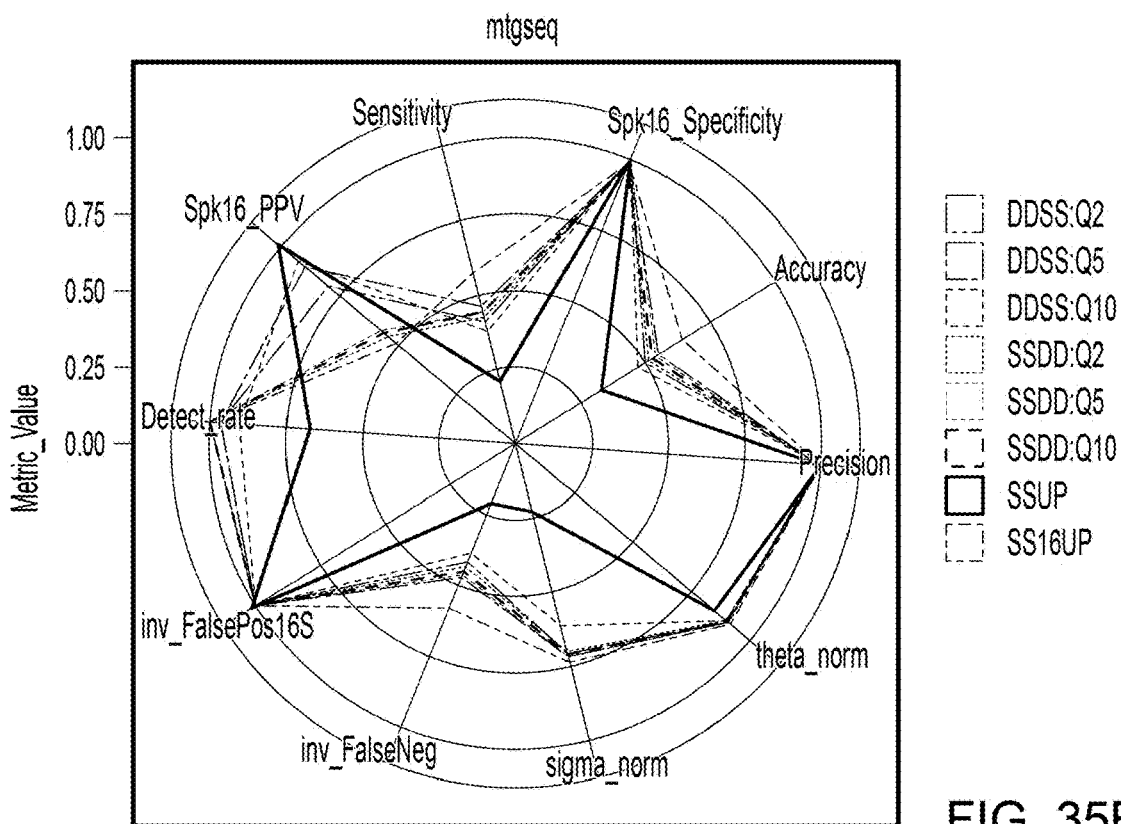
Figure 35C:
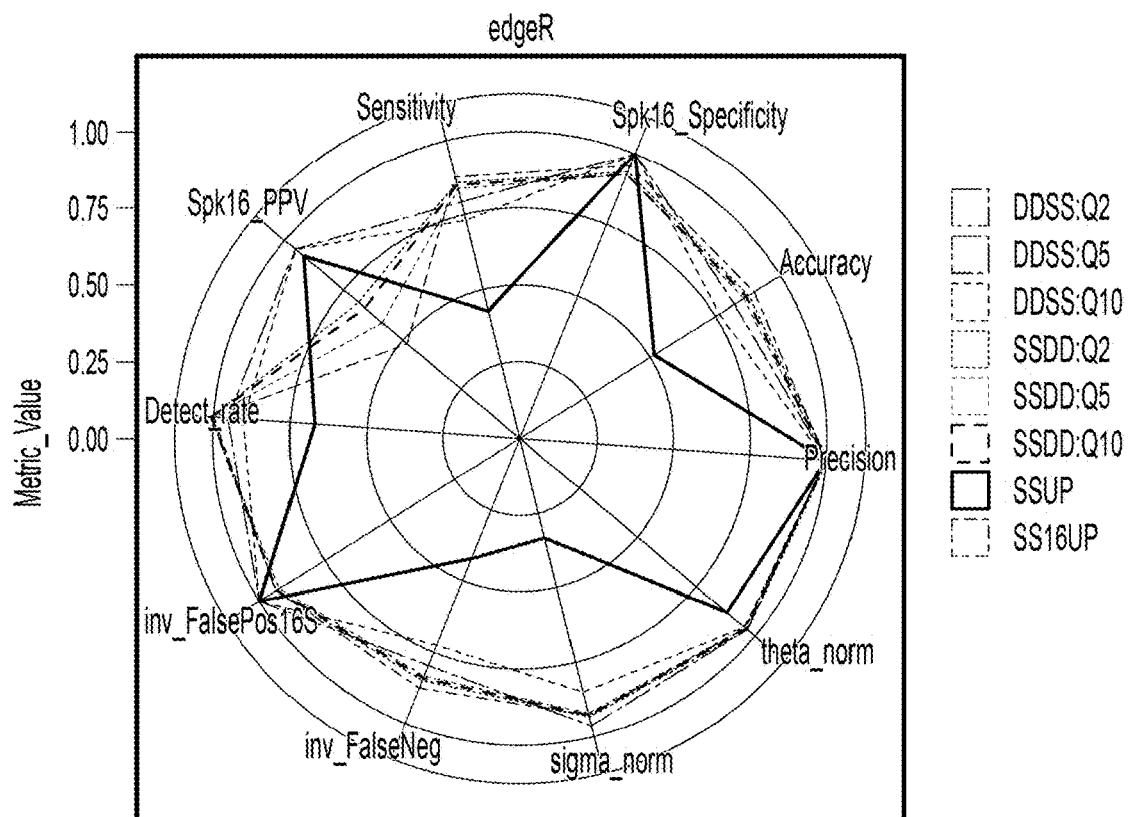
Figure 35D:
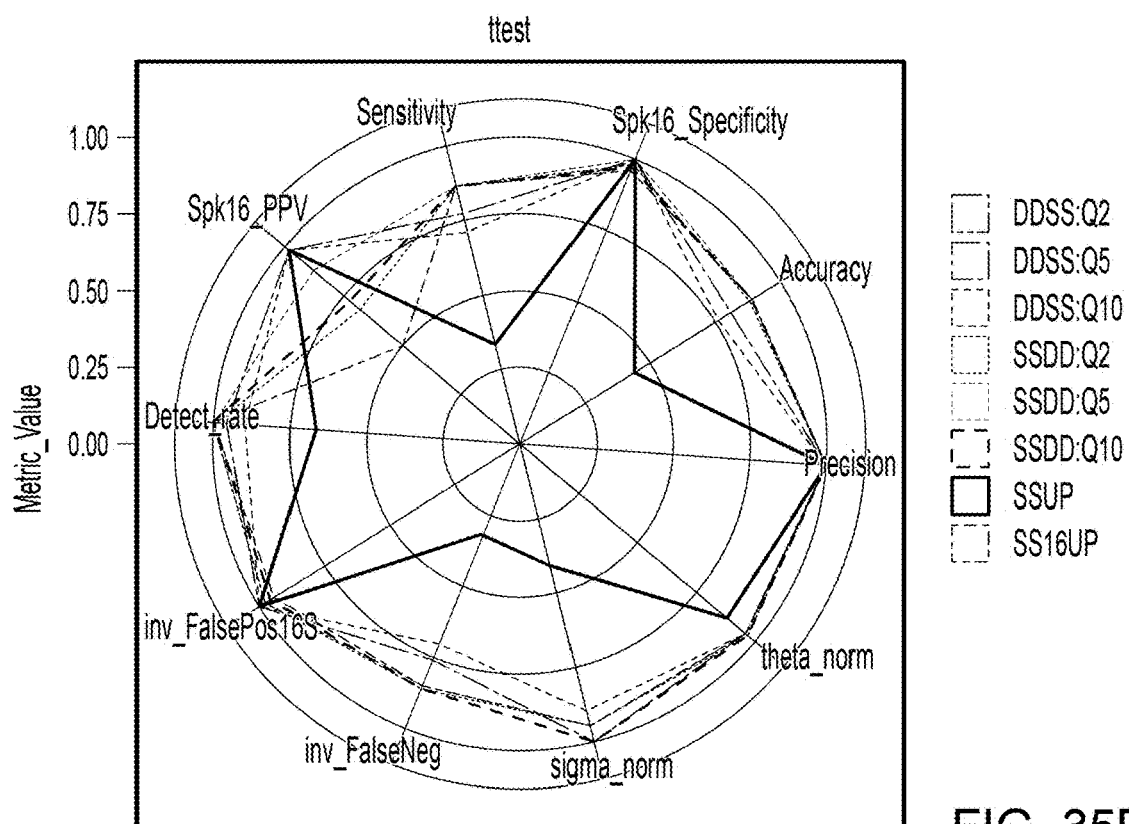

Sequence processing and analysis workflows were ranked according to cumulative scoring across multiple classification and performance testing results (FIGS. 33, 34 and 35). None of the pipelines tested yielded ideal results for each and every metric considered. However, subjecting sequence data to DADA2 denoising techniques prior to read-mapping annotation via taxonomic reference databases improved performance across all metrics assessed. The lowest DADA2 value tested (q=2) yielded the best all-around performance. Statistical normalization via DESeq2 proved superior to all other techniques tested (n=30, 10 per group).

Based on the systematic evaluation of workflows conducted above, the best overall performance was achieved in pipeline DDSS:Q2 with DESeqe2.poscounts. While this approach applies to the sequencing of the V4 hypervariable region of the 16S rRNA gene, it can be easily tailored for application on other amplicon targets. Appreciating the necessity of tried and true internal standard controls, an in-situ (same tube as sample) control mixture was synthesized with which to evaluate inherent biases in sample processing and analysis. Internal control standards are applied routinely in microarray based research to confirm successful hybridization and data collection. In addition to providing a more direct appraisal of bias, by virtue of application within the sample tube, the design comprises much greater sequence diversity (i.e., capable of yielding superior estimates of bias, confidence, etc.) than other available standards. These advances have led to the development of a more robust 16S rRNA gene amplicon sequencing pipeline, with which accuracy can be assessed within each and every sequencing run, and in turn, generate reliable differential abundance measurements of the microbiome.

Microbiome Control Mixtures.

Gene sequence templates were procured from NIST stock materials, prepared at various concentrations, systematically mixed together into predefined consortia, and used as microarray internal standard controls. As all of these sequences were of known, non-ribosomal origin, they did not conflict with, nor by any means exert a competitive effect on, other sequences being actively assayed. Each control template was a manufactured, artificial plasmid construct bearing an internal non-ribosomal DNA sequence sourced from NIST Standard Reference Materials (SRM 2374). PCR primers were designed to amplify a target region of specific length and GC content from each source plasmid. These plasmids where then subjected to PCR-amplification with corresponding primers, which themselves housed flanking regions that facilitated subsequent amplification using primers targeting the V4 hypervariable region of the 16S rRNA gene. Control templates spanned a wide range of GC content (~35-60% GC) to appropriately mimic known sequence variability. Following PCR amplification, products were gel-purified and quantified. Three unique microbiome control mixtures were then created from the resulting amplicon sequences, each of which comprised all 69 distinct sequence templates at concentrations spanning more than six orders of magnitude in its final concentration (0.1-120,000 copies per PCR reaction). A minimum of three unique sequence standards, each of which was verified via Sanger- (>4×) and deep Illumina-sequencing of the final pools, were included at each abundance level in all three cocktails.

Sample Preparation, Sequencing, and Sequence Processing.

A stool-sourced DNA extract spiked with one of the QMTs was subjected to PCR amplification using primers targeting the V4 hypervariable region of the 16S rRNA gene in replicate (n=10). As three distinct QMTs were tested, a total of 30 PCR libraries were purified, quantified, pooled in equimolar fashion, and sequenced in a single run on an Illumina MiSeq. Raw reads were then demultiplexed and processed via one of the seven sequence processing workflows detailed below. As such, one abundance table and one taxonomy table resulted for each workflow.

De novo sequence clustering using UPARSE. Resulting sequence reads were merged and oriented using USEARCH 10.0.240 (-fastq_mergepairs and -orient commands respectively using default settings). Reads were then quality-filtered based on maximum expected error (i.e., 1) prior to being dereplicated and sorted by size (discarding singletons) using the -derep_fulllength and -sortbysize utilities in USEARCH. De novo clustering of OTUs at a 97% identity threshold was then achieved with the -cluster_otus tool in USEARCH.

Generating ASV with DADA2. Raw sequence reads were processed with DADA2 applying default settings for filtering, learning errors, dereplication, ASV inference, and chimera removal. Truncation quality (truncQ) was set to 2, 5, or 10 depending on particular sequence processing workflow. Ten nucleotides were then trimmed from each terminus of each read, both forward and reverse.

Strain-level annotation. In the case of four of the seven sequence processing workflows employed (noted as SS14-xx or SS16-xx), reads were first mapped against an in-house strain database. In the case of the other three workflows, raw reads were first merged and oriented using USEARCH utilities (-fastq_mergepairs and -orient, respectively). Following this initial census, all reads were then mapped against StrainSelect, a strain-specific sequence database (version years 2014 and 2016, abbreviated SS14 and SS16 respectively) using USEARCH. StrainSelect is a repository of 16S rRNA gene sequences obtained from gene sequencing, genome sequencing, draft genomes, and metagenomic assemblies of known prokaryotic strains. Read pairs that matched to a unique strain were assigned accordingly and not considered in subsequent de novo clustering steps in the SS14-xx and SS16-xx workflows.

Differential Abundance Testing

Pre-processing. For all workflows, prevalence filtering was applied such that any OTU, ASV, strain, or QMT sequences present in at least 5% of samples (i.e., 2 or more) was considered in the analysis. For OTU, ASV, strains, or QMT sequences of which fewer than three positive samples were detected in each mixture comparison group, one read was added to the deepest sequenced samples per comparison group so that three samples overall yielded positive values (a requirement for metagenomeSeq).

Statistical testing. Five distinct statistical tests were applied to assess differential abundance across cohorts: DESeq2 (ver. 1.18.1) with positive counts utility applied to mitigate sparse data, DESeq2 with betapriors applied, edgeR (ver. 3.20.5), metagenomeSeq (ver. 1.20.1), and t-tests using the R stats package (ver. 3.4.1). For DESeq2.poscounts, estimateSizeFactors( ) was applied using type=poscounts before running the differential abundance testing with DESeq( ) Log 2 fold-change values were adjusted by applying lfcshrink( ) to the DESeq( ) results. For DESeq2.betapriors, DESeq( ) was used for differential abundance testing with betapriors=TRUE. Testing with edgeR was achieved in accordance with procedures outlined for differential abundance testing in McMurdie and Holmes 2014 (McMurdie, P. J., & Holmes, S. (2014). Waste Not, Want Not: Why Rarefying Microbiome Data Is Inadmissible. PLoS Computational Biology, 10(4), e1003531. doi.org/10.1371/journal.pcbi.1003531). For metagenomeSeq, css normalization was first applied with cumNorm( ), followed by differential abundance testing via fitFeatureModel( ). An unpaired t-test was performed and log 2 fold-change was calculated using the foldchange( ) and foldchange2logratio( ) utilities of the gtools package (ver. 3.5.0). P-values were then adjusted with p.adjust( ) using method="BH" as defined in the R stats package.

Effect Size Comparisons. The distribution of effect sizes observed within each analysis workflow for each QMT comparison were evaluated using a one way ANOVA test. First, differences in effect size distributions were assessed to evaluate the interaction of sequence processing and differential abundance methods within a confusion matrix class (e.g. for 'true positives only', the ANOVA formula was evaluated as 'observed effect size'~SeqProc*DA_method. Subsequently ANOVA tests were completed to test for 1) differences due to sequence processing methods (SeqProc) within a differential abundance test (DA_method) and 2) differences due to differential abundance test methods within a sequence processing method. For any ANOVA with a significant p-value <0.05, a post-hoc Tukey's test was calculated to identify which specific groups differed.

Pipeline Comparisons and Rankings

For all 40 distinct workflows, each QMT comparison (e.g., mix A vs. mix B, mix B vs. mix C) was deemed to be a true-positive, true-negative, false-positive, or false-negative based on the adjusted p-value and log 2 fold-change. A true positive resulted when a QMT comparison yielded an adjusted p-value <0.05 and absolute log 2 fold-change>0 when the QMT was expected to be differentially abundant. Since all libraries were sourced from the same stool biospecimen, no 16S rRNA gene amplicons were expected to be significantly different in abundance between groups. As such, we also determined the number of true-negative and false-positive comparisons involving 16S rRNA gene amplicons. These six values were used to calculate the metrics described below.

Individual Metric Calculations

Detection rate was calculated by dividing the number of QMT sequences detected in a workflow by the total number of QMT sequences (69 total).

Sensitivity was calculated by dividing the total number of true-positive QMT comparisons by the total number of expected differentially abundant QMT comparisons.

Spk16_Specificity was calculated by dividing the total sum of true-negative QMT and 16S rRNA comparisons by the total sum of QMT and 16S rRNA comparisons that were not expected to be differentially abundant.

False negative rate was calculated by dividing the total number of false-negative QMT comparisons by the total number of expected differentially abundant QMT comparisons.

Accuracy was calculated by dividing the sum of total true-positive and total true-negative comparisons by the sum of total QMT comparisons expected to be differentially abundant and not expected to be differentially abundant.

Precision was calculated by dividing the total number of true-positive comparisons by the sum of total true-positives and total false-negatives.

16S false positive rate was calculated as by dividing the total number of false positive 16S rRNA gene sequence comparisons by the total number of 16S rRNA gene sequence comparisons. The inverse 16S false positive rate was determined by subtracting the 16S false positive rate from 1.

Spk16_PPV (positive predictive value) was calculated as total true positives/(total true positives+total false positives+ total false positive 16S comparisons).

Theta and sigma were calculated from the linear regression of observed log 2FC and expected log 2FC. Theta was calculated using the slope of this regression as absolute(atan(((slope−expected slope)/(1+expected slope*slope))))*(180/π), in which the expected slope was 1 (observed log 2FC=expected log 2FC). Normalized theta was calculated as 1−(theta/180). Sigma was calculated as the square root of the sum of residual errors of each spike comparisons compared to a line with a slope of 1 (observed log 2FC=expected log 2FC). Sigma normalized was calculated in relation to sigma values for all 40 unique workflows, in which sigma normalized=1−(sigma−minimum sigma)/(maximum signal−minimum sigma).

The overall pipeline score was calculated as:

(theta_normalized)+(sigma_normalized)+Detection rate+Sensitivity+Spk16_Specificity+Accuracy+ Precision+Spk16_PPV*2−(False Positive 16S rate*2+False Negative rate).

Highest possible score was 8.

TABLE 1

| Primer Name | Primer Sequence (5' to 3') | SEQ ID NO. |
|---|---|---|
| F-00003 | GTGCCAGCMGCCGCGGTAACTTCTCATAACCGTCTCCGA | 5 |
| F-00017 | GTGCCAGCMGCCGCGGTAACTTATAGTGCTTGCTAGCAC | 6 |
| F-00033 | GTGCCAGCMGCCGCGGTAAAGATTATTGAAAAGCTGGT | 7 |
| F-00046 | GTGCCAGCMGCCGCGGTAACCAGTAATTCTACCACGCCT | 8 |

TABLE 1-continued

| Primer Name | Primer Sequence (5' to 3') | SEQ ID NO. |
|---|---|---|
| F-00069 | GTGCCAGCMGCCGCGGTAAATTGAACTCAAGGGACGGTG | 9 |
| F-00083 | GTGCCAGCMGCCGCGGTAAACTCTTTTAGCTGCAGGACA | 10 |
| F-00098 | GTGCCAGCMGCCGCGGTAAAACTCAACAGACAGCTCTGG | 11 |
| F-00116 | GTGCCAGCMGCCGCGGTAATGGGATACTTCGATAGCGTT | 12 |
| F-00137 | GTGCCAGCMGCCGCGGTAAACGAGATCACAGAAAATCGC | 13 |
| F-00154 | GTGCCAGCMGCCGCGGTAAGCATATAGGAAACGATGGGC | 14 |
| F-00168 | GTGCCAGCMGCCGCGGTAAATAATATCTTCGCCTCCTCA | 15 |
| F-00004 | GTGCCAGCMGCCGCGGTAAAACAGAAACTACTGGGGCGA | 16 |
| F-00018 | GTGCCAGCMGCCGCGGTAACACTTACGATTGCGATGACG | 17 |
| F-00034 | GTGCCAGCMGCCGCGGTAAATCAACGACATTGGCCCAGA | 18 |
| F-00048 | GTGCCAGCMGCCGCGGTAACAGCGACTAGATTTTAGGCA | 19 |
| F-00071 | GTGCCAGCMGCCGCGGTAACTAGATTCTAGGTATTTCGG | 20 |
| F-00084 | GTGCCAGCMGCCGCGGTAAGTGAGCATTAAATTTACGTG | 21 |
| F-00099 | GTGCCAGCMGCCGCGGTAAGCTTGATCGAAAAAAAGCAG | 22 |
| F-00120 | GTGCCAGCMGCCGCGGTAAAGGCTTGTCACACATCACGT | 23 |
| F-00138 | GTGCCAGCMGCCGCGGTAAAAAAGAAGGAGATAAGGTTG | 24 |
| F-00156 | GTGCCAGCMGCCGCGGTAAATTCTCTTATCGAGAGCCCG | 25 |
| F-00170 | GTGCCAGCMGCCGCGGTAAATTAGCGTAGATACTCTTCC | 26 |
| F-00007 | GTGCCAGCMGCCGCGGTAACTATCCCTACATCAACACCA | 27 |
| F-00019 | GTGCCAGCMGCCGCGGTAATGCTGGCTCATGTTTCCTTC | 28 |
| F-00035 | GTGCCAGCMGCCGCGGTAAGACGATTCACAGATAAGGAC | 29 |
| F-00053 | GTGCCAGCMGCCGCGGTAACAGAGCTTAAGCAATATGGC | 30 |
| F-00073 | GTGCCAGCMGCCGCGGTAAAAGTAATCTGGTCCGCGACT | 31 |
| F-00085 | GTGCCAGCMGCCGCGGTAATAGACGAGATAGGGTAAGCC | 32 |
| F-00104 | GTGCCAGCMGCCGCGGTAACTGTTAAGTTTTCAATGGCT | 33 |

TABLE 1-continued

| Primer Name | Primer Sequence (5' to 3') | SEQ ID NO. |
|---|---|---|
| F-00123 | GTGCCAGCMGCCGCGGTAATTCTTCTCAAGTTGTGCTTC | 34 |
| F-00142 | GTGCCAGCMGCCGCGGTAAGATCCTGTAGTAATCCGGGA | 35 |
| F-00157 | GTGCCAGCMGCCGCGGTAAGCGCAGATATGCTATACGAG | 36 |
| F-00171 | GTGCCAGCMGCCGCGGTAAGGGTTATTATCGTCGCGGTT | 37 |
| F-00009 | GTGCCAGCMGCCGCGGTAACATGTTATAGGGCTGCGAAC | 38 |
| F-00022 | GTGCCAGCMGCCGCGGTAACAGAATATATAAAGCGTGAC | 39 |
| F-00039 | GTGCCAGCMGCCGCGGTAATTCGCCACCCATATAAACCC | 40 |
| F-00057 | GTGCCAGCMGCCGCGGTAAACTCGCATTCACTAACATGG | 41 |
| F-00075 | GTGCCAGCMGCCGCGGTAAATTAACACATCTATTGGCTC | 42 |
| F-00086 | GTGCCAGCMGCCGCGGTAAAAGTTTTTGAAGCAATGGGG | 43 |
| F-00108 | GTGCCAGCMGCCGCGGTAAAGATATGCCATGCGTGCTGT | 44 |
| F-00126 | GTGCCAGCMGCCGCGGTAAAGTTCGATAAATGAGACGTC | 45 |
| F-00144 | GTGCCAGCMGCCGCGGTAAATCGTAATATTGGCGGTTGC | 46 |
| F-00158 | GTGCCAGCMGCCGCGGTAAAGTTATTTGATTAAGGTGAC | 47 |
| F-00012 | GTGCCAGCMGCCGCGGTAAGTCAGAAGAATCGATAGAGC | 48 |
| F-00024 | GTGCCAGCMGCCGCGGTAACAATACCTAACCAAATCCGC | 49 |
| F-00041 | GTGCCAGCMGCCGCGGTAACAAGCTGTGATGAGACTGCT | 50 |
| F-00058 | GTGCCAGCMGCCGCGGTAAAACAGAAACGTTATCCGCTT | 51 |
| F-00076 | GTGCCAGCMGCCGCGGTAAAAAGCTGATTGATTACGGGA | 52 |
| F-00092 | GTGCCAGCMGCCGCGGTAAACTCTTTCAAAACTTCGGTG | 53 |
| F-00109 | GTGCCAGCMGCCGCGGTAATACAATCGCACCAGTTAGCG | 54 |
| F-00128 | GTGCCAGCMGCCGCGGTAATAGCAGACTCTACATTGGCC | 55 |
| F-00145 | GTGCCAGCMGCCGCGGTAATAGATGTCGTATCCGGAGGA | 56 |
| F-00160 | GTGCCAGCMGCCGCGGTAACGAATGTATGATGGTCGGTC | 57 |
| F-00013 | GTGCCAGCMGCCGCGGTAAGTTATCATGGTGACTCTGCA | 58 |
| F-00025 | GTGCCAGCMGCCGCGGTAACCTAACGAGTTTGATACGCC | 59 |
| F-00042 | GTGCCAGCMGCCGCGGTAAATCTATAACAACTGCGTCAG | 60 |
| F-00059 | GTGCCAGCMGCCGCGGTAACTCAATCCTAGATACGTTGC | 61 |
| F-00078 | GTGCCAGCMGCCGCGGTAACAAGTTAACGCCGATCACTC | 62 |
| F-00095 | GTGCCAGCMGCCGCGGTAATGATACTTAACCAAACCTAC | 63 |
| F-00111 | GTGCCAGCMGCCGCGGTAAAGAATTGTATAGCTTGCAGG | 64 |
| F-00130 | GTGCCAGCMGCCGCGGTAAACATTGATTGCTGCATTCCG | 65 |
| F-00147 | GTGCCAGCMGCCGCGGTAAGATGGAAAAATTAGAGAGAG | 66 |
| F-00163 | GTGCCAGCMGCCGCGGTAATACTACATTCGTGCGATGGG | 67 |
| F-00014 | GTGCCAGCMGCCGCGGTAAATAAAAAGGATCGCCATCCG | 68 |
| F-00028 | GTGCCAGCMGCCGCGGTAATTTCGACCTCTCTGTGTGGA | 69 |
| F-00043 | GTGCCAGCMGCCGCGGTAATTCCAATACTTCTATGCCTC | 70 |
| F-00061 | GTGCCAGCMGCCGCGGTAAAATTGATCGTTGCGTACGGA | 71 |
| F-00079 | GTGCCAGCMGCCGCGGTAACGCAGATAAATGTGGAGCAG | 72 |
| F-00096 | GTGCCAGCMGCCGCGGTAATAGTAGATCACAGAACAACC | 73 |
| F-00112 | GTGCCAGCMGCCGCGGTAACCGTATTCTAAGGTACGGAT | 74 |
| F-00131 | GTGCCAGCMGCCGCGGTAAGCGATCTAATCTTAACAGAC | 75 |
| F-00148 | GTGCCAGCMGCCGCGGTAAAACTGCATTTCAAGTCCGAA | 76 |
| F-00164 | GTGCCAGCMGCCGCGGTAATCTGAACTTCCCTATCTCCA | 77 |
| F-00016 | GTGCCAGCMGCCGCGGTAAAAGAGTAGAGGATTTCGTGT | 78 |
| F-00031 | GTGCCAGCMGCCGCGGTAAACTCTCTAAAATGCAGTCGG | 79 |
| F-00044 | GTGCCAGCMGCCGCGGTAATAGTGACTAGGGTAAATGCC | 80 |
| F-00067 | GTGCCAGCMGCCGCGGTAACTTACACCCTACGTTGCTGA | 81 |
| F-00081 | GTGCCAGCMGCCGCGGTAATTGAGGTTAAGTTGTTTGCC | 82 |
| F-00097 | GTGCCAGCMGCCGCGGTAAGTGTTAGGTTTTGATGAACC | 83 |

TABLE 1-continued

| Primer Name | Primer Sequence (5' to 3') | SEQ ID NO. |
|---|---|---|
| F-00113 | GTGCCAGCMGCCGCGGTAAAAATTATCTGTGGATTGCCG | 84 |
| F-00136 | GTGCCAGCMGCCGCGGTAAAGATAGATGGTGTACTGCAC | 85 |
| F-00150 | GTGCCAGCMGCCGCGGTAAAGATGCAAATACCCGGGTAC | 86 |
| F-00165 | GTGCCAGCMGCCGCGGTAATCAACGTCAGGCAATGTGTC | 87 |
| F-seq | GTGCCAGCMGCCGCGGTAA | 88 |
| R-00003 | GGACTACHVGGGTWTCTAATAATGTGTCCAGCAGAAGCAG | 89 |
| R-00017 | GGACTACHVGGGTWTCTAATTGTTTAAGCTGGACTGCCAC | 90 |
| R-00033 | GGACTACHVGGGTWTCTAATACTCTCTGGCAACTCCCCAA | 91 |
| R-00046 | GGACTACHVGGGTWTCTAATTGGCACTCTCTCACAGCCAA | 92 |
| R-00069 | GGACTACHVGGGTWTCTAATACACCCTCCCAAGTATGGTG | 93 |
| R-00083 | GGACTACHVGGGTWTCTAATTTGTAGCTTTCCCACCAGAG | 94 |
| R-00098 | GGACTACHVGGGTWTCTAATTTTCGGGAGACTGGTCGCTT | 95 |
| R-00116 | GGACTACHVGGGTWTCTAATCCTGGCATTCTAGCGTACCC | 96 |
| R-00137 | GGACTACHVGGGTWTCTAATTAAGACCATCACGCTACGGG | 97 |
| R-00154 | GGACTACHVGGGTWTCTAATTCGTGCAATAATAGTCGCCC | 98 |
| R-00168 | GGACTACHVGGGTWTCTAATGCTACTGGAAAAACCACCCT | 99 |
| R-00004 | GGACTACHVGGGTWTCTAATAGTGGCAAAAACAGGCAAGC | 100 |
| R-00018 | GGACTACHVGGGTWTCTAATTGCTTGGCGTTGTCAGCTTC | 101 |
| R-00034 | GGACTACHVGGGTWTCTAATCATCTGATTCACACAGTGGC | 102 |
| R-00048 | GGACTACHVGGGTWTCTAATTAAGCATTTCCTGCCCACCG | 103 |
| R-00071 | GGACTACHVGGGTWTCTAATAAGCACTTAAGGACGGCGGT | 104 |
| R-00084 | GGACTACHVGGGTWTCTAATAAACGATCTACGTGGGACCC | 105 |
| R-00099 | GGACTACHVGGGTWTCTAATATTTGCTCTGCCTTGAAGCG | 106 |
| R-00120 | GGACTACHVGGGTWTCTAATCGCACTAACATAGTGCAGGG | 107 |
| R-00138 | GGACTACHVGGGTWTCTAATTAGGGGTTTCCCCTATGGAC | 108 |
| R-00156 | GGACTACHVGGGTWTCTAATTCGACTAGTCGGGTTTGGGT | 109 |
| R-00170 | GGACTACHVGGGTWTCTAATCAGCTAAAACCCCTGCCTGC | 110 |
| R-00007 | GGACTACHVGGGTWTCTAATGGAGATATGATCGTTCCGCA | 111 |
| R-00019 | GGACTACHVGGGTWTCTAATTCTACAGCCGCTTCACGCTC | 112 |
| R-00035 | GGACTACHVGGGTWTCTAATCCGTTAAATAGGGAGGCTCG | 113 |
| R-00053 | GGACTACHVGGGTWTCTAATTTAACAATCCTCCCCAAGGG | 114 |
| R-00073 | GGACTACHVGGGTWTCTAATGTAACGTGAGAGAATGCGAC | 115 |
| R-00085 | GGACTACHVGGGTWTCTAATTTAGGCCCTCTGAAGAAGGC | 116 |
| R-00104 | GGACTACHVGGGTWTCTAATTTGGCTGGTTTAGGAGTAGG | 117 |
| R-00123 | GGACTACHVGGGTWTCTAATGAACTGACATCATTGGGGCT | 118 |
| R-00142 | GGACTACHVGGGTWTCTAATAGTTTGACCTCAGCGCCATG | 119 |
| R-00157 | GGACTACHVGGGTWTCTAATTAGTCGTTCGCTCCGGCATC | 120 |
| R-00171 | GGACTACHVGGGTWTCTAATTTCAGTGACTGTGAGATGCC | 121 |
| R-00009 | GGACTACHVGGGTWTCTAATACGACCTATATCAGCCGACG | 122 |
| R-00022 | GGACTACHVGGGTWTCTAATACCAGTTGGGAGGGAGGTCT | 123 |
| R-00039 | GGACTACHVGGGTWTCTAATGGCGAGGTCATCATACCCTG | 124 |
| R-00057 | GGACTACHVGGGTWTCTAATCGATACGGTCTAACTCGCGT | 125 |
| R-00075 | GGACTACHVGGGTWTCTAATCTGCTCCAACTACTGGGGCT | 126 |
| R-00086 | GGACTACHVGGGTWTCTAATCTCTGCTCCATCCCTCCAAC | 127 |
| R-00108 | GGACTACHVGGGTWTCTAATTGGCTCATATCAGTGCAGCA | 128 |
| R-00126 | GGACTACHVGGGTWTCTAATAATGGCCGGTTAACGCACTC | 129 |
| R-00144 | GGACTACHVGGGTWTCTAATCAAGCTATTTCGATCGCGTG | 130 |
| R-00158 | GGACTACHVGGGTWTCTAATTTGCATGTAACGCCCACCAC | 131 |
| R-00012 | GGACTACHVGGGTWTCTAATCAAGAATGAAGTAGTGCGGG | 132 |
| R-00024 | GGACTACHVGGGTWTCTAATTTGGTGGAAGCCGTATGCTC | 133 |

TABLE 1-continued

| Primer Name | Primer Sequence (5' to 3') | SEQ ID NO. |
|---|---|---|
| R-00041 | GGACTACHVGGGTWTCTAATCCGATAAGAAGCGCTCCCAC | 134 |
| R-00058 | GGACTACHVGGGTWTCTAATGCCGAGCCTCTTTATCCAGC | 135 |
| R-00076 | GGACTACHVGGGTWTCTAATTTTACCGATGAGAAACGCCC | 136 |
| R-00092 | GGACTACHVGGGTWTCTAATTCCGAGTACATAGAGGCGAC | 137 |
| R-00109 | GGACTACHVGGGTWTCTAATGATCAGACTTCGCGTCGACG | 138 |
| R-00128 | GGACTACHVGGGTWTCTAATCTATAGCCCTCCACCCGCTC | 139 |
| R-00145 | GGACTACHVGGGTWTCTAATTAGTCATGCGTATGCGCTTC | 140 |
| R-00160 | GGACTACHVGGGTWTCTAATGCATAACTCCTACACGGTGG | 141 |
| R-00013 | GGACTACHVGGGTWTCTAATCCGTAATGAGGAATTTGCGG | 142 |
| R-00025 | GGACTACHVGGGTWTCTAATCGAAGGGGCAGAGTAGACG | 143 |
| R-00042 | GGACTACHVGGGTWTCTAATGCACTTACCTGGAGAGAAGG | 144 |
| R-00059 | GGACTACHVGGGTWTCTAATGCGAAGCGATACCCTACGCT | 145 |
| R-00078 | GGACTACHVGGGTWTCTAATCCTTGTAAGCTACGCCCAGA | 146 |
| R-00095 | GGACTACHVGGGTWTCTAATGGATGAACCAACATCTGCCT | 147 |
| R-00111 | GGACTACHVGGGTWTCTAATTCTTGCGTTAACGGTTTCCG | 148 |
| R-00130 | GGACTACHVGGGTWTCTAATCGTCGTCCTCAAATTTCGCA | 149 |
| R-00147 | GGACTACHVGGGTWTCTAATAACCTCTGGGTTTAAGCCGA | 150 |
| R-00163 | GGACTACHVGGGTWTCTAATATTCACGAAATGCTCCTCGC | 151 |
| R-00014 | GGACTACHVGGGTWTCTAATACGGAATCCTTTGACGGGAT | 152 |
| R-00028 | GGACTACHVGGGTWTCTAATACGACGTGAATTCGAGGGCT | 153 |
| R-00043 | GGACTACHVGGGTWTCTAATTTAGTGGTGTTCCAGCCTCT | 154 |
| R-00061 | GGACTACHVGGGTWTCTAATGTCTATCACGAGATCAGGCA | 155 |
| R-00079 | GGACTACHVGGGTWTCTAATAGCAGAGGAAATGAACGTCG | 156 |
| R-00096 | GGACTACHVGGGTWTCTAATTGGATCGAGGTCATGACTGG | 157 |
| R-00112 | GGACTACHVGGGTWTCTAATGGACTCGAGCCTATTTCCCA | 158 |
| R-00131 | GGACTACHVGGGTWTCTAATGAGCAGGTGAAGTACGCTCA | 159 |
| R-00148 | GGACTACHVGGGTWTCTAATGAGGGGTAGACGCCAGGTCT | 160 |
| R-00164 | GGACTACHVGGGTWTCTAATCTTTACGGGCCACCAGGAAC | 161 |
| R-00016 | GGACTACHVGGGTWTCTAATGTGTCAATGAAAGGAGAGCG | 162 |
| R-00031 | GGACTACHVGGGTWTCTAATGACATCCGCAACAATGTACC | 163 |
| R-00044 | GGACTACHVGGGTWTCTAATGGCGTAGTACGGGAAGAGGG | 164 |
| R-00067 | GGACTACHVGGGTWTCTAATATTGTCTGCAACAAGGGCCA | 165 |
| R-00081 | GGACTACHVGGGTWTCTAATAGCGTGCAACTAGAGGGTCG | 166 |
| R-00097 | GGACTACHVGGGTWTCTAATTAGACCAGACCCAAGAGGGG | 167 |
| R-00113 | GGACTACHVGGGTWTCTAATCCTAAACCCAAAAGTCGGGT | 168 |
| R-00136 | GGACTACHVGGGTWTCTAATAGGCGAACTCGGAAACTCGC | 169 |
| R-00150 | GGACTACHVGGGTWTCTAATATGGGGTCAAGACACCTAGC | 170 |
| R-00165 | GGACTACHVGGGTWTCTAATCTAACTCAACAGACGGACCC | 171 |
| R-seq | GGACTACHVGGGTWTCTAAT | 172 |

TABLE 2

| | | | | | | 50,000X Master Stocks Amounts Added for 100 μL Mix | | | | | |
|---|---|---|---|---|---|---|---|---|---|---|---|
| | | | | | | Mix A | | Mix B | | Mix C | |
| | PCR Conc ng/μL | PCR Conc. Molecules/μL | 50,000X Master Stocks Desired Concentration Molecules per μL | | | PCR Amount Added (μL) | Dilution Factor Used | PCR Amount Added (μL) | Dilution Factor Used | PCR Amount Added (μ/L) | Dilution Factor Used |
| Spike_Name | | | Mix A | Mix B | Mix C | | | | | | |
| ERCC-00004 | 4.15 | 1.40E+10 | 1.88E+07 | 3.00E+08 | 4.50E+03 | 1.34 | 10 | 2.14 | 1 | 1.60 | 50000 |
| ERCC-00007 | 11 | 3.73E+10 | 3.75E+07 | 5.86E+05 | 6.00E+08 | 1.00 | 10 | 1.57 | 1000 | 1.61 | 1 |

TABLE 2-continued

| | | | | | | 50,000X Master Stocks Amounts Added for 100 μL Mix | | | | | |
| | | | | | | Mix A | | Mix B | | Mix C | |
| Spike_Name | PCR Conc ng/μL | PCR Conc. Molecules/μL | 50,000X Master Stocks Desired Concentration Molecules per μL | | | PCR Amount Added (μL) | Dilution Factor Used | PCR Amount Added (μL) | Dilution Factor Used | PCR Amount Added (μ/L) | Dilution Factor Used |
| | | | Mix A | Mix B | Mix C | | | | | | |
|---|---|---|---|---|---|---|---|---|---|---|---|
| ERCC-00013 | 10.93 | 3.67E+10 | 1.50E+08 | 1.17E+06 | 2.93E+05 | 1.23 | 3 | 1.60 | 500 | 1.60 | 2000 |
| ERCC-00014 | 10.8 | 3.64E+10 | 3.75E+07 | 3.75E+07 | 7.30E+04 | 1.03 | 10 | 1.03 | 10 | 1.00 | 5000 |
| ERCC-00018 | 9.6 | 3.24E+10 | 7.50E+07 | 9.38E+06 | 7.50E+07 | 1.16 | 5 | 1.45 | 50 | 1.16 | 5 |
| ERCC-00024 | 12.4 | 4.18E+10 | 1.47E+05 | 1.17E+06 | 9.00E+03 | 1.75 | 5000 | 1.40 | 500 | 1.08 | 50000 |
| ERCC-00025 | 8.33 | 2.81E+10 | 1.20E+09 | 1.88E+07 | 1.20E+09 | 4.27 | 1 | 1.34 | 20 | 4.27 | 1 |
| ERCC-00028 | 13.53 | 4.57E+10 | 4.69E+06 | 1.85E+04 | 7.50E+07 | 1.02 | 100 | 1.21 | 30000 | 1.31 | 8 |
| ERCC-00031 | 13.47 | 4.54E+10 | 1.00E+03 | 2.93E+05 | 4.50E+02 | 1.10 | 500000 | 1.29 | 2000 | 0.99 | 100000 |
| ERCC-00033 | 12.2 | 4.09E+10 | 1.47E+05 | 1.47E+05 | 4.69E+06 | 1.79 | 5000 | 1.79 | 5000 | 1.15 | 100 |
| ERCC-00034 | 10.8 | 3.64E+10 | 3.00E+08 | 1.50E+08 | 9.38E+06 | 1.65 | 2 | 1.24 | 3 | 1.29 | 50 |
| ERCC-00035 | 13 | 4.38E+10 | 1.00E+03 | 7.50E+07 | 1.00E+03 | 1.14 | 500000 | 1.71 | 10 | 1.14 | 500000 |
| ERCC-00039 | 11.87 | 4.01E+10 | 9.38E+06 | 3.00E+08 | 3.75E+07 | 1.17 | 50 | 1.50 | 2 | 1.87 | 20 |
| ERCC-00041 | 13.73 | 4.61E+10 | 1.17E+06 | 2.93E+05 | 2.93E+05 | 1.27 | 500 | 1.27 | 2000 | 1.27 | 2000 |
| ERCC-00042 | 10.47 | 3.55E+10 | 7.50E+07 | 7.30E+04 | 1.17E+06 | 1.06 | 5 | 1.03 | 5000 | 1.65 | 500 |
| ERCC-00044 | 11.67 | 3.95E+10 | 7.30E+04 | 6.00E+08 | 9.38E+06 | 1.11 | 6000 | 1.52 | 1 | 1.19 | 50 |
| ERCC-00046 | 9.27 | 3.12E+10 | 2.93E+05 | 1.20E+09 | 1.88E+07 | 1.13 | 1200 | 3.85 | 1 | 1.20 | 20 |
| ERCC-00048 | 12.4 | 4.16E+10 | 1.50E+08 | 3.65E+04 | 1.47E+05 | 1.08 | 3 | 1.05 | 12000 | 1.06 | 3000 |
| ERCC-00053 | 10.33 | 3.46E+10 | 2.50E+03 | 3.50E+03 | 2.50E+03 | 1.45 | 200000 | 1.45 | 200000 | 1.45 | 200000 |
| ERCC-00057 | 11.93 | 4.03E+10 | 4.69E+06 | 4.69E+06 | 2.50E+03 | 1.16 | 100 | 1.16 | 100 | 1.24 | 200000 |
| ERCC-00059 | 11.87 | 4.01E+10 | 1.17E+06 | 1.00E+03 | 1.88E+07 | 1.46 | 500 | 1.25 | 500000 | 1.40 | 30 |
| ERCC-00061 | 11.07 | 3.74E+10 | 1.00E+03 | 1.47E+05 | 3.00E+08 | 1.34 | 500000 | 1.18 | 3000 | 1.60 | 2 |
| ERCC-00069 | 12.2 | 4.12E+10 | 1.47E+05 | 3.75E+07 | 3.00E+08 | 1.78 | 5000 | 1.82 | 20 | 1.46 | 2 |
| ERCC-00071 | 12 | 4.06E+10 | 4.69E+06 | 4.69E+06 | 4.69E+06 | 1.15 | 100 | 1.15 | 100 | 1.15 | 100 |
| ERCC-00073 | 14.8 | 5.00E+10 | 5.86E+05 | 4.50E+03 | 1.85E+04 | 1.17 | 1000 | 1.80 | 200000 | 1.11 | 30000 |
| ERCC-00075 | 5.87 | 1.98E+10 | 1.17E+06 | 2.93E+05 | 1.50E+08 | 1.18 | 200 | 1.48 | 1000 | 1.51 | 2 |
| ERCC-00076 | 12.87 | 4.34E+10 | 2.34E+06 | 1.50E+08 | 2.93E+05 | 1.08 | 200 | 1.73 | 5 | 1.35 | 2000 |
| ERCC-00078 | 13.2 | 4.47E+10 | 2.93E+05 | 1.88E+07 | 7.30E+04 | 1.31 | 2000 | 1.26 | 30 | 1.63 | 10000 |
| ERCC-00079 | 11.73 | 3.94E+10 | 2.93E+05 | 1.00E+03 | 1.88E+07 | 1.49 | 2000 | 1.27 | 500000 | 1.43 | 30 |
| ERCC-00081 | 12.4 | 4.19E+10 | 7.50E+07 | 7.50E+07 | 1.00E+03 | 1.79 | 10 | 1.79 | 10 | 1.19 | 500000 |
| ERCC-00083 | 10.2 | 3.45E+10 | 1.88E+07 | 1.88E+07 | 1.88E+07 | 1.09 | 20 | 1.09 | 20 | 1.09 | 20 |
| ERCC-00084 | 12.67 | 4.28E+10 | 6.00E+08 | 1.50E+08 | 1.00E+03 | 1.40 | 1 | 1.05 | 3 | 1.17 | 500000 |
| ERCC-00085 | 10.33 | 3.48E+10 | 1.20E+09 | 5.86E+05 | 3.00E+08 | 3.44 | 1 | 1.68 | 1000 | 1.72 | 2 |
| ERCC-00086 | 13.73 | 4.59E+10 | 1.17E+06 | 1.17E+06 | 1.17E+06 | 1.28 | 500 | 1.28 | 500 | 1.28 | 500 |
| ERCC-00092 | 10.33 | 3.49E+10 | 6.00E+08 | 6.00E+08 | 6.00E+08 | 1.72 | 1 | 1.72 | 1 | 1.72 | 1 |
| ERCC-00095 | 11.4 | 3.87E+10 | 9.00E+03 | 1.88E+07 | 1.85E+04 | 1.16 | 50000 | 1.46 | 30 | 1.44 | 30000 |
| ERCC-00096 | 15.93 | 5.39E+10 | 7.30E+04 | 7.30E+04 | 7.30E+04 | 1.35 | 10000 | 1.35 | 10000 | 1.35 | 10000 |
| ERCC-00097 | 12.93 | 4.38E+10 | 9.38E+06 | 4.50E+03 | 1.85E+04 | 1.07 | 50 | 1.03 | 100000 | 1.27 | 30000 |
| ERCC-00098 | 12.27 | 4.14E+10 | 5.86E+05 | 7.30E+04 | 5.86E+05 | 1.42 | 1000 | 1.06 | 6000 | 1.42 | 1000 |
| ERCC-00099 | 10.2 | 3.44E+10 | 4.50E+03 | 1.85E+04 | 1.50E+08 | 1.31 | 100000 | 1.08 | 20000 | 1.31 | 3 |
| ERCC-00104 | 9.2 | 3.12E-10 | 1.20E+09 | 7.30E+04 | 1.17E+06 | 3.84 | 1 | 1.17 | 5000 | 1.88 | 500 |
| ERCC-00108 | 13.87 | 4.68E+10 | 2.34E+06 | 1.00E+06 | 9.38E+06 | 1.00 | 200 | 1.07 | 500000 | 1.00 | 50 |
| ERCC-00109 | 13.27 | 4.47E+10 | 7.30E+04 | 3.75E+07 | 7.50E+07 | 1.63 | 10000 | 1.68 | 20 | 1.34 | 8 |
| ERCC-00111 | 11.73 | 3.95E+10 | 1.88E+07 | 2.34E+06 | 9.00E+03 | 1.42 | 30 | 1.19 | 200 | 1.14 | 50000 |
| ERCC-00112 | 11.2 | 3.78E+10 | 1.50E+08 | 5.86E-05 | 7.30E+04 | 1.99 | 5 | 1.55 | 1000 | 1.16 | 6000 |
| ERCC-00113 | 9.4 | 3.17E+10 | 3.00E+08 | 7.30E+04 | 2.93E+05 | 1.89 | 2 | 1.15 | 5000 | 1.11 | 1200 |
| ERCC-00116 | 14.27 | 4.81E+10 | 2.93E+05 | 2.93E+05 | 1.00E+03 | 1.22 | 2000 | 1.22 | 2000 | 1.04 | 500000 |
| ERCC-00123 | 10.47 | 3.55E+10 | 1.00E+03 | 2.50E+03 | 1.50E+08 | 1.41 | 500000 | 1.41 | 200000 | 1.27 | 3 |
| ERCC-00126 | 11.87 | 4.02E+10 | 1.88E+07 | 9.38E+06 | 3.75E+07 | 1.40 | 30 | 1.17 | 50 | 1.87 | 20 |
| ERCC-00128 | 12.87 | 4.33E+10 | 1.00E+03 | 6.00E+08 | 4.69E+06 | 1.15 | 500000 | 1.38 | 1 | 1.03 | 100 |
| ERCC-00131 | 16.73 | 5.63E+10 | 7.30E+04 | 1.47E+05 | 4.50E+03 | 1.30 | 10000 | 1.30 | 5000 | 1.60 | 200000 |
| ERCC-00136 | 14.6 | 4.91E+10 | 5.86E+05 | 4.50E+03 | 2.50E+03 | 1.19 | 1000 | 1.10 | 120000 | 1.02 | 200000 |
| ERCC-00137 | 13.53 | 4.57E+10 | 3.75E+07 | 1.17E+06 | 3.65E+04 | 1.64 | 20 | 1.28 | 500 | 1.60 | 20000 |
| ERCC-00138 | 7.13 | 2.40E+10 | 6.00E+08 | 3.00E+08 | 1.50E+08 | 2.50 | 1 | 1.25 | 1 | 1.25 | 2 |
| ERCC-00142 | 12.87 | 4.33E+10 | 7.30E+04 | 6.00E+08 | 4.69E+06 | 1.01 | 6000 | 1.38 | 1 | 1.08 | 100 |
| ERCC-00144 | 11.4 | 3.84E+10 | 3.65E+04 | 1.00E+03 | 1.20E+09 | 1.14 | 12000 | 1.30 | 500000 | 3.13 | 1 |
| ERCC-00145 | 14.27 | 4.80E+10 | 4.69E+06 | 1.85E+04 | 2.93E+05 | 1.17 | 120 | 1.93 | 50000 | 1.22 | 2000 |
| ERCC-00147 | 13 | 4.35E+10 | 2.93E+05 | 1.85E+04 | 4.69E+06 | 1.35 | 2000 | 1.28 | 30000 | 1.08 | 100 |
| ERCC-00148 | 13.33 | 4.47E+10 | 1.88E+07 | 2.34E+06 | 1.17E+06 | 1.26 | 30 | 1.05 | 200 | 1.31 | 500 |
| ERCC-00154 | 12.6 | 4.24E+10 | 2.50E+03 | 1.20E+09 | 1.85E+04 | 1.18 | 200000 | 2.83 | 1 | 1.31 | 30000 |
| ERCC-00156 | 14.53 | 4.90E+10 | 1.17E+06 | 9.00E+03 | 1.00E+03 | 1.19 | 500 | 1.28 | 70000 | 1.02 | 500000 |
| ERCC-00157 | 13.6 | 4.58E+10 | 9.38E+06 | 1.17E+06 | 9.00E+03 | 1.02 | 50 | 1.28 | 500 | 1.37 | 70000 |
| ERCC-00160 | 11.8 | 3.97E+10 | 1.50E+08 | 4.50E+03 | 7.50E+07 | 1.13 | 3 | 1.13 | 100000 | 1.51 | 8 |
| ERCC-00163 | 11.2 | 3.78E+10 | 4.69E+06 | 1.50E+08 | 1.20E+09 | 1.24 | 100 | 1.19 | 3 | 3.18 | 1 |
| ERCC-00164 | 12.67 | 4.30E+10 | 2.34E+06 | 2.34E+06 | 2.34E+06 | 1.09 | 200 | 1.09 | 200 | 1.09 | 200 |
| ERCC-00165 | 14.2 | 4.80E+10 | 9.00E+03 | 3.65E+04 | 1.17E+06 | 1.88 | 100000 | 1.52 | 20000 | 1.22 | 500 |
| ERCC-00168 | 9.2 | 3.12E+10 | 4.50E+03 | 4.50E+03 | 6.00E+08 | 1.44 | 100000 | 1.44 | 100000 | 1.92 | 1 |

TABLE 2-continued

| | | | | | | 50,000X Master Stocks Amounts Added for 100 μL Mix | | | | | |
|---|---|---|---|---|---|---|---|---|---|---|---|
| | | | | | | Mix A | | Mix B | | Mix C | |
| | PCR Conc ng/ | PCR Conc. Molecules/ | 50,000X Master Stocks Desired Concentration Molecules per μL | | | PCR Amount Added | Dilution Factor | PCR Amount Added | Dilution Factor | PCR Amount Added | Dilution Factor |
| Spike_Name | μL | μL | Mix A | Mix B | Mix C | (μL) | Used | (μL) | Used | (μ/L) | Used |
| ERCC-00170 | 8.2 | 2.75E+10 | 6.00E+08 | 2.93E+05 | 5.86E+05 | 2.18 | 1 | 1.07 | 1000 | 1.07 | 500 |
| ERCC-00171 | 8.87 | 2.99E+10 | 3.00E+08 | 1.20E+09 | 6.00E+08 | 1.00 | 1 | 4.01 | 1 | 2.01 | 1 |
| | | Total Volume of Mix | | | | 99.79 | | 99.79 | | 98.58 | |
| | | Volume of TE | | | | 0.21 | | 0.21 | | 1.42 | |

---

What is claimed is:

1. A processor-implemented method of determining at least one evaluation parameter of a sample for a differential abundance analysis among a set of samples that were previously sequenced, comprising:

receiving, at a sequence processing validation device, sequence data for the set of samples, wherein the set of samples comprises at least two samples, each sample includes a mixture of sample microbiome polynucleotides and spike-mix polynucleotides, the spike-mix polynucleotides comprise at least two unique spike-mix polynucleotide sequences, the at least two unique spike-mix polynucleotide sequences previously had at least two different concentrations in the set of samples prior to sequencing, the at least two unique spike-mix polynucleotide sequences have different percent GC contents, and the sequence data comprising sample microbiome sequence data for sample microbiome polynucleotide sequences and polynucleotide spike-mix sequence data for the spike-mix polynucleotide sequences;

determining measures of sequence similarity of each sequence within the sequence data to all other sequences within the sequence data of each sample;

identifying clusters of sequences based on a comparison of the measures of sequence similarity to one or more threshold values in each sample, wherein the clusters include (i) one or more sample clusters of the sample microbiome nucleotide sequences and (ii) one or more polynucleotide spike-mix clusters of the spike-mix polynucleotide sequences, thereby generating clustered sequence data for each sample;

generating a set of calculated differential abundance estimates of the clusters of sequences between each sample of the set of samples, wherein the calculated differential abundance estimates include (i) sample calculated differential abundance estimates of the one or more sample clusters and (ii) spike-mix calculated differential abundance estimates of the one or more polynucleotide spike-mix clusters;

generating spike-mix expected differential abundance estimates of the one or more polynucleotide spike-mix clusters for each sample;

determining a difference between the expected differential abundance of the one or more polynucleotide spike-mix clusters and the spike-mix calculated differential abundance estimates for each sample of the set of samples;

determining at least one evaluation parameter of the polynucleotide spike-mix sequence data based on the determined difference, wherein determining the at least one evaluation parameter comprises (i) selecting an evaluation criteria from among the group consisting of sensitivity, spk16_specificity, accuracy, precision, theta, sigma, inverse false negative, inverse false positive, detection rate, and spk16_PPV and (ii) determining a value for the evaluation parameter, wherein spk16_specificity was determined by dividing the sum of true-negative spike-mix polynucleotides and sample microbiome polynucleotides identified by the sum of spike-mix polynucleotides and sample microbiome polynucleotides that were not expected to be differentially abundant, theta was determined using the slope of a regression of observed log 2FC and expected log 2FC as absolute(atan(((slope−expected slope)/(1+expected slope*slope))))*(180/π), in which the expected slope was 1 (observed log 2FC=expected log 2FC), sigma was determined using the square root of the sum of residual errors of each spike comparisons compared to a line with a slope of 1, and spk16_PPV was determined as the total true positives divided by the sum of the total true positives+total false positives+total false positive of the sample microbiome polynucleotides; and outputting the at least one evaluation parameter for each sample of the set of samples, wherein the at least one evaluation parameter assesses the sensitivity, reproducibility, and/or accuracy of the differential abundance analysis.

2. The method of claim 1, the method further comprising:

categorizing the expected differential abundance estimates and the calculated differential abundance estimates of the one or more polynucleotide spike-mix clusters based on a measure of relative abundance of each spike-mix polynucleotide sequence to generate a concentration category, wherein each spike-mix polynucleotide sequence was added to the each sample of the set of samples different concentrations; and determining a difference between the expected differential abundance of the one or more polynucleotide spike-mix clusters and the spike-mix calculated differential abundance estimates further including comparing the expected differential abundance estimates of the one or more polynucleotide spike-mix clusters in each concentration category with the calculated differential abundance estimates of the one or more polynucleotide spike-mix clusters in the same category;

wherein determining at least one evaluation parameter of the polynucleotide spike-mix sequence data based on the determined difference comprises determining a unique value for the evaluation parameter for each category of differential abundance estimates of the one or more polynucleotide spike-mix clusters.

3. The method of claim 1, wherein at least two sets of spike-mix polynucleotides include the same set of spike-mix sequences in the set of samples, the spike-mix polynucleotides are further configured such that each spike mix polynucleotide includes a first subset of the set of template spike sequences with a copy number that is the same as the copy number of that first subset of template spike sequence in the remaining polynucleotide spike mixes;

each polynucleotide spike mix includes a second subset of the set of template spike sequences with a copy number that is different from the copy number of that second subset of template spike sequence in at least one of the remaining polynucleotide spike mixes, the difference in copy number being approximately one order of magnitude;

each polynucleotide spike mix includes a third subset of the set of template spike sequences with a copy number that is different from the copy number of that third subset of template spike sequence in at least one of the remaining polynucleotide spike mixes, the difference in copy number being more than one order of magnitude.

4. The method of claim 1, wherein the identifying clusters of sequences includes clustering the sequence data into operational taxonomic units.

5. The method of claim 1, wherein the identifying clusters of sequences includes mapping the sample microbiome sequence data against a reference database.

6. The method of claim 1, wherein the identifying clusters of sequences includes implementing one or more methods of error-correction such that the clusters are defined based on a set of amplicon sequence variants.

7. The method of claim 1, wherein the generating a set of calculated differential abundance estimates of the clusters of sequences includes hypothesis testing using the clustered sequence data.

8. A method of determining validity of differential abundance analysis result among a set of samples, the method comprising:

extracting DNA from each biological sample in the set of biological samples to produce DNA solutions;

mixing each of the DNA solutions with spike mix polynucleotides to generate sequencing samples, wherein the spike-mix polynucleotides comprise at least two unique spike-mix polynucleotide sequences, the at least two unique spike-mix polynucleotide sequences have at least two different concentrations in the set of samples prior to sequencing, the at least two unique spike-mix polynucleotide sequences have different percent GC contents;

amplifying one or more target sequences in the sequencing samples, thereby obtaining at least one amplified product;

sequencing the at least one amplified products to generate sequence data;

receiving, at a sequence processing validation device, sequence data for the at least one amplified product, wherein the sequence data comprises biological sample microbiome sequence data for the DNA solutions and polynucleotide spike-mix sequence data for the spike-mix polynucleotides determining measures of sequence similarity of each sequence within the sequence data to all other sequences within the sequence data;

identifying clusters of sequences-based on a comparison of the measures of sequence similarity to one or more threshold values in each biological sample, wherein the clusters include (i) one or more sample clusters of the sample microbiome nucleotide sequences and (ii) one or more polynucleotide spike-mix clusters of the spike-mix polynucleotide sequences;

generating a set of calculated differential abundance estimates of the clusters of sequences, wherein the calculated differential abundance estimates include (i) sample calculated differential abundance estimates of the one or more sample clusters and (ii) spike-mix calculated differential abundance estimates of the one or more polynucleotide spike-mix clusters;

generating spike-mix expected differential abundance estimates of the one or more polynucleotide spike-mix clusters for each sample;

determining a difference between the expected differential abundance of the one or more polynucleotide spike-mix clusters and the spike-mix calculated differential abundance estimates for each sample;

determining at least one evaluation parameter of the polynucleotide spike-mix sequence data based on the determined difference, wherein determining the at least one evaluation parameter comprises (i) selecting an evaluation criteria from among the group consisting of sensitivity, spk16_specificity, accuracy, precision, theta, sigma, inverse false negative, inverse false positive, detection rate, and spk16_PPV and (ii) determining a value for the evaluation parameter, wherein spk16_specificity is determined by dividing the sum of true-negative spike-mix polynucleotides and sample microbiome polynucleotides identified by the sum of spike-mix polynucleotides and sample microbiome polynucleotides that were not expected to be differentially abundant, theta is determined using the slope of a regression of observed log 2FC and expected log 2FC as absolute(atan(((slope−expected slope)/(1+expected slope*slope))))*(180/$\pi$), in which the expected slope was 1 (observed log 2FC=expected log 2FC), sigma is determined using the square root of the sum of residual errors of each spike comparisons compared to a line with a slope of 1, and spk16_PPV is determined as the total true positives divided by the total true positives+ total false positives+total false positive of the sample microbiome polynucleotides; and outputting the at least one evaluation parameter of each sample of the set of samples;

thereby inferring the validity of the differential abundance analysis result for the at least two biological samples, wherein the validity comprises the robustness or reproducibility of the differential abundance analysis.

9. The method of claim 8, wherein the biological sample is a blood sample, a tissue sample, a skin sample, a urine sample, or a stool sample.

10. The method of claim 1, wherein the percent GC contents are between 35% and 60%.

11. The method of claim 1, wherein the percent GC contents approximate a range of percent GC contents of the sample microbiome polynucleotide sequences.

12. The method of claim 8, wherein the percent GC contents are between 35% and 60%.

13. The method of claim 8, wherein the percent GC contents approximate a range of percent GC contents of the sample microbiome polynucleotide sequences.

\* \* \* \* \*

UNITED STATES PATENT AND TRADEMARK OFFICE
CERTIFICATE OF CORRECTION

| | | |
|---|---|---|
| PATENT NO. | : 11,473,133 B2 | Page 1 of 1 |
| APPLICATION NO. | : 16/581712 | |
| DATED | : October 18, 2022 | |
| INVENTOR(S) | : Cheryl-Emiliane T. Chow et al. | |

It is certified that error appears in the above-identified patent and that said Letters Patent is hereby corrected as shown below:

On the Title Page

Page 2

Column 2 (item (56) Other Publications), Line 48, delete "e!003531" and insert -- e1003531 --.

Column 2 (item (56) Other Publications), Line 71, delete "Biochemistiy" and insert -- biochemistry --.

In the Claims

Column 102, Line 29, in Claim 8, delete "products" and insert -- product --.

Signed and Sealed this
Twenty-eighth Day of February, 2023

*Katherine Kelly Vidal*

Katherine Kelly Vidal
*Director of the United States Patent and Trademark Office*